(12) United States Patent
Rudell, Jr. et al.

(10) Patent No.: US 10,174,378 B2
(45) Date of Patent: Jan. 8, 2019

(54) GENE EXPRESSION MONITORING FOR RISK ASSESSMENT OF APPLE AND PEAR FRUIT STORAGE STRESS AND PHYSIOLOGICAL DISORDERS

(71) Applicants: The United States of America, as represented by the Secretary of Agriculture, Washington, DC (US); CORNELL UNIVERSITY, Ithaca, NY (US); THE NEW ZEALAND INSTITUTE FOR PLANT AND FOOD RESEARCH LIMITED, Auckland (NZ); KATHOLIEKE UNIVERSITEIT LEUVEN, Heverlee (BE)

(72) Inventors: David R. Rudell, Jr., Wanatchee, WA (US); Rachel S. Leisso, Wanatchee, WA (US); James P. Mattheis, Wanatchee, WA (US); James J. Giovannoni, Ithaca, NY (US); Nigel E. Gapper, Dryden, NY (US); Nicolai M. Bart, Heusden (BE); Chris B. Watkins, Ithaca, NY (US); Jason W. Johnston, Havelock North (NZ); Maarten L. Hertog, Scherpenheuvel (BE); Robert J. Schaffer, Auckland (NZ)

(73) Assignees: The United States of America, as represented by the Secretary of Agriculture, Washington, DC (US); Cornell University, Ithaca, NY (US); The New Zealand Institute for Plant and Food Research, Auckland (NZ); Katholieke Universiteit, Leuven (BE)

(*) Notice: Subject to any disclaimer, the term of this patent is extended or adjusted under 35 U.S.C. 154(b) by 94 days.

(21) Appl. No.: 15/069,952

(22) Filed: Mar. 14, 2016

(65) Prior Publication Data
US 2017/0260586 A1    Sep. 14, 2017

(51) Int. Cl.
| | |
|---|---|
| C07H 21/04 | (2006.01) |
| C12Q 1/68 | (2018.01) |
| C12Q 1/6883 | (2018.01) |
| G06F 19/20 | (2011.01) |
| G06F 19/22 | (2011.01) |
| G06N 5/04 | (2006.01) |
| C12Q 1/6895 | (2018.01) |
| G06F 19/18 | (2011.01) |

(52) U.S. Cl.
CPC ......... *C12Q 1/6883* (2013.01); *C12Q 1/6895* (2013.01); *G06F 19/18* (2013.01); *G06F 19/20* (2013.01); *G06F 19/22* (2013.01); *G06N 5/048* (2013.01); *C12Q 2600/118* (2013.01); *C12Q 2600/13* (2013.01); *C12Q 2600/158* (2013.01)

(58) Field of Classification Search
None
See application file for complete search history.

(56) References Cited

PUBLICATIONS

Mellidou et al. BMC Plant Biology, vol. 14, No. 328, 2014 (Year: 2014).*
Bussato et al. (BMC Plant Biology, vol. 14, No. 193, 2014) (Year: 2014).*
Larrigaudiere et al. (Scientia Horticulturae, vol. 213, pp. 340-345, 2016) (Year: 2016).*
DeEll et al. (Proc. XIIth Eucarpia Symp on Fruit Breeding, Acta Hort. 814, ISHS 2009) (Year: 2009).*
Zhang et al. (Scientific Reports, vol. 6, No. 28130, 2016) (Year: 2016).*
Array Express A-GEOD-16374-IRHS_ARyANE_v1 array from Malus domestica (see https://www.ebi.ac.uk/arrayexpress/arrays/A-GEOD-16374/?sortby=accession&sortorder=descending&page=14&pagesize=500). (Year: 2014).*
List of markers on the A-GEOD-16374-IRHS_ARyANE_v1 array from Malus domestica (see https://www.ebi.ac.uk/arrayexpress/arrays/A-GEOD-16374/?sortby=accession&sortorder=descending&page=14&pagesize=500). (Year: 2014).*
Guardo, Mario Di et al., A Multidisciplinary Approach Providing New Insight into Fruit Flesh Browning Physiology in Apple (Malus x domestica Borkh.), Plos One, (2013), 8:(10)7800.
Mellidou, Ifigeneia et al., "Transcriptomic eventsassociatedwithinternal browning ofappleduringpostharveststorage", BMC Plant Biology, (2014), 14:328.
Ogundiwin, E. A., "Leucoanthocyanidin dioxygenase gene (PpLDOX): a potential functional marker for cold storage browning in peach", Tree Genetics & Genomes, (2008), 4:543-554.
International Searching Authority, PCT/US2017/022111 for the United States of America, as Represented by the Secretary of Agriculture et al., International Filing Date Mar. 13, 2017.

(Continued)

*Primary Examiner* — Jeanine A Goldberg
(74) *Attorney, Agent, or Firm* — David L. Marks; Gail E. Poulos; John D. Fado

(57) ABSTRACT

The present invention is a tool for diagnosis and prediction using biomarker-based risk assessment for chilling-related disorders of Rosaceous fruit crops including apple and pear. Provided are methodology and genes whose relative and absolute expression can accurately indicate disorder risk throughout the production and supply chain of these crops. This technology describes a necessary and novel management tool for stakeholders producing, servicing, or retailing these crops.

1 Claim, 6 Drawing Sheets
(6 of 6 Drawing Sheet(s) Filed in Color)

(56) References Cited

PUBLICATIONS

Velasco, Riccardo et al., "The Genome of the Domesticated Apple (Malus x Domesticated Borkh)," (2010), Nature Genetics 42,(10):833-839 (26 pages Supplemental materials).

Velasco, Riccardo et al., "The Genome of the Domesticated Apple (Malus x Domesticated Borkh)," (2010), Nature Genetics 42,(10):833-839 (26 pages Supplemental materials) B.

Gapper, Nigel et al., "Biomarker Development for External CO2 Injury Prediction in Apples Through Exploration of Both Transcriptome and DNA Methylation Changes," (2013), AoB Plants 5:1-9.

Rowan, Daryl D., et al., "Conjugated Triene Oxidation Products of a-Farnesene Induce Symptoms of Superficial Scald on Stored Apples", J. Agric. Food Chem., (2001), 49:2780-2787.

Jung, S-K. et al., "Involvement of Ethylene in Browning Development of Controlled Atmosphere-Stored 'Empire' Apple Fruit," Postharvest Biology and Technology, (2011), 59:219-226.

Argenta, L.C. et al., "Response of 'Fuji' Apples to Short and Long Duration Exposure to Elevated CO2 Concentration", Postharvest Biology and Technology, (2002), 24:13-24.

Fawbush, Fanjaniaina et al., "External Carbon Dioxide Injury and 1-Methlcyclopropene (1-MCP) In the 'Empire' Apple," (2008), 48:92-98.

Watkins, C.B. et al., "Items of Interest for Storage Operators in New York and Beyond," (2002), Cornell Fruit Handling and Storage Newsletter, (2002), 1-14.

Ashburner, Michael et al., "Gene Ontology: tool for the unification of biology", (2000) Nature Genetics 25:25-29.

Gapper, Nigel E. et al., "Inhibition of ethylene-induced—famesene synthase gene PcAFS1 expression in 'd'Anjou' pears with 1-MCP reduces synthesis and oxidation of -farnesene and delays development of superficial scald", (2006) Postharvest Biology and Technology 41:225-233. Abstract only.

Lurie, Susan et al., "Superficial scald, its etiology and control", (2012) Postharvest Biology and Technology 65:44-60.

Pal, Csaba et al., "An integrated view of protein evolution", (2006) Nature Reviews Genetics 7:337-348.

Potter, D. et al., "Phylogeny and classification of Rosaceae", (2007) Plant Systematics and Evolution 226:5-43.

Stein, Lincoln, "Genome Annotation: From Sequence to Biology",(2001) Nature Reviews Genetics 2:493-503.

* cited by examiner

GENE EXPRESSION MONITORING FOR RISK ASSESSMENT OF APPLE AND PEAR FRUIT STORAGE STRESS AND PHYSIOLOGICAL DISORDERS

BACKGROUND OF THE INVENTION

Field of the Invention

The present invention is a biomarker-based risk assessment tool for predicting, diagnosing and distinguishing postharvest chilling-related physiological disorders of Rosaceous fruit crops, including apple and pear.

Background of the Invention

In the fruit industry, multiple browning disorders result in significant annual losses. A major obstacle to developing strategies that reduce such losses is the lack of methods for evaluating the risk of any of the multiple browning disorders materializing at any time during the twelve month storage and distribution period due to chilling stress imposed by the required cold storage. There have been no biomarkers identified that are useful to assess the effect of cold storage stress where the disorder is multifactorial and where the outcome will not become evident for many months. The risk is difficult to determine as existing tests aimed at estimating fruit quality are not linked with conditions associated with browning disorder risk. Thus, there is currently a need to develop more effective techniques for identification of endpoints for monitoring disorder progression during the storage and the distribution period and for evaluating the effectiveness of changes instituted in efforts to treat and control such disorders. To date, no consistently effective risk assessment exists targeting postharvest disorders and control measures are even lacking for many prevalent browning disorders.

SUMMARY OF THE INVENTION

We have identified biomarkers that predict, diagnose, and distinguish multiple postharvest browning disorders during the cold storage period, thereby enabling a strategy for assessing risk for the occurrence of multiple browning disorders throughout the cold storage and distribution periods and for adjusting controls and marketing strategies to reduce product loss.

In accordance with this discovery, it is an object of the invention to provide a method of using biomarkers to identify stages of the progression of the multiple browning disorders soft scald, soggy breakdown, firm flesh browning, external $CO_2$ injury and superficial scald during the cold storage period as part of a strategy of risk assessment in order to facilitate storage and supply chain management decisions.

It is an object of the invention to provide measurable metabolites and identified biomarkers (expressed gene sequences reflecting mRNA changes) that can be monitored to assess risk of storage disorder development as changes in levels of multiple expressed genes precede browning disorder development by weeks or months.

It is a further object of the invention to provide biomarker profiles whose relative and absolute expression can accurately predict and diagnose disorder risk throughout the production and supply chain of these crops.

It is another object of the invention to monitor biomarker levels in apple and pear tissues throughout the entire growing and supply chain as a means to predict and diagnose and assess risk for disorder development, to check effectiveness of control strategies, and to adjust disorder control or marketing strategies in order to avoid losses and thereby provide a more consistent, high quality product to consumers.

It is an additional object of the invention to provide a biomarker-based diagnostic tool as a necessary and novel management tool for stakeholders producing, servicing, or retailing these crops.

It is an additional object of the invention to provide such monitoring strategies in order to provide effective treatment and control practices that can be monitored by reliance on the same biomarkers as indicators of their effect on maintenance of fruit quality with the result that previously employed crop protectant applications or energy input into the storage environment are no longer necessary.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

DETAILED DESCRIPTION OF THE INVENTION

Figure 1A:
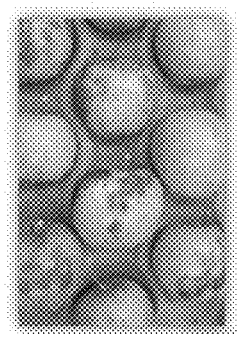
FIGS. 1A-1E depict examples of chilling-related postharvest physiological disorders of apple. These disorders are physiologically and etiologically distinct. Superficial scald (FIG. 1A) and firm flesh browning (FIG. 1B) were chosen to discover risk assessment biomarkers for late-term disorders; soft scald (FIG. 1C), soggy breakdown (FIG. 1D), and $CO_2$ injury (FIG. 1E) for early term disorders.
Figure 1B:
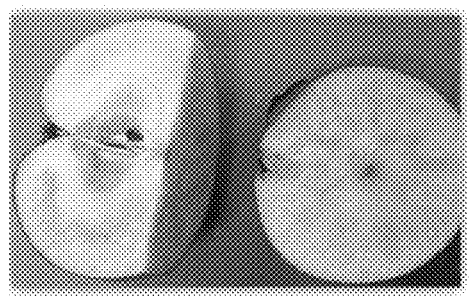
Figure 1C:
Figure 1D:
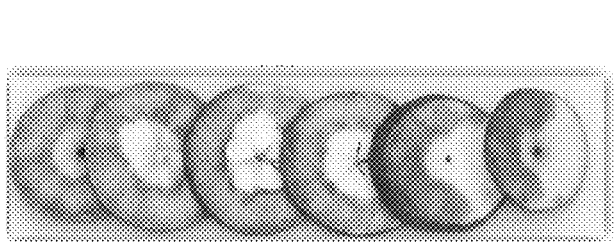
Figure 1E:
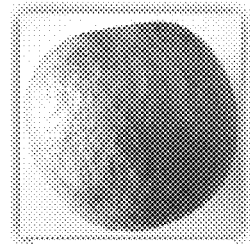

Multiple browning disorders that lead to severe damage of the peel and cortex (FIG. 1) are a major problem in the fruit industry, causing low quality, inconsistent fruit products for the consumer and severe annual losses. Costs for protectants and additional energy costs also add to these losses. We have applied metabolic and gene expression profiling to discover biomarkers that can be used to predict, diagnose, and distinguish economically significant apple postharvest physiological disorders. Changes in levels of multiple expressed genes precede disorder development by weeks or months. The invention reduces product loss caused by multiple browning disorders by indicating which fruit have a high risk for developing the disorders and therefore can serve as a basis for storage and supply chain management decisions. We have identified metabolites and biomarkers (gene sequences reflecting mRNA changes) that can be monitored and used to assess risk of storage disorder development. These identified genes have not been previously associated with fruit chilling stress in Rosaceous crops. Further, these identified genes are very similar among Rosaceous fruit crops. Fruit response to stress events that lead to these collective disorders are detected and monitored using this approach. Unlike previous technologies, this invention targets storage risk assessment and only incorporates differences in fruit quality factors or fruit ripeness or maturity when these conditions impact disorder development. Monitoring biomarker levels in apple and pear tissues throughout the entire growing and supply chain provides a means to check effectiveness of control strategies, diagnose and assess risk for disorder development and, then, adjust disorder control or marketing strategies to avoid losses and provide a more consistent, high quality, disorder-free product to consumers. Integrated production approaches using this new tool potentially reduce unnecessary crop protectant application or energy input into the storage environment by reducing uncertainty of effectiveness of technologies presently in use.

Expression of risk assessment genes and metabolites levels are evaluated at key decision points from before harvest until the end of the supply chain. mRNA samples are extracted from peel or cortex tissue and the extract prepared depending upon the evaluation method to be employed. Expression levels of the given gene sequences can be monitored using RNAseq Solexa protocols (Solexa, Illumina, Hayward, Calif.). Expression levels are considered absolutely, depending upon the platform employed, and/or relatively, regardless of the platform and may be negatively or positively associated with disorder risk. Expression levels are considered in the context of mitigating conditions and stresses applied during the production chain and alongside levels of metabolites that less accurately indicate elevated risk for certain disorders.

Softscald and soggy breakdown (FIGS. 1C and 1D) are related but distinct disorders associated with low temperature storage. Soft scald symptoms are sharply defined brown lesions on the apple skin which can extend into the flesh (Snowdon, A. L. 1990. A Color Atlas of Post-harvest Diseases and Disorders of Fruits and Vegetables, Vol. 1. CRC Press, Boca Raton, Fla., 213 pp.; Watkins and Rosenberger. 2002. Cornell Fruit Handling and Storage Newsletter, 14pp. [Retrieved from the internet: hort.cornell. edu/department/faculty/Watkins/extpubs.] while soggy breakdown is an internal disorder with soft, brown, sponge-like tissue, sometimes including most of the flesh (Watkins and Rosenberger, supra). Softscald and soggy breakdown are early-term severe chilling-provoked browning disorders of apple and pear peel and cortical tissue impacting multiple economically significant cultivars including 'Honeycrisp' and Jazz™. Typically symptoms appear following 0-2 months following cold storage imposition. Tests and validation of the biomarkers considered seasonal variation and multiple climatic, orchard, developmental, crop protectant, and storage factors employed using common industry practices. Risk assessment was performed at harvest and within 1-2 weeks following cold storage imposition. Evaluating risk assessment biomarker gene expression levels (Tables 1 and 2) provided an early, accurate assessment of disorder risk in these cultivars up to 4 weeks prior to symptom appearance. Comparing relative levels before and after cold storage imposition and/or among expressed biomarkers provided additional confidence in the assessment.

$CO_2$ injury is exhibited externally and/or internally depending on the cultivar and growing conditions (Colgan et al. 1999. *Postharvest Biol. Technol.* 16:223-231; Elgar et al. 1998. *Hortsci.* 33:719-722; Elgar et al. 1999. *Hortsci.* 34:305-309; Fernandez-Trujillo et al. 2001. *J. Amer. Soc. Hort. Sci.* 126:235-241; Watkins et al. 1997. *HortScience* 32:1242-1246). Susceptible cultivars include 'Braeburn', 'Cortland', 'Empire', 'Fuji', 'Golden Delicious', 'Honeycrisp', and 'McIntosh'. Diphenylamine (DPA) reduces or prevents development of both external and internal $CO_2$ injury and, when DPA is not used, significant losses result (Argenta et al. 2002. *Postharvest Biol. Technol.* 24:13-24; Burmeister and Dilley.1995. *Postharvest Biol. Technol.* 6:1-7; Colgan et al. 1999, supra; Fernandez-Trujillo et al., supra). Unlike superficial scald, 1-methylcyclopropene (1-MCP) treatment exacerbates $CO_2$ injury (Fawbush et al. 2008. *Postharvest Biol. Technol.* 48:92-98). $CO_2$ injury has been associated with accumulation of succinate in the tissue of fruit exposed to high $CO_2$ concentrations (Hulme, A. C. 1956. *Nature* 178:218-219), but Fernandez-Trujillo et al. (supra) found similar levels of succinate in injured controls and non-injured fruit treated with DPA. Risk assessment biomarker gene expression levels (Table 3) change with disorder risk following cold storage inception caused by chilling and elevated $CO_2$ and mitigated by crop protectant and other orchard and storage factors.

Superficial scald is a late-term chilling-related peel browning disorder of multiple apple and pear cultivars; typically symptoms appear after at least 2 months cold storage (FIG. 3A) (Bain and Mercer. 1963. *Aust. J. Biol. Sci.* 16:442-449). Superficial scald is associated with oxidative stress ostensibly linked to the build-up of oxidation products of the sesquiterpene (E,E)-α-farnesene (Huelin and Coggiola. 1970. *J. Sci. Food Agric.* 21:584-589; Whitaker et al. 2000. *Postharvest Biol. Technol.* 20:231-241; Rowan et al. 2001. *J. Agri. Food Chem.* 49:2780-2787). Pre-storage treatment of apples with DPA inhibits oxidation of α-farnesene and largely prevents scald development (Huelin and Coggiola, supra). Moreover, exposure of apple fruit to the ethylene action inhibitor 1-MCP greatly curtails α-farnesene production and markedly reduces scald incidence and severity (Fan et al. 1999. *J. Agri. Food Chem.* 47:3063-3068;

Rupasinghe et al. 2000. *J. Hort. Sci. Biotech.* 75:271-276; Watkins et al. 2000. *Postharvest Biol. Technol.* 19:17-32; Shaham et al. 2003. *J. Am. Soc. Hort. Sci.* 128:761-766). Controlled atmosphere storage (low oxygen) can reduce scald incidence and severity (Fidler et al. 1973. In: *Commonwealth Agricultural Bureaux*, England. Pp. 113-116; Lau, O. L. 1990. *J. Am. Soc. Hortic. Sci.* 115:959-961), but not consistently if risk is high. Symptoms of this disorder typically appear from 4 to 6 months after cold storage imposition and can be controlled during conventional production using multiple approaches and during organic production using controlled atmosphere storage. However, reduced acceptance of antioxidant crop protectants used to control superficial scald and inconsistent efficacy of control using controlled atmosphere storage assures that this disorder remains a significant annual economic world-wide consideration for producers of susceptible apple and pear cultivars, including 'Granny Smith' and 'Delicious'. Risk assessment biomarker gene expression levels were different at harvest (Table 4) depending upon the risk of apples from individual orchards to develop the disorder. Other biomarkers (Table 5) increased dramatically during storage starting at 3 months prior to first symptom appearance in 'Granny Smith' apples, providing an early and accurate risk assessment of conditions evoked by production, crop protectant and storage conditions. Monitoring relative biomarker gene expression levels alongside oxidation of superficial scald-associated metabolites, such as α-farnesene and methanol, can improve assessment accuracy using this technology.

Firm flesh browning is considered a form of chilling injury that results in patterned darkening of the flesh. It is a long term problem of the 'Empire' cultivar. 'Empire' is considered highly desirable by the fresh cut apple industry and flesh browning is unacceptable. Increasing storage temperatures from 0° C. to 2° C. reduces the symptoms although unacceptable softening occurs at 3° C. 1-MCP treatment is now the industry norm to meet market requirements, but 1-MCP-treated fruit develop flesh browning at both low and high storage temperatures (Jung et al. 2011. *Postharvest Biol. Technol.* 59:219-226). DPA and other treatments that control flesh browning are ineffective in 1-MCP-treated fruit. These flesh browning symptoms are visually indistinguishable from those previously considered to be chilling injury. Risk assessment biomarker gene expression levels (Table 6) change with the risk of occurrence of the disorder following cold storage inception caused by chilling and mitigated by crop protectant and other orchard and storage factors.

Experimental evidence supports that expression levels of these risk assessment biomarkers change similarly with stresses that can lead to multiple early and late storage term disorders. Biomarker expression does not correlate with any traditional quality-associated phenotype such as firmness or flavor loss. Instead, biomarker expression specifically represents changes with stress and storage factors that lead to browning disorder development.

Apple [*Malus sylvestris* (L.) Mill var. *domestica* (Borkh.) Mansf.] was chosen as the model for discovering biomarkers for Rosaceous fruit postharvest browning disorders as different apple cultivars are susceptible to developing many distinct postharvest browning disorders of the peel and flesh, and our understanding of the controls and etiology of these disorders is best in apples. There is a high degree of gene homology among Rosaceous fruit crops, including pear. This and ripening and postharvest physiological similarities make risk assessment biomarkers behave similarly under high or low risk conditions.

The present invention provides improved systems and strategies for predicting the progression of multiple browning disorders. According to the present invention, soft scald, soggy breakdown, superficial scald, firm flesh browning and $CO_2$ injury of Rosaceous fruit may be predicted or diagnosed by obtaining a profile of biomarkers from a sample obtained from Rosaceous fruit tissue. The present invention is particularly useful for predicting and diagnosing soft scald, soggy breakdown, superficial scald, firm flesh browning and $CO_2$ injury during storage and distribution.

Biomarker profiles may be a ratio of two or more measurable aspects of a biomarker. A biomarker profile comprises at least one measurement, where the measurements can correspond to the same or different biomarkers. A biomarker profile may also comprise at least three, four, five, 10, 20, 30 or more measurements. The profile of biomarkers obtained from an individual apple tissue specimen, namely the candidate biomarker profile, is compared to a reference biomarker profile. The reference biomarker profile can be generated from one individual or a population of individuals at different time points during storage.

The reference biomarker profile and the candidate biomarker profiles that are compared in the methods of the present invention may be generated from the same population for the purpose of monitoring disorder progression. In this instance it would be expected that the candidate and reference profiles are generated from biological samples taken at different time points and compared to one another, i.e., the reference profile will be expression of the biomarker at the earlier time point and compared to the candidate's biomarker expression at the later time point. Such a comparison may be used, for example, to determine the risk status of developing a browning disorder in the individual tissue by repeated measurements over time. The reference biomarker profiles may be chosen from tissue of fruit that has a risk of a browning disorder or the reference biomarker profile may be generated from a healthy individual or population that is not at risk, i.e., those that are in a non-affected environment, in a controlled storage population, or in an environmental crop protected situation. In addition, it would be expected that the candidate and reference profiles are generated from biological samples taken from different orchard locations, reflecting environmental and disorder development differences, and compared to one another. i.e., the reference profile will be expression of the biomarker from a sample with known disorder development and compared to the candidates biomarker expression from another population.

The methods of the present invention comprise comparing a candidate biomarker profile with a reference biomarker profile. The present invention is based on the identification of new biomarkers of multiple browning disorders. A biomarker is useful if it is specific for a browning disorder and measurable. In particular, of the 63,541 genes screened for assessing risk for soft scald and soggy breakdown and $CO_2$ injury, the present invention provides the identity of 82 candidates found useful for assessing risk at-harvest (Table 1) and 494 for 2 week risk assessment of peel and/or cortex tissue (Table 2). Accordingly, in one aspect, the present invention provides for the identification, generation, and use of expression profiles of sets of genes selected from the genes disclosed herein.

TABLE 1

Accession numbers (Velasco et al., 2010; Retrieved from the Internet: Rosaceae.org) of biomarker genes for soft scald assessment at harvest. Elevated expression levels indicate orchards with a higher risk for developing these disorders.

| | | | | |
|---|---|---|---|---|
| MDP0000848515 | MDP0000238780 | MDP0000260007 | MDP0000153149 | MDP0000585315 |
| MDP0000273646 | MDP0000216786 | MDP0000180580 | MDP0000737425 | MDP0000298967 |
| MDP0000808492 | MDP0000273866 | MDP0000353053 | MDP0000910032 | MDP0000145050 |
| MDP0000263844 | MDP0000158999 | MDP0000547254 | MDP0000196325 | MDP0000224653 |
| MDP0000321382 | MDP0000270602 | MDP0000233661 | MDP0000665342 | MDP0000246831 |
| MDP0000823528 | MDP0000408705 | MDP0000518327 | MDP0000291249 | MDP0000154589 |
| MDP0000202817 | MDP0000590954 | MDP0000312397 | MDP0000213383 | MDP0000529726 |
| MDP0000312071 | MDP0000639894 | MDP0000307665 | MDP0000183676 | MDP0000754521 |
| MDP0000797616 | MDP0000818877 | MDP0000782908 | MDP0000266443 | MDP0000562305 |
| MDP0000228366 | MDP0000361351 | MDP0000737001 | MDP0000412192 | MDP0000223032 |
| MDP0000149492 | MDP0000264361 | MDP0000125882 | MDP0000498460 | MDP0000163006 |
| MDP0000225132 | MDP0000329063 | MDP0000170865 | MDP0000665685 | MDP0000196079 |
| MDP0000200783 | MDP0000182956 | MDP0000862371 | MDP0000321792 | MDP0000441757 |
| MDP0000313657 | MDP0000599531 | MDP0000297583 | MDP0000272980 | MDP0000317502 |
| MDP0000268175 | MDP0000722139 | MDP0000637194 | MDP0000125700 | MDP0000287262 |
| MDP0000745534 | MDP0000164966 | MDP0000389794 | MDP0000318068 | MDP0000322237 |
| MDP0000225326 | MDP0000125411 | | | |

TABLE 2

Accession numbers (Velasco et al., 2010; Retrieved from the Internet: Rosaceae.org) of biomarker genes for soft scald assessment during cold storage following cold storage imposition. Higher or lower expression levels can result from cold stress resulting from storage imposition. Where lower expression is associated with risk, accession numbers are italicized.

| | | | | | | |
|---|---|---|---|---|---|---|
| *MDP0000675982* | *MDP0000202163* | *MDP0000219532* | *MDP0000568913* | *MDP0000313850* | *MDP0000391472* | *MDP0000273608* |
| *MDP0000727481* | *MDP0000244038* | *MDP0000131371* | *MDP0000133673* | *MDP0000225088* | *MDP0000143677* | *MDP0000150382* |
| *MDP0000286751* | *MDP0000272528* | *MDP0000312509* | *MDP0000173235* | *MDP0000282119* | *MDP0000172451* | *MDP0000846736* |
| *MDP0000818940* | *MDP0000320691* | *MDP0000434271* | *MDP0000231298* | *MDP0000263282* | *MDP0000910523* | *MDP0000203897* |
| *MDP0000276370* | *MDP0000270427* | *MDP0000281525* | *MDP0000150953* | *MDP0000124552* | *MDP0000446865* | *MDP0000122897* |
| *MDP0000287631* | *MDP0000463638* | *MDP0000215630* | *MDP0000252369* | *MDP0000124552* | *MDP0000283534* | *MDP0000259550* |
| *MDP0000385730* | *MDP0000156937* | *MDP0000250658* | *MDP0000252854* | *MDP0000031172* | *MDP0000226432* | *MDP0000230300* |
| *MDP0000179388* | *MDP0000618810* | *MDP0000167107* | *MDP0000415894* | *MDP0000467552* | *MDP0000249564* | *MDP0000632679* |
| *MDP0000146003* | *MDP0000154360* | *MDP0000252590* | *MDP0000698038* | *MDP0000119629* | *MDP0000250546* | *MDP0000220511* |
| *MDP0000314632* | *MDP0000758778* | *MDP0000376256* | *MDP0000320586* | *MDP0000336518* | *MDP0000181779* | *MDP0000204836* |
| *MDP0000560122* | *MDP0000157644* | *MDP0000376284* | *MDP0000156837* | *MDP0000242656* | *MDP0000175375* | *MDP0000203543* |
| *MDP0000944409* | *MDP0000577872* | *MDP0000325574* | *MDP0000146856* | *MDP0000179760* | *MDP0000376469* | *MDP0000273646* |
| *MDP0000300382* | *MDP0000945035* | *MDP0000171928* | *MDP0000399796* | *MDP0000121410* | *MDP0000481590* | *MDP0000176602* |
| *MDP0000717305* | *MDP0000124013* | *MDP0000603942* | *MDP0000858559* | *MDP0000298286* | *MDP0000208533* | *MDP0000135436* |
| *MDP0000944724* | *MDP0000129143* | *MDP0000165921* | *MDP0000235661* | *MDP0000181572* | *MDP0000121476* | *MDP0000466420* |
| *MDP0000152960* | *MDP0000306385* | *MDP0000804078* | *MDP0000568045* | *MDP0000703874* | *MDP0000153251* | *MDP0000206763* |
| *MDP0000133675* | *MDP0000240921* | *MDP0000159957* | *MDP0000178319* | *MDP0000270308* | *MDP0000707440* | *MDP0000171170* |
| *MDP0000621193* | *MDP0000473467* | *MDP0000221993* | *MDP0000178319* | *MDP0000269788* | *MDP0000273634* | *MDP0000940411* |
| *MDP0000533216* | *MDP0000326288* | *MDP0000293351* | *MDP0000727431* | *MDP0000162628* | *MDP0000278681* | *MDP0000452125* |
| *MDP0000310493* | *MDP0000187246* | *MDP0000843691* | *MDP0000257928* | *MDP0000462161* | *MDP0000121588* | *MDP0000167303* |
| *MDP0000302680* | *MDP0000276235* | *MDP0000828513* | *MDP0000585111* | *MDP0000203765* | *MDP0000610961* | *MDP0000233110* |
| *MDP0000135249* | *MDP0000201499* | *MDP0000231242* | *MDP0000499186* | *MDP0000306861* | *MDP0000912405* | *MDP0000886138* |
| *MDP0000252890* | *MDP0000221238* | *MDP0000504185* | *MDP0000911051* | *MDP0000243083* | *MDP0000932845* | *MDP0000302461* |
| *MDP0000177861* | *MDP0000142824* | *MDP0000148780* | *MDP0000145104* | *MDP0000172709* | *MDP0000058337* | *MDP0000209944* |
| *MDP0000131979* | *MDP0000222188* | *MDP0000321057* | *MDP0000124296* | *MDP0000166657* | *MDP0000132990* | *MDP0000770103* |
| *MDP0000206752* | *MDP0000319743* | *MDP0000725469* | *MDP0000253047* | *MDP0000734582* | *MDP0000867280* | *MDP0000211758* |
| *MDP0000466766* | *MDP0000280643* | *MDP0000469943* | *MDP0000137428* | *MDP0000312022* | *MDP0000233037* | *MDP0000922120* |
| *MDP0000250234* | *MDP0000279287* | *MDP0000218935* | *MDP0000224592* | *MDP0000610962* | *MDP0000389181* | *MDP0000275383* |
| *MDP0000143460* | *MDP0000858039* | *MDP0000129164* | *MDP0000188710* | *MDP0000241574* | *MDP0000933329* | *MDP0000119002* |
| *MDP0000455477* | *MDP0000313699* | *MDP0000217734* | *MDP0000163618* | *MDP0000202280* | *MDP0000403071* | |
| *MDP0000193127* | *MDP0000178268* | *MDP0000322647* | *MDP0000046192* | *MDP0000227830* | *MDP0000192562* | *MDP0000158194* |
| *MDP0000219538* | *MDP0000169311* | *MDP0000204345* | *MDP0000607654* | *MDP0000274300* | *MDP0000730019* | *MDP0000121241* |
| *MDP0000145382* | *MDP0000174168* | *MDP0000228473* | *MDP0000296179* | *MDP0000120959* | *MDP0000182571* | *MDP0000214069* |
| *MDP0000620250* | *MDP0000168262* | *MDP0000163588* | *MDP0000564193* | *MDP0000172879* | *MDP0000285670* | *MDP0000765891* |
| *MDP0000613170* | *MDP0000755889* | *MDP0000182716* | *MDP0000282431* | *MDP0000220454* | *MDP0000423589* | *MDP0000276057* |
| *MDP0000234570* | *MDP0000920069* | *MDP0000284699* | *MDP0000239301* | *MDP0000873667* | *MDP0000159246* | *MDP0000896590* |
| *MDP0000204345* | *MDP0000137477* | *MDP0000180064* | *MDP0000766844* | *MDP0000364275* | *MDP0000632640* | *MDP0000126141* |
| *MDP0000228830* | *MDP0000757787* | *MDP0000319787* | *MDP0000202326* | *MDP0000417786* | *MDP0000145543* | *MDP0000228367* |
| *MDP0000799392* | *MDP0000545323* | *MDP0000639185* | *MDP0000192979* | *MDP0000239892* | *MDP0000883220* | *MDP0000181133* |
| *MDP0000758645* | *MDP0000187438* | *MDP0000305324* | *MDP0000641838* | *MDP0000126259* | *MDP0000252726* | *MDP0000225382* |
| MDP0000873376 | MDP0000197455 | MDP0000744636 | MDP0000569149 | MDP0000364750 | MDP0000175173 | |
| MDP0000263877 | MDP0000247311 | MDP0000274039 | MDP0000196325 | MDP0000799187 | MDP0000552895 | |
| MDP0000225340 | MDP0000267416 | MDP0000461015 | MDP0000196325 | MDP0000235688 | MDP0000398415 | |
| MDP0000223153 | MDP0000176129 | MDP0000255115 | MDP0000733239 | MDP0000163728 | MDP0000385086 | |
| MDP0000295340 | MDP0000223514 | MDP0000296708 | MDP0000488588 | MDP0000803726 | MDP0000273470 | |
| MDP0000134259 | MDP0000308205 | MDP0000754298 | MDP0000298491 | MDP0000797360 | MDP0000270759 | |
| MDP0000191432 | MDP0000293437 | MDP0000489156 | MDP0000400262 | MDP0000140569 | MDP0000221844 | |

TABLE 2-continued

Accession numbers (Velasco et al., 2010; Retrieved from the Internet: Rosaceae.org) of biomarker genes for soft scald assessment during cold storage following cold storage imposition. Higher or lower expression levels can result from cold stress resulting from storage imposition. Where lower expression is associated with risk, accession numbers are italicized.

| | | | | | |
|---|---|---|---|---|---|
| MDP0000225867 | MDP0000310803 | MDP0000284374 | MDP0000303924 | MDP0000724726 | MDP0000228064 |
| MDP0000646125 | MDP0000709073 | MDP0000122895 | MDP0000392540 | MDP0000128265 | MDP0000315323 |
| MDP0000279149 | MDP0000243428 | MDP0000319512 | MDP0000524677 | MDP0000287199 | MDP0000157932 |
| MDP0000163088 | MDP0000686661 | MDP0000637142 | MDP0000136933 | MDP0000642530 | MDP0000467241 |
| MDP0000204212 | MDP0000231619 | MDP0000207937 | MDP0000065186 | MDP0000120398 | MDP0000873235 |
| MDP0000271479 | MDP0000138275 | MDP0000236176 | MDP0000360077 | MDP0000161521 | MDP0000168076 |
| MDP0000891353 | MDP0000314606 | MDP0000232589 | MDP0000277370 | MDP0000239442 | MDP0000124881 |
| MDP0000262367 | MDP0000249502 | MDP0000520097 | MDP0000870230 | MDP0000917844 | |
| MDP0000165325 | MDP0000156727 | MDP0000216267 | MDP0000506697 | MDP0000212628 | |
| MDP0000215235 | MDP0000139194 | MDP0000194823 | MDP0000264406 | MDP0000298280 | |
| MDP0000561738 | MDP0000274685 | MDP0000940086 | MDP0000889787 | MDP0000368098 | |
| MDP0000273126 | MDP0000244593 | MDP0000342041 | MDP0000916486 | MDP0000563592 | |
| MDP0000879217 | MDP0000170568 | MDP0000196064 | MDP0000898951 | MDP0000234503 | |
| MDP0000249248 | MDP0000219876 | MDP0000169170 | MDP0000873427 | MDP0000130994 | |
| MDP0000226838 | MDP0000249858 | MDP0000321157 | MDP0000294840 | MDP0000775468 | |
| MDP0000188052 | MDP0000211229 | MDP0000131731 | MDP0000216027 | MDP0000153185 | |
| MDP0000156246 | MDP0000319315 | MDP0000150429 | MDP0000150710 | MDP0000263844 | |
| MDP0000842137 | MDP0000260116 | MDP0000260377 | MDP0000214906 | MDP0000121783 | |
| MDP0000174971 | MDP0000898232 | MDP0000447975 | MDP0000120330 | MDP0000252488 | |
| MDP0000151767 | MDP0000453114 | MDP0000320239 | MDP0000127732 | MDP0000547788 | |
| MDP0000279576 | MDP0000725984 | MDP0000253102 | MDP0000418187 | MDP0000220129 | |
| MDP0000651801 | MDP0000277459 | MDP0000787701 | MDP0000147201 | MDP0000222196 | |
| MDP0000188054 | MDP0000307795 | MDP0000234782 | MDP0000146449 | MDP0000719275 | |
| MDP0000757641 | MDP0000193241 | MDP0000131486 | MDP0000903417 | MDP0000143473 | |
| MDP0000165187 | MDP0000160077 | MDP0000272522 | MDP0000273225 | MDP0000197624 | |
| MDP0000590974 | MDP0000297123 | MDP0000268258 | MDP0000121830 | MDP0000564318 | |
| MDP0000014856 | MDP0000791166 | MDP0000197330 | MDP0000151362 | MDP0000280632 | |
| MDP0000198015 | MDP0000710467 | MDP0000250386 | MDP0000151457 | MDP0000166159 | |
| MDP0000356821 | MDP0000222944 | MDP0000363287 | MDP0000421679 | MDP0000418062 | |
| MDP0000762756 | MDP0000321469 | MDP0000242205 | MDP0000279018 | MDP0000641544 | |
| MDP0000311618 | MDP0000681634 | MDP0000272640 | MDP0000152774 | MDP0000719559 | |
| MDP0000178043 | MDP0000500159 | MDP0000920394 | MDP0000294531 | MDP0000139291 | |
| MDP0000312998 | MDP0000154049 | MDP0000230727 | MDP0000941000 | MDP0000804427 | |

Because superficial scald can be adequately controlled using appropriate storage conditions, indicating whether storage conditions are actually working or monitoring risk during storage is also a useful tool for this disorder.

External $CO_2$ injury browning disorder can be controlled using application of commercially used postharvest chemicals. We were able to use these methods to discover putative biomarkers, as different treatments following harvest induce contrasting disorder development. Controlled atmosphere combined with treatment of apples with 1-MCP (Smart-Fresh) following harvest enhances external $CO_2$ injury. In contrast postharvest treatment with the antioxidant diphenylamine (DPA) almost eliminates external $CO_2$ injury completely. Candidate biomarker genes from an RNAseq experiment were selected by pairwise comparison using the differential gene expression program edgeR (R, Bioconductor) with a p-value cut off of 0.05. Genes were selected and peel tissue collected from New York state grown 'Empire' apples, provoked by storage treatments that affect external $CO_2$ injury incidence. From a total of 63541 gene models, 2330 that expression changed at least 4-fold and that had an average expression RPKM value of at least 1 per sample were selected as potential predictive or diagnostic biomarkers for external $CO_2$ injury (Table 3).

TABLE 3

Accession numbers (Velasco et al., 2010; Retrieved from the Internet: Rosaceae.org) of biomarker genes for $CO_2$ injury assessment during cold storage following cold storage imposition. Higher or lower expression levels can result from cold stress resulting from storage imposition.

| | | | | | | |
|---|---|---|---|---|---|---|
| MDP0000840536 | MDP0000708692 | MDP0000349942 | MDP0000261740 | MDP0000863792 | MDP0000140151 | MDP0000252752 |
| MDP0000661951 | MDP0000357718 | MDP0000590966 | MDP0000565270 | MDP0000148686 | MDP0000435842 | MDP0000400084 |
| MDP0000745805 | MDP0000716794 | MDP0000126361 | MDP0000233319 | MDP0000573540 | MDP0000135191 | MDP0000414314 |
| MDP0000940411 | MDP0000152673 | MDP0000809337 | MDP0000432471 | MDP0000127630 | MDP0000310700 | MDP0000321031 |
| MDP0000794258 | MDP0000251180 | MDP0000697676 | MDP0000461015 | MDP0000130797 | MDP0000310582 | MDP0000184143 |
| MDP0000769492 | MDP0000642253 | MDP0000245702 | MDP0000300161 | MDP0000160197 | MDP0000167683 | MDP0000251957 |
| MDP0000769493 | MDP0000202184 | MDP0000844682 | MDP0000283288 | MDP0000330474 | MDP0000298689 | MDP0000232865 |
| MDP0000200896 | MDP0000649783 | MDP0000496027 | MDP0000168735 | MDP0000295392 | MDP0000126481 | MDP0000228366 |
| MDP0000755567 | MDP0000260404 | MDP0000192733 | MDP0000131763 | MDP0000501957 | MDP0000172296 | MDP0000180012 |
| MDP0000564079 | MDP0000120347 | MDP0000769764 | MDP0000321302 | MDP0000238081 | MDP0000607920 | MDP0000273201 |
| MDP0000348107 | MDP0000231748 | MDP0000350778 | MDP0000835211 | MDP0000926304 | MDP0000202781 | MDP0000164134 |
| MDP0000864747 | MDP0000309314 | MDP0000274714 | MDP0000374881 | MDP0000140878 | MDP0000695737 | MDP0000531811 |
| MDP0000637737 | MDP0000585462 | MDP0000897962 | MDP0000294677 | MDP0000205306 | MDP0000232535 | MDP0000616079 |
| MDP0000575740 | MDP0000334047 | MDP0000158089 | MDP0000316698 | MDP0000122792 | MDP0000225088 | MDP0000262337 |
| MDP0000899351 | MDP0000568045 | MDP0000814899 | MDP0000297123 | MDP0000162529 | MDP0000145449 | MDP0000121243 |

TABLE 3-continued

Accession numbers (Velasco et al., 2010; Retrieved from the Internet: Rosaceae.org) of biomarker genes for $CO_2$ injury assessment during cold storage following cold storage imposition. Higher or lower expression levels can result from cold stress resulting from storage imposition.

| | | | | | | | |
|---|---|---|---|---|---|---|---|
| MDP0000836784 | MDP0000703737 | MDP0000163032 | MDP0000175918 | MDP0000728167 | MDP0000780353 | MDP0000153630 | |
| MDP0000258775 | MDP0000270052 | MDP0000292031 | MDP0000811831 | MDP0000193401 | MDP0000145401 | MDP0000264666 | |
| MDP0000128562 | MDP0000218910 | MDP0000164159 | MDP0000257243 | MDP0000584042 | MDP0000184567 | | |
| MDP0000300836 | MDP0000270727 | MDP0000199022 | MDP0000257423 | MDP0000245234 | MDP0000143312 | MDP0000230950 | |
| MDP0000195885 | MDP0000175169 | MDP0000819881 | MDP0000292266 | MDP0000287234 | MDP0000278762 | MDP0000315857 | |
| MDP0000139058 | MDP0000906293 | MDP0000139113 | MDP0000131377 | MDP0000121656 | MDP0000243935 | MDP0000513880 | |
| MDP0000668095 | MDP0000811129 | MDP0000151884 | MDP0000174273 | MDP0000302905 | MDP0000340590 | MDP0000216937 | |
| MDP0000175691 | MDP0000554377 | MDP0000235569 | MDP0000149492 | MDP0000515505 | MDP0000625754 | MDP0000289999 | |
| MDP0000318069 | MDP0000936075 | MDP0000289026 | MDP0000225132 | MDP0000188790 | MDP0000273963 | MDP0000250047 | |
| MDP0000911067 | MDP0000750914 | MDP0000283036 | MDP0000609114 | MDP0000139609 | MDP0000151152 | MDP0000250547 | |
| MDP0000185723 | MDP0000120398 | MDP0000208739 | MDP0000165172 | MDP0000136104 | MDP0000166477 | MDP0000149146 | |
| MDP0000144125 | MDP0000161521 | MDP0000212760 | MDP0000925058 | MDP0000914171 | MDP0000267956 | MDP0000217146 | |
| MDP0000491512 | MDP0000125631 | MDP0000934638 | MDP0000899071 | MDP0000456521 | MDP0000206902 | MDP0000656707 | |
| MDP0000216907 | MDP0000393617 | MDP0000539956 | MDP0000273759 | MDP0000773525 | MDP0000176185 | MDP0000205727 | |
| MDP0000295542 | MDP0000160662 | MDP0000194046 | MDP0000553140 | MDP0000795356 | MDP0000773851 | MDP0000219415 | |
| MDP0000440922 | MDP0000219737 | MDP0000872868 | MDP0000153375 | MDP0000244335 | MDP0000167207 | MDP0000628470 | |
| MDP0000287302 | MDP0000165830 | MDP0000909081 | MDP0000301787 | MDP0000256960 | MDP0000121815 | MDP0000801340 | |
| MDP0000471879 | MDP0000297197 | MDP0000518858 | MDP0000285427 | MDP0000282119 | MDP0000281791 | MDP0000684928 | |
| MDP0000203930 | MDP0000137441 | MDP0000416548 | MDP0000269872 | MDP0000319795 | MDP0000155229 | MDP0000203128 | |
| MDP0000843913 | MDP0000813278 | MDP0000209432 | MDP0000821066 | MDP0000230682 | MDP0000437672 | MDP0000135865 | |
| MDP0000214714 | MDP0000298230 | MDP0000123467 | MDP0000320589 | MDP0000279576 | MDP0000790420 | MDP0000199390 | |
| MDP0000686661 | MDP0000191457 | MDP0000771693 | MDP0000137929 | MDP0000455634 | MDP0000742797 | MDP0000299682 | |
| MDP0000122086 | MDP0000382336 | MDP0000188275 | MDP0000657944 | MDP0000435717 | MDP0000220458 | MDP0000293343 | |
| MDP0000216662 | MDP0000430367 | MDP0000140394 | MDP0000302780 | MDP0000606470 | MDP0000272179 | MDP0000214380 | |
| MDP0000144836 | MDP0000411498 | MDP0000299114 | MDP0000129505 | MDP0000119032 | MDP0000245553 | MDP0000300969 | |
| MDP0000128924 | MDP0000184324 | MDP0000327390 | MDP0000256650 | MDP0000124197 | MDP0000280508 | MDP0000701552 | |
| MDP0000172234 | MDP0000255705 | MDP0000419297 | MDP0000336281 | MDP0000210484 | MDP0000143660 | MDP0000221346 | |
| MDP0000941000 | MDP0000235028 | MDP0000146360 | MDP0000255115 | MDP0000212239 | MDP0000124626 | MDP0000125038 | |
| MDP0000162215 | MDP0000224489 | MDP0000371737 | MDP0000254260 | MDP0000413077 | MDP0000489444 | MDP0000269861 | |
| MDP0000878181 | MDP0000596458 | MDP0000256360 | MDP0000208899 | MDP0000124716 | MDP0000176147 | MDP0000437279 | |
| MDP0000170826 | MDP0000195916 | MDP0000127244 | MDP0000208332 | MDP0000773268 | MDP0000270057 | MDP0000197981 | |
| MDP0000508081 | MDP0000792088 | MDP0000256573 | MDP0000317819 | MDP0000165198 | MDP0000707302 | MDP0000672440 | |
| MDP0000940313 | MDP0000297584 | MDP0000546169 | MDP0000302068 | MDP0000230940 | MDP0000143357 | MDP0000716315 | |
| MDP0000186193 | MDP0000298528 | MDP0000654738 | MDP0000348394 | MDP0000258454 | MDP0000231674 | MDP0000290156 | |
| MDP0000804427 | MDP0000190809 | MDP0000139758 | MDP0000150081 | MDP0000454027 | MDP0000293264 | MDP0000277068 | |
| MDP0000755113 | MDP0000289661 | MDP0000297071 | MDP0000124233 | MDP0000317303 | MDP0000119754 | MDP0000177125 | |
| MDP0000166457 | MDP0000140678 | MDP0000200419 | MDP0000931048 | MDP0000319179 | MDP0000224431 | MDP0000139028 | |
| MDP0000364675 | MDP0000361353 | MDP0000950218 | MDP0000640549 | MDP0000302650 | MDP0000162788 | MDP0000774112 | |
| MDP0000593536 | MDP0000668828 | MDP0000144634 | MDP0000276765 | MDP0000672088 | MDP0000119015 | MDP0000610729 | |
| MDP0000232665 | MDP0000656720 | MDP0000195878 | MDP0000186841 | MDP0000340025 | MDP0000893506 | MDP0000263349 | |
| MDP0000202137 | MDP0000309068 | MDP0000326734 | MDP0000166059 | MDP0000599133 | MDP0000226432 | MDP0000244561 | |
| MDP0000158129 | MDP0000336276 | MDP0000809280 | MDP0000202555 | MDP0000788690 | MDP0000289784 | MDP0000134020 | |
| MDP0000218691 | MDP0000700018 | MDP0000212527 | MDP0000193777 | MDP0000275619 | MDP0000273394 | MDP0000242744 | |
| MDP0000251531 | MDP0000295241 | MDP0000828736 | MDP0000197184 | MDP0000319265 | MDP0000217322 | MDP0000239967 | |
| MDP0000149950 | MDP0000291544 | MDP0000229001 | MDP0000311801 | MDP0000782464 | MDP0000443502 | MDP0000254468 | |
| MDP0000137339 | MDP0000761113 | MDP0000157124 | MDP0000722229 | MDP0000239624 | MDP0000419841 | MDP0000782908 | |
| MDP0000222391 | MDP0000791177 | MDP0000181436 | MDP0000254705 | MDP0000164538 | MDP0000139773 | MDP0000310693 | |
| MDP0000217451 | MDP0000283089 | MDP0000244211 | MDP0000701557 | MDP0000158963 | MDP0000297529 | MDP0000726534 | |
| MDP0000116244 | MDP0000648218 | MDP0000178020 | MDP0000279360 | MDP0000221281 | MDP0000685403 | MDP0000391210 | |
| MDP0000216638 | MDP0000153265 | MDP0000127652 | MDP0000194823 | MDP0000158751 | MDP0000568244 | MDP0000176965 | |
| MDP0000290970 | MDP0000222176 | MDP0000389331 | MDP0000128423 | MDP0000292097 | MDP0000282029 | MDP0000602139 | |
| MDP0000507853 | MDP0000120819 | MDP0000695093 | MDP0000166359 | MDP0000157538 | MDP0000201196 | MDP0000394554 | |
| MDP0000137705 | MDP0000221160 | MDP0000430909 | MDP0000884108 | MDP0000196894 | MDP0000012541 | MDP0000123675 | |
| MDP0000702868 | MDP0000225524 | MDP0000666539 | MDP0000326576 | MDP0000446865 | MDP0000561738 | MDP0000156478 | |
| MDP0000197455 | MDP0000158194 | MDP0000202716 | MDP0000257005 | MDP0000545337 | MDP0000280042 | MDP0000453190 | |
| MDP0000284608 | MDP0000305094 | MDP0000859430 | MDP0000307957 | MDP0000302024 | MDP0000457093 | MDP0000304781 | |
| MDP0000249561 | MDP0000184866 | MDP0000314694 | MDP0000619608 | MDP0000279942 | MDP0000274298 | MDP0000760357 | |
| MDP0000218810 | MDP0000156135 | MDP0000917005 | MDP0000391122 | MDP0000255223 | MDP0000189976 | MDP0000181572 | |
| MDP0000686666 | MDP0000911144 | MDP0000562587 | MDP0000172149 | MDP0000242500 | MDP0000151981 | MDP0000315827 | |
| MDP0000414607 | MDP0000893203 | MDP0000529739 | MDP0000529682 | MDP0000391355 | MDP0000239474 | MDP0000126570 | |
| MDP0000192511 | MDP0000189013 | MDP0000885511 | MDP0000257614 | MDP0000894895 | MDP0000503774 | MDP0000282354 | |
| MDP0000278196 | MDP0000292980 | MDP0000906812 | MDP0000138090 | MDP0000161920 | MDP0000210616 | MDP0000150305 | |
| MDP0000377710 | MDP0000453571 | MDP0000289339 | MDP0000255255 | MDP0000119517 | MDP0000586415 | MDP0000266930 | |
| MDP0000481065 | MDP0000776042 | MDP0000155233 | MDP0000252784 | MDP0000529756 | MDP0000413399 | MDP0000786540 | |
| MDP0000744273 | MDP0000218640 | MDP0000178782 | MDP0000263161 | MDP0000497569 | MDP0000349941 | MDP0000228686 | |
| MDP0000244591 | MDP0000228919 | MDP0000175282 | MDP0000297583 | MDP0000349972 | MDP0000265041 | MDP0000214237 | |
| MDP0000404331 | MDP0000264173 | MDP0000837613 | MDP0000159166 | MDP0000208661 | MDP0000732602 | MDP0000720974 | |
| MDP0000492898 | MDP0000135220 | MDP0000279433 | MDP0000168728 | MDP0000128887 | MDP0000283384 | MDP0000220527 | |
| MDP0000239442 | MDP0000440721 | MDP0000350340 | MDP0000191157 | MDP0000635134 | MDP0000264639 | MDP0000153419 | |
| MDP0000250546 | MDP0000506346 | MDP0000673070 | MDP0000340502 | MDP0000495793 | MDP0000201129 | MDP0000551192 | |
| MDP0000132621 | MDP0000034165 | MDP0000657456 | MDP0000320827 | MDP0000195559 | MDP0000124372 | MDP0000232846 | |
| MDP0000240641 | MDP0000292060 | MDP0000209689 | MDP0000308395 | MDP0000144167 | MDP0000190474 | MDP0000198332 | |
| MDP0000516217 | MDP0000496152 | MDP0000744636 | MDP0000777336 | MDP0000226088 | MDP0000250737 | MDP0000899392 | |
| MDP0000161016 | MDP0000120430 | MDP0000822752 | MDP0000287919 | MDP0000873235 | MDP0000599685 | MDP0000553127 | |
| MDP0000188052 | MDP0000803862 | MDP0000840947 | MDP0000143487 | MDP0000280105 | MDP0000322632 | MDP0000277831 | |

TABLE 3-continued

Accession numbers (Velasco et al., 2010; Retrieved from the Internet: Rosaceae.org) of biomarker genes for $CO_2$ injury assessment during cold storage following cold storage imposition. Higher or lower expression levels can result from cold stress resulting from storage imposition.

| | | | | | | | |
|---|---|---|---|---|---|---|---|
| MDP0000127834 | MDP0000569069 | MDP0000210022 | MDP0000784309 | MDP0000508761 | MDP0000237148 | MDP0000183283 | |
| MDP0000164201 | MDP0000200306 | MDP0000166168 | MDP0000157997 | MDP0000123135 | MDP0000865961 | MDP0000163006 | |
| MDP0000198015 | MDP0000419128 | MDP0000461727 | MDP0000830926 | MDP0000215663 | MDP0000725386 | MDP0000146709 | |
| MDP0000188101 | MDP0000819132 | MDP0000218252 | MDP0000788170 | MDP0000194040 | MDP0000162785 | MDP0000700245 | |
| MDP0000154475 | MDP0000199273 | MDP0000493644 | MDP0000312457 | MDP0000133792 | MDP0000202435 | MDP0000903481 | |
| MDP0000219581 | MDP0000319818 | MDP0000730019 | MDP0000120271 | MDP0000240040 | MDP0000133367 | MDP0000272619 | |
| MDP0000159000 | MDP0000233658 | MDP0000352702 | MDP0000195260 | MDP0000193657 | MDP0000309651 | MDP0000130738 | |
| MDP0000836785 | MDP0000276730 | MDP0000265213 | MDP0000124938 | MDP0000435249 | MDP0000675548 | MDP0000150739 | |
| MDP0000203521 | MDP0000220511 | MDP0000261375 | MDP0000661922 | MDP0000269028 | MDP0000307685 | MDP0000186385 | |
| MDP0000649644 | MDP0000121094 | MDP0000707650 | MDP0000563899 | MDP0000318625 | MDP0000127134 | MDP0000605454 | |
| MDP0000388769 | MDP0000128975 | MDP0000705359 | MDP0000163048 | MDP0000560179 | MDP0000271847 | MDP0000287328 | |
| MDP0000762756 | MDP0000730751 | MDP0000589981 | MDP0000169615 | MDP0000458276 | MDP0000783325 | MDP0000147814 | |
| MDP0000565690 | MDP0000866270 | MDP0000302716 | MDP0000212080 | MDP0000229238 | MDP0000238100 | MDP0000538536 | |
| MDP0000566567 | MDP0000159814 | MDP0000318866 | MDP0000229280 | MDP0000203716 | MDP0000209821 | MDP0000258886 | |
| MDP0000453114 | MDP0000534726 | MDP0000145422 | MDP0000283389 | MDP0000256637 | MDP0000196150 | MDP0000218824 | |
| MDP0000725984 | MDP0000127691 | MDP0000224773 | MDP0000700383 | MDP0000193196 | MDP0000299915 | MDP0000288980 | |
| MDP0000360447 | MDP0000619261 | MDP0000203897 | MDP0000829170 | MDP0000306224 | MDP0000265747 | MDP0000276954 | |
| MDP0000126567 | MDP0000531044 | MDP0000135084 | MDP0000060836 | MDP0000301994 | MDP0000134397 | MDP0000190843 | |
| MDP0000292277 | MDP0000705053 | MDP0000706762 | MDP0000131822 | MDP0000706020 | MDP0000137792 | MDP0000210537 | |
| MDP0000612469 | MDP0000129648 | MDP0000228056 | MDP0000422210 | MDP0000476704 | MDP0000387137 | MDP0000671040 | |
| MDP0000759336 | MDP0000683341 | MDP0000317975 | MDP0000246831 | MDP0000440829 | MDP0000253905 | MDP0000798964 | |
| MDP0000943292 | MDP0000343219 | MDP0000875654 | MDP0000201865 | MDP0000136642 | MDP0000518027 | MDP0000301573 | |
| MDP0000388075 | MDP0000230184 | MDP0000372629 | MDP0000281049 | MDP0000150990 | MDP0000651107 | MDP0000442914 | |
| MDP0000140993 | MDP0000188976 | MDP0000295258 | MDP0000177150 | MDP0000155009 | MDP0000177048 | MDP0000144545 | |
| MDP0000139075 | MDP0000543510 | MDP0000137042 | MDP0000877539 | MDP0000651353 | MDP0000455844 | MDP0000530792 | |
| MDP0000547788 | MDP0000241736 | MDP0000309741 | MDP0000174127 | MDP0000222184 | MDP0000499282 | MDP0000223122 | |
| MDP0000874667 | MDP0000533178 | MDP0000283823 | MDP0000165364 | MDP0000708299 | MDP0000225538 | MDP0000251783 | |
| MDP0000138538 | MDP0000567268 | MDP0000481445 | MDP0000241358 | MDP0000158665 | MDP0000634676 | MDP0000854001 | |
| MDP0000420223 | MDP0000248822 | MDP0000483662 | MDP0000298045 | MDP0000652413 | MDP0000919706 | MDP0000541805 | |
| MDP0000369858 | MDP0000168826 | MDP0000664096 | MDP0000200307 | MDP0000123287 | MDP0000156208 | MDP0000256750 | |
| MDP0000888042 | MDP0000148399 | MDP0000120738 | MDP0000610961 | MDP0000326735 | MDP0000189615 | MDP0000235216 | |
| MDP0000280265 | MDP0000645422 | MDP0000737001 | MDP0000523258 | MDP0000318891 | MDP0000456277 | MDP0000264307 | |
| MDP0000147795 | MDP0000299658 | MDP0000289822 | MDP0000405015 | MDP0000932456 | MDP0000193721 | MDP0000321776 | |
| MDP0000128721 | MDP0000286141 | MDP0000280500 | MDP0000231962 | MDP0000119600 | MDP0000744777 | MDP0000155799 | |
| MDP0000891556 | MDP0000658829 | MDP0000539101 | MDP0000252680 | MDP0000254363 | MDP0000668674 | MDP0000386815 | |
| MDP0000576922 | MDP0000787281 | MDP0000421111 | MDP0000281449 | MDP0000313816 | MDP0000216786 | MDP0000316491 | |
| MDP0000226223 | MDP0000798878 | MDP0000632679 | MDP0000319225 | MDP0000251781 | MDP0000822659 | MDP0000296259 | |
| MDP0000269284 | MDP0000658830 | MDP0000200718 | MDP0000154945 | MDP0000244208 | MDP0000564069 | MDP0000286359 | |
| MDP0000225539 | MDP0000736490 | MDP0000204606 | MDP0000305859 | MDP0000659071 | MDP0000385168 | MDP0000150931 | |
| MDP0000699845 | MDP0000437886 | MDP0000526680 | MDP0000641254 | MDP0000138115 | MDP0000302461 | MDP0000157943 | |
| MDP0000789304 | MDP0000168437 | MDP0000641583 | MDP0000239026 | MDP0000124524 | MDP0000207578 | MDP0000511689 | |
| MDP0000220012 | MDP0000294667 | MDP0000294360 | MDP0000555220 | MDP0000208028 | MDP0000393950 | MDP0000146240 | |
| MDP0000261679 | MDP0000271244 | MDP0000206691 | MDP0000251943 | MDP0000929213 | MDP0000280686 | MDP0000303101 | |
| MDP0000729348 | MDP0000044656 | MDP0000227657 | MDP0000461203 | MDP0000309383 | MDP0000295606 | MDP0000686021 | |
| MDP0000182592 | MDP0000167456 | MDP0000276889 | MDP0000161563 | MDP0000205389 | MDP0000618065 | MDP0000897594 | |
| MDP0000939841 | MDP0000147913 | MDP0000159766 | MDP0000599427 | MDP0000131115 | MDP0000293845 | MDP0000244814 | |
| MDP0000788934 | MDP0000500661 | MDP0000632640 | MDP0000256575 | MDP0000156301 | MDP0000251398 | MDP0000206714 | |
| MDP0000229140 | MDP0000665685 | MDP0000481314 | MDP0000262784 | MDP0000139605 | MDP0000213381 | MDP0000192322 | |
| MDP0000316310 | MDP0000124490 | MDP0000184045 | MDP0000186513 | MDP0000648997 | MDP0000647373 | MDP0000153539 | |
| MDP0000638870 | MDP0000288684 | MDP0000830588 | MDP0000161979 | MDP0000204383 | MDP0000544455 | MDP0000125303 | |
| MDP0000225450 | MDP0000908881 | MDP0000323296 | MDP0000233682 | MDP0000715994 | MDP0000153063 | MDP0000226556 | |
| MDP0000046192 | MDP0000176602 | MDP0000386613 | MDP0000268514 | MDP0000140386 | MDP0000751192 | MDP0000281609 | |
| MDP0000782882 | MDP0000266406 | MDP0000527687 | MDP0000391295 | MDP0000554950 | MDP0000160349 | MDP0000376738 | |
| MDP0000125709 | MDP0000368098 | MDP0000744887 | MDP0000121969 | MDP0000212336 | MDP0000157213 | MDP0000134442 | |
| MDP0000233325 | MDP0000674666 | MDP0000400776 | MDP0000155204 | MDP0000431306 | MDP0000943140 | MDP0000389795 | |
| MDP0000513751 | MDP0000135540 | MDP0000153029 | MDP0000195510 | MDP0000807487 | MDP0000119590 | MDP0000147581 | |
| MDP0000300051 | MDP0000559039 | MDP0000119550 | MDP0000122747 | MDP0000250954 | MDP0000179719 | MDP0000173375 | |
| MDP0000801806 | MDP0000215224 | MDP0000127771 | MDP0000555329 | MDP0000624476 | MDP0000283596 | MDP0000276676 | |
| MDP0000183682 | MDP0000134911 | MDP0000119725 | MDP0000905135 | MDP0000538483 | MDP0000612660 | MDP0000278791 | |
| MDP0000140483 | MDP0000193050 | MDP0000307964 | MDP0000223422 | MDP0000889159 | MDP0000301417 | MDP0000256497 | |
| MDP0000300987 | MDP0000709073 | MDP0000153817 | MDP0000460658 | MDP0000214930 | MDP0000146003 | MDP0000213638 | |
| MDP0000662880 | MDP0000245720 | MDP0000460658 | MDP0000303786 | MDP0000218935 | MDP0000185802 | MDP0000642505 | |
| MDP0000288293 | MDP0000134325 | MDP0000231713 | MDP0000720815 | MDP0000813626 | MDP0000872533 | MDP0000311359 | |
| MDP0000933110 | MDP0000345066 | MDP0000154764 | MDP0000141882 | MDP0000546507 | MDP0000274423 | MDP0000296515 | |
| MDP0000124868 | MDP0000228456 | MDP0000475514 | MDP0000278523 | MDP0000239754 | MDP0000221957 | MDP0000212307 | |
| MDP0000361920 | MDP0000186011 | MDP0000564065 | MDP0000284919 | MDP0000299890 | MDP0000166777 | MDP0000182877 | |
| MDP0000213863 | MDP0000265806 | MDP0000498524 | MDP0000136032 | MDP0000235168 | MDP0000179336 | MDP0000515971 | |
| MDP0000264118 | MDP0000672486 | MDP0000515106 | MDP0000163274 | MDP0000463271 | MDP0000755899 | MDP0000164977 | |
| MDP0000407572 | MDP0000383777 | MDP0000276278 | MDP0000267933 | MDP0000119532 | MDP0000811127 | MDP0000831221 | |
| MDP0000836165 | MDP0000740656 | MDP0000277258 | MDP0000159472 | MDP0000130459 | MDP0000318455 | MDP0000944724 | |
| MDP0000273588 | MDP0000124296 | MDP0000683814 | MDP0000172227 | MDP0000857608 | MDP0000180684 | MDP0000202315 | |
| MDP0000264592 | MDP0000611070 | MDP0000148780 | MDP0000165528 | MDP0000197579 | MDP0000290288 | MDP0000305368 | |
| MDP0000183197 | MDP0000927456 | MDP0000120125 | MDP0000203784 | MDP0000121166 | MDP0000380467 | MDP0000622728 | |
| MDP0000364750 | MDP0000233440 | MDP0000225975 | MDP0000292621 | MDP0000759504 | MDP0000162592 | MDP0000321445 | |
| MDP0000266497 | MDP0000231242 | MDP0000803520 | | MDP0000596845 | MDP0000300507 | MDP0000583704 | |

TABLE 3-continued

Accession numbers (Velasco et al., 2010; Retrieved from the Internet: Rosaceae.org) of biomarker genes for $CO_2$ injury assessment during cold storage following cold storage imposition. Higher or lower expression levels can result from cold stress resulting from storage imposition.

| | | | | | | | |
|---|---|---|---|---|---|---|---|
| MDP0000282945 | MDP0000272880 | MDP0000143639 | MDP0000131144 | MDP0000501172 | MDP0000171430 | MDP0000266640 | |
| MDP0000511650 | MDP0000461780 | MDP0000164670 | MDP0000764585 | MDP0000903076 | MDP0000874373 | MDP0000500732 | |
| MDP0000607654 | MDP0000570395 | MDP0000295812 | MDP0000216667 | MDP0000153978 | MDP0000138677 | | |
| MDP0000507003 | MDP0000223224 | MDP0000130244 | MDP0000163930 | MDP0000622590 | MDP0000279292 | MDP0000535048 | |
| MDP0000206473 | MDP0000138729 | MDP0000799387 | MDP0000207215 | MDP0000484742 | MDP0000923711 | MDP0000206973 | |
| MDP0000504527 | MDP0000689946 | MDP0000329703 | MDP0000164386 | MDP0000825698 | MDP0000197297 | MDP0000684133 | |
| MDP0000629143 | MDP0000843632 | MDP0000164610 | MDP0000171850 | MDP0000138057 | MDP0000210077 | MDP0000282332 | |
| MDP0000294379 | MDP0000815242 | MDP0000368495 | MDP0000164909 | MDP0000304127 | MDP0000628976 | MDP0000194270 | |
| MDP0000196018 | MDP0000320763 | MDP0000152448 | MDP0000267621 | MDP0000721792 | MDP0000230265 | MDP0000286915 | |
| MDP0000601071 | MDP0000163943 | MDP0000638442 | MDP0000132235 | MDP0000854242 | MDP0000298491 | MDP0000310641 | |
| MDP0000923290 | MDP0000309382 | MDP0000296708 | MDP0000489978 | MDP0000917143 | MDP0000273221 | MDP0000181616 | |
| MDP0000655939 | MDP0000328817 | MDP0000312701 | MDP0000538523 | MDP0000129167 | MDP0000155715 | MDP0000892438 | |
| MDP0000152232 | MDP0000659260 | MDP0000420320 | MDP0000341605 | MDP0000150848 | MDP0000145565 | MDP0000154855 | |
| MDP0000252171 | MDP0000230402 | MDP0000251669 | MDP0000317763 | MDP0000221635 | MDP0000118810 | MDP0000242277 | |
| MDP0000479478 | MDP0000903805 | MDP0000245784 | MDP0000285032 | MDP0000505247 | MDP0000649022 | MDP0000149951 | |
| MDP0000770103 | MDP0000758655 | MDP0000156921 | MDP0000211643 | MDP0000162456 | MDP0000344130 | MDP0000349483 | |
| MDP0000545122 | MDP0000231179 | MDP0000758119 | MDP0000321735 | MDP0000704196 | MDP0000243237 | MDP0000549598 | |
| MDP0000240643 | MDP0000181419 | MDP0000233177 | MDP0000697638 | MDP0000228815 | MDP0000145793 | MDP0000318715 | |
| MDP0000200649 | MDP0000560468 | MDP0000149907 | MDP0000204316 | MDP0000432621 | MDP0000639167 | MDP0000280691 | |
| MDP0000220160 | MDP0000281940 | MDP0000707567 | MDP0000200783 | MDP0000687873 | MDP0000677842 | MDP0000142608 | |
| MDP0000719836 | MDP0000322416 | MDP0000257119 | MDP0000241227 | MDP0000272663 | MDP0000291249 | MDP0000148725 | |
| MDP0000304911 | MDP0000818514 | MDP0000211727 | MDP0000187103 | MDP0000211875 | MDP0000227876 | MDP0000157065 | |
| MDP0000135858 | MDP0000151647 | MDP0000148288 | MDP0000130913 | MDP0000949986 | MDP0000315037 | MDP0000951223 | |
| MDP0000138071 | MDP0000266435 | MDP0000286933 | MDP0000710349 | MDP0000294423 | MDP0000476035 | MDP0000490846 | |
| MDP0000620549 | MDP0000148815 | MDP0000805422 | MDP0000239834 | MDP0000122421 | MDP0000221660 | MDP0000176461 | |
| MDP0000299980 | MDP0000159070 | MDP0000303872 | MDP0000156595 | MDP0000264424 | MDP0000796490 | MDP0000561228 | |
| MDP0000295562 | MDP0000126274 | MDP0000158046 | MDP0000866008 | MDP0000717000 | MDP0000529420 | MDP0000150498 | |
| MDP0000920394 | MDP0000826636 | MDP0000619097 | MDP0000207761 | MDP0000315119 | MDP0000441757 | MDP0000635041 | |
| MDP0000132608 | MDP0000259614 | MDP0000592961 | MDP0000486907 | MDP0000312875 | MDP0000896511 | MDP0000810872 | |
| MDP0000134685 | MDP0000060869 | MDP0000122413 | MDP0000437033 | MDP0000178508 | MDP0000920266 | MDP0000214691 | |
| MDP0000909262 | MDP0000198955 | MDP0000352200 | MDP0000309676 | MDP0000170129 | MDP0000093999 | MDP0000268550 | |
| MDP0000436890 | MDP0000477966 | MDP0000365787 | MDP0000716308 | MDP0000120830 | MDP0000249524 | MDP0000231477 | |
| MDP0000759591 | MDP0000275926 | MDP0000304794 | MDP0000226135 | MDP0000136545 | MDP0000311922 | MDP0000255974 | |
| MDP0000296179 | MDP0000619638 | MDP0000551974 | MDP0000135234 | MDP0000132360 | MDP0000607509 | MDP0000157044 | |
| MDP0000804928 | MDP0000197224 | MDP0000778663 | MDP0000288597 | MDP0000804900 | MDP0000187988 | MDP0000566415 | |
| MDP0000058337 | MDP0000119148 | MDP0000612909 | MDP0000125113 | MDP0000119756 | MDP0000434765 | MDP0000221634 | |
| MDP0000748916 | MDP0000552625 | MDP0000336630 | MDP0000270731 | MDP0000231920 | MDP0000805606 | MDP0000269415 | |
| MDP0000120188 | MDP0000393972 | MDP0000182115 | MDP0000601086 | MDP0000513900 | MDP0000194255 | MDP0000312185 | |
| MDP0000155293 | MDP0000356821 | MDP0000315980 | MDP0000830772 | MDP0000674580 | MDP0000767905 | MDP0000287555 | |
| MDP0000265423 | MDP0000150088 | MDP0000240458 | MDP0000304784 | MDP0000200361 | MDP0000601734 | MDP0000539269 | |
| MDP0000733506 | MDP0000576205 | MDP0000207048 | MDP0000846849 | MDP0000865032 | MDP0000312021 | MDP0000266257 | |
| MDP0000169611 | MDP0000342145 | MDP0000142895 | MDP0000145050 | MDP0000416305 | MDP0000229093 | MDP0000226276 | |
| MDP0000162579 | MDP0000499190 | MDP0000119402 | MDP0000373095 | MDP0000248673 | MDP0000236124 | MDP0000265516 | |
| MDP0000188674 | MDP0000903417 | MDP0000264514 | MDP0000918923 | MDP0000263292 | MDP0000527802 | MDP0000252922 | |
| MDP0000118766 | MDP0000183814 | MDP0000127563 | MDP0000324398 | MDP0000241597 | MDP0000201389 | MDP0000302349 | |
| MDP0000503944 | MDP0000606526 | MDP0000248168 | MDP0000222539 | MDP0000378200 | MDP0000120761 | MDP0000176426 | |
| MDP0000229796 | MDP0000818915 | MDP0000303430 | MDP0000180803 | MDP0000316490 | MDP0000164296 | MDP0000592869 | |
| MDP0000301092 | MDP0000252048 | MDP0000891965 | MDP0000262135 | MDP0000400617 | MDP0000217213 | MDP0000158667 | |
| MDP0000506359 | MDP0000284842 | MDP0000253047 | MDP0000234690 | MDP0000306888 | MDP0000184534 | MDP0000287231 | |
| MDP0000293165 | MDP0000174367 | MDP0000682471 | MDP0000848504 | MDP0000311969 | MDP0000850250 | MDP0000320695 | |
| MDP0000818605 | MDP0000948298 | MDP0000473817 | MDP0000217209 | MDP0000265366 | MDP0000491020 | MDP0000222520 | |
| MDP0000816018 | MDP0000286587 | MDP0000190508 | MDP0000780624 | MDP0000302192 | MDP0000287679 | MDP0000271964 | |
| MDP0000891555 | MDP0000412925 | MDP0000676293 | MDP0000136803 | MDP0000306151 | MDP0000539299 | MDP0000315045 | |
| MDP0000769652 | MDP0000157712 | MDP0000265411 | MDP0000227827 | MDP0000132952 | MDP0000615196 | MDP0000168387 | |
| MDP0000316126 | MDP0000242738 | MDP0000665384 | MDP0000208200 | MDP0000320108 | MDP0000388415 | MDP0000313097 | |
| MDP0000715898 | MDP0000423544 | MDP0000859733 | MDP0000311432 | MDP0000284910 | MDP0000456401 | MDP0000266393 | |
| MDP0000177906 | MDP0000867863 | MDP0000195993 | MDP0000489408 | MDP0000745475 | MDP0000527985 | MDP0000793247 | |
| MDP0000287581 | MDP0000597906 | MDP0000418187 | MDP0000455180 | MDP0000611163 | MDP0000396037 | MDP0000560705 | |
| MDP0000920189 | MDP0000228670 | MDP0000155113 | MDP0000727570 | MDP0000128602 | MDP0000131142 | MDP0000121185 | |
| MDP0000708135 | MDP0000182546 | MDP0000201082 | MDP0000733256 | MDP0000218940 | MDP0000134162 | MDP0000288670 | |
| MDP0000684655 | MDP0000702872 | MDP0000180580 | MDP0000442306 | MDP0000943296 | MDP0000201903 | MDP0000264519 | |
| MDP0000755280 | MDP0000324894 | MDP0000136805 | MDP0000183375 | MDP0000187812 | MDP0000227886 | MDP0000312097 | |
| MDP0000479163 | MDP0000500159 | MDP0000263529 | MDP0000183375 | MDP0000128130 | MDP0000258253 | MDP0000246999 | |
| MDP0000166704 | MDP0000254930 | MDP0000440443 | MDP0000326412 | MDP0000255005 | MDP0000270308 | MDP0000268320 | |
| MDP0000204569 | MDP0000122540 | MDP0000307853 | MDP0000289861 | MDP0000320322 | MDP0000125933 | MDP0000241711 | |
| MDP0000678982 | MDP0000122127 | MDP0000247130 | MDP0000131626 | MDP0000800086 | MDP0000135375 | MDP0000192162 | |
| MDP0000275850 | MDP0000234782 | MDP0000236351 | MDP0000173626 | MDP0000738777 | MDP0000193833 | MDP0000147123 | |
| MDP0000774713 | MDP0000715270 | MDP0000351987 | MDP0000656101 | MDP0000203591 | MDP0000302224 | MDP0000152343 | |
| MDP0000913661 | MDP0000247502 | MDP0000298697 | MDP0000203109 | MDP0000303216 | MDP0000397831 | MDP0000630247 | |
| MDP0000543445 | MDP0000221075 | MDP0000847152 | MDP0000928934 | MDP0000860874 | MDP0000245952 | MDP0000292294 | |
| MDP0000300045 | MDP0000170739 | MDP0000657517 | MDP0000871656 | MDP0000428660 | MDP0000226363 | MDP0000140259 | |
| MDP0000336313 | MDP0000799946 | MDP0000280910 | MDP0000250597 | MDP0000166068 | MDP0000264636 | MDP0000885666 | |
| MDP0000943304 | MDP0000836051 | MDP0000141333 | MDP0000266125 | MDP0000296911 | MDP0000254385 | MDP0000182615 | |
| MDP0000758881 | MDP0000269977 | MDP0000887395 | MDP0000187726 | MDP0000445131 | MDP0000299702 | MDP0000214281 | |
| MDP0000127773 | MDP0000811844 | MDP0000181160 | MDP0000272499 | MDP0000865717 | MDP0000829787 | MDP0000321160 | |

TABLE 3-continued

Accession numbers (Velasco et al., 2010; Retrieved from the Internet: Rosaceae.org) of biomarker genes for $CO_2$ injury assessment during cold storage following cold storage imposition. Higher or lower expression levels can result from cold stress resulting from storage imposition.

| | | | | | | | |
|---|---|---|---|---|---|---|---|
| MDP0000523205 | MDP0000148081 | MDP0000069858 | MDP0000243728 | MDP0000299256 | MDP0000706702 | MDP0000151003 | |
| MDP0000766844 | MDP0000481590 | MDP0000404539 | MDP0000293103 | MDP0000469192 | MDP0000882268 | MDP0000441699 | |
| MDP0000252589 | MDP0000891538 | MDP0000172092 | MDP0000250125 | MDP0000871402 | MDP0000198903 | MDP0000828036 | |
| MDP0000202883 | MDP0000463117 | MDP0000635132 | MDP0000180642 | MDP0000313657 | MDP0000200780 | MDP0000547181 | |
| MDP0000293002 | MDP0000137211 | MDP0000150973 | MDP0000877084 | MDP0000153378 | MDP0000706371 | MDP0000197283 | |
| MDP0000195385 | MDP0000560467 | MDP0000180783 | MDP0000784168 | MDP0000346562 | MDP0000130345 | MDP0000122734 | |
| MDP0000889787 | MDP0000857446 | MDP0000629887 | MDP0000835932 | MDP0000136757 | MDP0000146168 | MDP0000139111 | |
| MDP0000265644 | MDP0000223749 | MDP0000243650 | MDP0000907486 | MDP0000122935 | MDP0000459146 | MDP0000219600 | |
| MDP0000183751 | MDP0000244304 | MDP0000776321 | MDP0000737023 | MDP0000312878 | MDP0000243572 | MDP0000284498 | |
| MDP0000280820 | MDP0000251295 | MDP0000179374 | MDP0000272655 | MDP0000175375 | MDP0000204702 | MDP0000175821 | |
| MDP0000753318 | MDP0000228494 | MDP0000659818 | MDP0000247003 | MDP0000134805 | MDP0000557111 | MDP0000141191 | |
| MDP0000664773 | MDP0000314088 | MDP0000306738 | MDP0000208329 | MDP0000191423 | MDP0000811098 | MDP0000239958 | |
| MDP0000237069 | MDP0000313643 | MDP0000772420 | MDP0000187921 | MDP0000249564 | MDP0000838018 | MDP0000231423 | |
| MDP0000450991 | MDP0000453295 | MDP0000377222 | MDP0000286463 | MDP0000165503 | MDP0000441093 | MDP0000771031 | |
| MDP0000264351 | MDP0000281626 | MDP0000228457 | MDP0000500806 | MDP0000322279 | MDP0000286574 | MDP0000413365 | |
| MDP0000200646 | MDP0000291146 | MDP0000617956 | MDP0000708634 | MDP0000185156 | MDP0000294355 | MDP0000159635 | |
| MDP0000266144 | MDP0000225211 | MDP0000150382 | MDP0000164974 | MDP0000194305 | MDP0000528111 | MDP0000237357 | |
| MDP0000196174 | MDP0000432499 | MDP0000272747 | MDP0000193927 | MDP0000294180 | MDP0000217851 | MDP0000164203 | |
| MDP0000886138 | MDP0000574556 | MDP0000336305 | MDP0000131602 | MDP0000350718 | MDP0000259741 | MDP0000407067 | |
| MDP0000727700 | MDP0000164828 | MDP0000687619 | MDP0000250114 | MDP0000288329 | MDP0000158955 | MDP0000780011 | |
| MDP0000390049 | MDP0000305583 | MDP0000235112 | MDP0000180004 | MDP0000581549 | MDP0000310638 | MDP0000236072 | |
| MDP0000873667 | MDP0000353594 | MDP0000291621 | MDP0000224397 | MDP0000195926 | MDP0000145972 | MDP0000568871 | |
| MDP0000241557 | MDP0000145252 | MDP0000305723 | MDP0000620797 | MDP0000268092 | MDP0000191851 | MDP0000165523 | |
| MDP0000296025 | MDP0000585239 | MDP0000732145 | MDP0000253105 | MDP0000204468 | MDP0000124832 | MDP0000162502 | |
| MDP0000255770 | MDP0000162244 | MDP0000273608 | MDP0000201205 | MDP0000120560 | MDP0000199319 | MDP0000784035 | |
| MDP0000167107 | MDP0000563233 | MDP0000453797 | MDP0000259687 | MDP0000951949 | MDP0000319806 | MDP0000250536 | |
| MDP0000310704 | MDP0000334306 | MDP0000286646 | MDP0000318256 | MDP0000657536 | MDP0000808124 | MDP0000797124 | |
| MDP0000256486 | MDP0000135831 | MDP0000290295 | MDP0000218190 | MDP0000134596 | MDP0000644930 | MDP0000244607 | |
| MDP0000273470 | MDP0000199152 | MDP0000189514 | MDP0000507001 | MDP0000275032 | MDP0000284686 | MDP0000610179 | |
| MDP0000939633 | MDP0000363287 | MDP0000221126 | MDP0000212178 | MDP0000767063 | MDP0000774924 | MDP0000235313 | |
| MDP0000139052 | MDP0000345457 | MDP0000191848 | MDP0000711891 | MDP0000133933 | MDP0000290650 | MDP0000263680 | |
| MDP0000215525 | MDP0000270051 | MDP0000277208 | MDP0000253406 | MDP0000126026 | MDP0000559463 | MDP0000350710 | |
| MDP0000347336 | MDP0000298232 | MDP0000208345 | MDP0000189326 | MDP0000431790 | MDP0000804707 | MDP0000186019 | |
| MDP0000506825 | MDP0000380032 | MDP0000905147 | MDP0000161197 | MDP0000255567 | MDP0000175501 | MDP0000447570 | |
| MDP0000245123 | MDP0000178304 | MDP0000275579 | MDP0000601325 | MDP0000195460 | MDP0000276264 | MDP0000531313 | |
| MDP0000732635 | MDP0000839736 | MDP0000281216 | MDP0000240444 | MDP0000672731 | MDP0000139844 | MDP0000296317 | |
| MDP0000190316 | MDP0000189111 | MDP0000276013 | MDP0000251098 | MDP0000768369 | MDP0000162382 | MDP0000497953 | |
| MDP0000274905 | MDP0000348523 | MDP0000160972 | MDP0000251098 | MDP0000613481 | MDP0000294333 | MDP0000473750 | |
| MDP0000858181 | MDP0000221435 | MDP0000212975 | MDP0000200614 | MDP0000248063 | MDP0000717656 | MDP0000245462 | |
| MDP0000590116 | MDP0000805503 | MDP0000165524 | MDP0000194935 | MDP0000220179 | MDP0000835812 | MDP0000922120 | |
| MDP0000759646 | MDP0000193438 | MDP0000696497 | MDP0000183836 | MDP0000870406 | MDP0000211848 | MDP0000174766 | |
| MDP0000488361 | MDP0000644979 | MDP0000129670 | MDP0000231711 | MDP0000282995 | MDP0000309171 | MDP0000136847 | |
| MDP0000289110 | MDP0000384593 | MDP0000299277 | MDP0000770800 | MDP0000506495 | MDP0000362615 | MDP0000200253 | |
| MDP0000167199 | MDP0000652676 | MDP0000517479 | MDP0000217467 | MDP0000945834 | MDP0000242554 | MDP0000200442 | |
| MDP0000199009 | MDP0000210067 | MDP0000833352 | MDP0000206859 | MDP0000835304 | MDP0000145027 | MDP0000216337 | |
| MDP0000275128 | MDP0000859897 | MDP0000212327 | MDP0000210295 | MDP0000207467 | MDP0000859563 | MDP0000139316 | |
| MDP0000304208 | MDP0000479094 | MDP0000535127 | MDP0000280093 | MDP0000930551 | MDP0000544274 | MDP0000183313 | |
| MDP0000185796 | MDP0000595671 | MDP0000327231 | MDP0000144510 | MDP0000242552 | MDP0000648253 | MDP0000877369 | |
| MDP0000206910 | MDP0000129445 | MDP0000630439 | MDP0000152670 | MDP0000567960 | MDP0000122329 | MDP0000224509 | |
| MDP0000739699 | MDP0000321690 | MDP0000321018 | MDP0000192665 | MDP0000553490 | MDP0000918135 | MDP0000495801 | |
| MDP0000542944 | MDP0000162721 | MDP0000310001 | MDP0000041421 | MDP0000195723 | MDP0000251546 | MDP0000242885 | |
| MDP0000202726 | MDP0000145463 | MDP0000239643 | MDP0000706548 | MDP0000585915 | MDP0000281004 | MDP0000445110 | |
| MDP0000299310 | MDP0000221444 | MDP0000143463 | MDP0000201743 | MDP0000194082 | MDP0000295594 | | |
| MDP0000624279 | MDP0000292132 | MDP0000231960 | MDP0000341560 | MDP0000772938 | MDP0000741253 | MDP0000126049 | |
| MDP0000200737 | MDP0000509613 | MDP0000341099 | MDP0000279502 | MDP0000121244 | MDP0000175772 | MDP0000303463 | |
| MDP0000296062 | MDP0000788345 | MDP0000223807 | MDP0000209313 | MDP0000348067 | MDP0000175949 | MDP0000132692 | |
| MDP0000263959 | MDP0000233154 | MDP0000713493 | MDP0000207731 | MDP0000228658 | MDP0000557785 | MDP0000169509 | |
| MDP0000182342 | MDP0000464691 | MDP0000607330 | MDP0000303989 | MDP0000320496 | MDP0000148855 | MDP0000219793 | |
| MDP0000782085 | MDP0000196588 | MDP0000909197 | MDP0000424447 | MDP0000399965 | MDP0000136589 | MDP0000223628 | |
| MDP0000183478 | MDP0000897855 | MDP0000325346 | MDP0000257928 | MDP0000211981 | MDP0000214291 | MDP0000396530 | |
| MDP0000158694 | MDP0000189486 | MDP0000222186 | MDP0000143462 | MDP0000182154 | MDP0000256438 | MDP0000173593 | |
| MDP0000680183 | MDP0000322202 | MDP0000289768 | MDP0000205224 | MDP0000729533 | MDP0000299137 | MDP0000157711 | |
| MDP0000182695 | MDP0000145382 | MDP0000207393 | MDP0000205224 | MDP0000292462 | MDP0000129882 | MDP0000305860 | |
| MDP0000920400 | MDP0000244990 | MDP0000395101 | MDP0000185136 | MDP0000284481 | MDP0000263752 | MDP0000163170 | |
| MDP0000268304 | MDP0000854250 | MDP0000146195 | MDP0000312397 | MDP0000214162 | MDP0000713750 | MDP0000199601 | |
| MDP0000861708 | MDP0000734649 | MDP0000450601 | MDP0000711374 | MDP0000206298 | MDP0000264271 | MDP0000286702 | |
| MDP0000188113 | MDP0000452083 | MDP0000310945 | MDP0000376256 | MDP0000306427 | MDP0000770089 | MDP0000256194 | |
| MDP0000736035 | MDP0000186860 | MDP0000209438 | MDP0000149454 | MDP0000307340 | MDP0000871981 | MDP0000146677 | |
| MDP0000138634 | MDP0000178196 | MDP0000309351 | MDP0000252508 | MDP0000228367 | MDP0000920870 | MDP0000213630 | |
| MDP0000154155 | MDP0000586302 | MDP0000431696 | MDP0000206496 | MDP0000194268 | MDP0000754524 | MDP0000120526 | |
| MDP0000219062 | MDP0000215270 | MDP0000128786 | MDP0000164498 | MDP0000214748 | MDP0000275440 | MDP0000270739 | |
| MDP0000395867 | MDP0000137655 | MDP0000298659 | MDP0000292807 | MDP0000817852 | MDP0000154046 | MDP0000293974 | |
| MDP0000213102 | MDP0000301666 | MDP0000234499 | MDP0000228109 | MDP0000303074 | MDP0000129426 | MDP0000284559 | |
| MDP0000794439 | MDP0000165846 | MDP0000311618 | MDP0000701887 | MDP0000906565 | MDP0000266638 | MDP0000158886 | |
| MDP0000119071 | MDP0000123488 | MDP0000137826 | MDP0000135019 | MDP0000158576 | MDP0000293886 | MDP0000244902 | |

TABLE 3-continued

Accession numbers (Velasco et al., 2010; Retrieved from the Internet:
Rosaceae.org) of biomarker genes for $CO_2$ injury assessment during cold storage
following cold storage imposition. Higher or lower expression levels can result from cold
stress resulting from storage imposition.

| | | | | | | |
|---|---|---|---|---|---|---|
| MDP0000127858 | MDP0000126669 | MDP0000196404 | MDP0000466345 | MDP0000282415 | MDP0000150868 | MDP0000467552 |
| MDP0000261492 | MDP0000242979 | MDP0000902434 | MDP0000635582 | MDP0000215958 | MDP0000266089 | MDP0000161881 |
| MDP0000145045 | MDP0000230141 | MDP0000133811 | MDP0000597773 | MDP0000154506 | MDP0000287459 | MDP0000260154 |
| MDP0000787216 | MDP0000123747 | MDP0000568825 | MDP0000383450 | MDP0000227405 | MDP0000394944 | MDP0000215382 |
| MDP0000564318 | MDP0000435315 | MDP0000910895 | MDP0000654783 | MDP0000376469 | MDP0000273795 | MDP0000130884 |
| MDP0000241592 | MDP0000158047 | MDP0000232344 | MDP0000256389 | MDP0000124866 | MDP0000161424 | MDP0000157408 |
| MDP0000191304 | MDP0000154734 | MDP0000676744 | MDP0000257242 | MDP0000184300 | MDP0000563788 | MDP0000165719 |
| MDP0000280001 | MDP0000426496 | MDP0000128790 | MDP0000138447 | MDP0000302538 | MDP0000458350 | MDP0000301119 |
| MDP0000548790 | MDP0000190504 | MDP0000157404 | MDP0000314763 | MDP0000295029 | MDP0000173508 | MDP0000157771 |
| MDP0000552120 | MDP0000368720 | MDP0000864660 | MDP0000668252 | MDP0000430546 | MDP0000883367 | MDP0000147902 |
| MDP0000566057 | MDP0000442260 | MDP0000884047 | MDP0000190181 | MDP0000896307 | MDP0000221867 | MDP0000155603 |
| MDP0000842877 | MDP0000135898 | MDP0000279395 | MDP0000197292 | MDP0000249932 | MDP0000856686 | MDP0000237150 |
| MDP0000306121 | MDP0000281041 | MDP0000889931 | MDP0000134341 | MDP0000145764 | MDP0000128058 | MDP0000284488 |
| MDP0000854541 | MDP0000251656 | MDP0000181188 | MDP0000251025 | MDP0000266683 | MDP0000869501 | MDP0000170101 |
| MDP0000635152 | MDP0000281816 | MDP0000343280 | MDP0000766072 | MDP0000860226 | MDP0000188388 | MDP0000270603 |
| MDP0000188054 | MDP0000172320 | MDP0000127930 | MDP0000312731 | MDP0000897242 | MDP0000165286 | MDP0000190016 |
| MDP0000253075 | MDP0000192074 | MDP0000787808 | MDP0000309587 | MDP0000650358 | MDP0000136653 | MDP0000155060 |
| MDP0000239443 | MDP0000825373 | MDP0000275026 | MDP0000181521 | MDP0000237733 | MDP0000037814 | |

Figure 5:
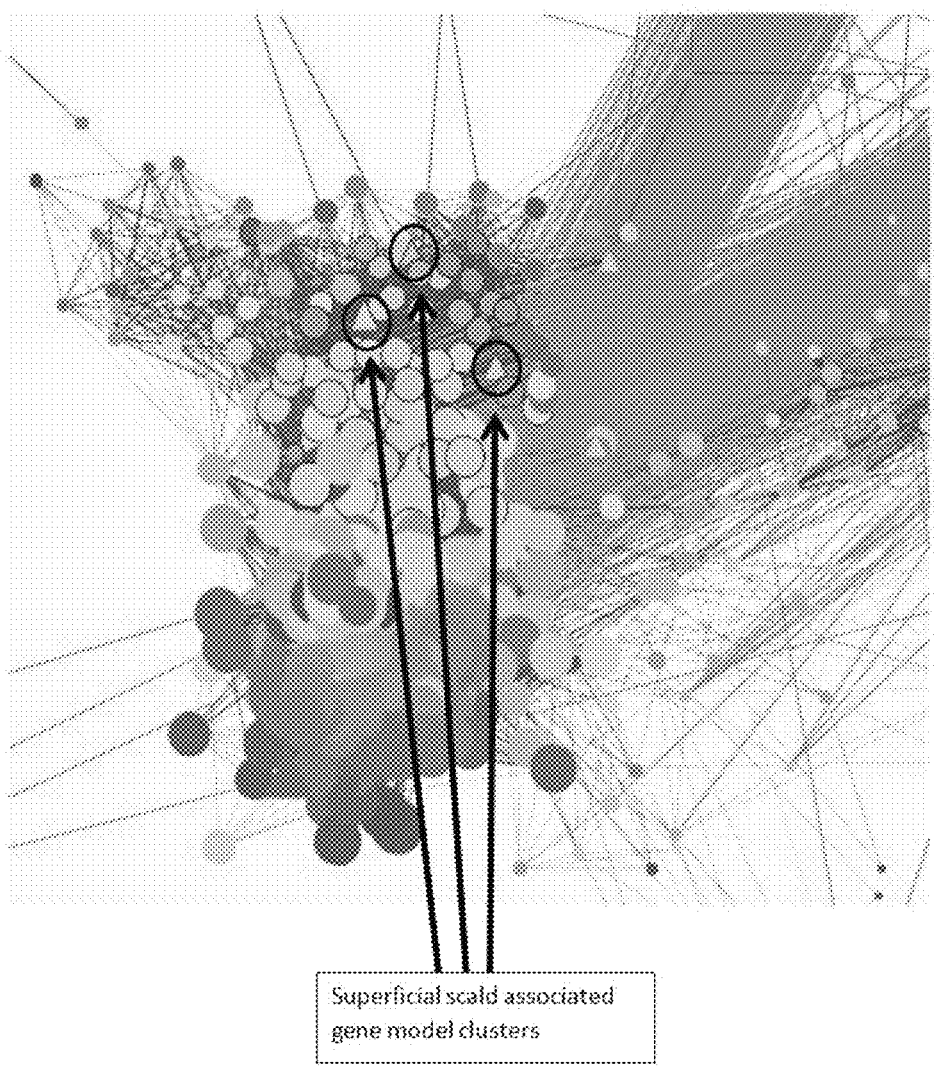
FIG. 5 shows a metabolic-gene expression correlations network illustrating closely related metabolites (circles, representing a single metabolite) and gene model k-means clusters (triangles, representing many highly correlated genes). Nodes closely positioned and linked with red edges (lines) are highly, positively correlated. Nodes outlined in black are those highly correlated with methanol (R>0.700), a metabolite linked with superficial scald symptom development in 'Granny Smith'. Risk assessment biomarker genes for superficial scald and other late-term disorders reside in the three highlighted gene model clusters.

Susceptibility to develop superficial scald is often quite different depending on environmental location of the apples. To discover putative biomarkers, genes were selected from 'Red Delicious' apple peel tissue collected from 6 different orchard locations with observed differences in superficial scald injury incidence. Candidate biomarker genes were selected using Pearson correlation analysis (R, Bioconductor) with a p-value cut off of 0.05. Genes that expression changes at harvest correlated with superficial scald injury incidence, with a correlation coefficient of at least 0.6 were selected for further filtering. From a total of 63541 gene models, 1106 that changed at least 4-fold in tissues showing the lowest and highest development of superficial scald and with an average expression value of at least 1 RPKM per sample were selected as potential at harvest predictive biomarkers of superficial scald (Table 4). Because superficial scald can be adequately controlled using appropriate storage conditions, indicating whether storage conditions are actually working or monitoring risk during storage is also a useful tool for this disorder. Increases in superficial scald risk-associated gene expression (FIG. 5) began at 1 month for a few candidates, finally resulting in the selection of 690 candidates for early indication of superficial scald risk (Table 5). Monitoring multiple risk assessment biomarkers can better ensure that changes are based on more biochemical systems associated with risk.

TABLE 4

Accession numbers (Velasco et al., 2010; Retrieved from the Internet:
Rosaceae.org) of biomarker genes for superficial scald risk assessment during at-
harvest. Higher or lower expression levels can result from cold stress resulting from
storage imposition.

| | | | | | | |
|---|---|---|---|---|---|---|
| MDP0000289575 | MDP0000213320 | MDP0000177522 | MDP0000717184 | MDP0000631171 | MDP0000655623 | MDP0000731637 |
| MDP0000313905 | MDP0000638953 | MDP0000144115 | MDP0000320382 | MDP0000262190 | MDP0000202740 | MDP0000180378 |
| MDP0000433093 | MDP0000232968 | MDP0000283613 | MDP0000215302 | MDP0000319726 | MDP0000176025 | MDP0000361876 |
| MDP0000516091 | MDP0000125476 | MDP0000163474 | MDP0000135287 | MDP0000508916 | MDP0000871409 | MDP0000275553 |
| MDP0000156132 | MDP0000124687 | MDP0000235002 | MDP0000507270 | MDP0000153860 | MDP0000132044 | MDP0000267615 |
| MDP0000318040 | MDP0000172972 | MDP0000304954 | MDP0000120272 | MDP0000121120 | MDP0000820453 | MDP0000197521 |
| MDP0000415930 | MDP0000138035 | MDP0000215722 | MDP0000124509 | MDP0000156068 | MDP0000183189 | MDP0000261492 |
| MDP0000261079 | MDP0000291259 | MDP0000344650 | MDP0000868649 | MDP0000474856 | MDP0000882683 | MDP0000120700 |
| MDP0000212886 | MDP0000120956 | MDP0000313254 | MDP0000895201 | MDP0000207314 | MDP0000319079 | MDP0000214384 |
| MDP0000140157 | MDP0000193646 | MDP0000279740 | MDP0000601017 | MDP0000653408 | MDP0000853568 | MDP0000179389 |
| MDP0000522839 | MDP0000347935 | MDP0000347863 | MDP0000279176 | MDP0000142739 | MDP0000387483 | MDP0000169344 |
| MDP0000686132 | MDP0000369898 | MDP0000904058 | MDP0000141949 | MDP0000209761 | MDP0000243224 | MDP0000230950 |
| MDP0000277425 | MDP0000737713 | MDP0000320910 | MDP0000291399 | MDP0000312108 | MDP0000215578 | MDP0000411018 |
| MDP0000182628 | MDP0000250672 | MDP0000237931 | MDP0000349941 | MDP0000399965 | MDP0000165443 | MDP0000943790 |
| MDP0000159869 | MDP0000176753 | MDP0000776092 | MDP0000255275 | MDP0000310682 | MDP0000946443 | MDP0000293407 |
| MDP0000361139 | MDP0000242656 | MDP0000133066 | MDP0000305689 | MDP0000309382 | MDP0000167951 | MDP0000197294 |
| MDP0000378591 | MDP0000851390 | MDP0000288632 | MDP0000401045 | MDP0000933747 | MDP0000318862 | MDP0000169201 |
| MDP0000224489 | MDP0000202040 | MDP0000230821 | MDP0000214259 | MDP0000314365 | MDP0000334306 | MDP0000941890 |
| MDP0000224176 | MDP0000194377 | MDP0000496646 | MDP0000281427 | MDP0000661747 | MDP0000529463 | MDP0000880462 |
| MDP0000165543 | MDP0000704323 | MDP0000175408 | MDP0000574556 | MDP0000647735 | MDP0000310288 | MDP0000233192 |
| MDP0000294123 | MDP0000137325 | MDP0000072936 | MDP0000432499 | MDP0000188386 | MDP0000164814 | MDP0000249932 |
| MDP0000203358 | MDP0000898595 | MDP0000293236 | MDP0000295321 | MDP0000215049 | MDP0000185616 | MDP0000192825 |
| MDP0000443024 | MDP0000223864 | MDP0000303280 | MDP0000224372 | MDP0000268711 | MDP0000342064 | MDP0000259615 |
| MDP0000258335 | MDP0000149963 | MDP0000799890 | MDP0000358823 | MDP0000417755 | MDP0000282435 | MDP0000170551 |
| MDP0000830611 | MDP0000274608 | MDP0000722481 | MDP0000169335 | MDP0000135721 | MDP0000262784 | MDP0000197833 |
| MDP0000239443 | MDP0000254595 | MDP0000415109 | MDP0000796588 | MDP0000368412 | MDP0000256575 | MDP0000161846 |
| MDP0000854541 | MDP0000116595 | MDP0000520902 | MDP0000293072 | MDP0000712524 | MDP0000949494 | MDP0000287512 |
| MDP0000351376 | MDP0000722373 | MDP0000320289 | MDP0000242946 | MDP0000876051 | MDP0000793261 | MDP0000842724 |
| MDP0000568871 | MDP0000164181 | MDP0000140641 | MDP0000458965 | MDP0000306215 | MDP0000310582 | MDP0000634462 |
| MDP0000156263 | MDP0000119092 | MDP0000119066 | MDP0000678128 | MDP0000417786 | MDP0000585315 | MDP0000149647 |

TABLE 4-continued

Accession numbers (Velasco et al., 2010; Retrieved from the Internet: Rosaceae.org) of biomarker genes for superficial scald risk assessment during at-harvest. Higher or lower expression levels can result from cold stress resulting from storage imposition.

| | | | | | | | |
|---|---|---|---|---|---|---|---|
| MDP0000314471 | MDP0000590105 | MDP0000272737 | MDP0000851476 | MDP0000569492 | MDP0000817494 | MDP0000187917 | |
| MDP0000138715 | MDP0000164478 | MDP0000320542 | MDP0000224750 | MDP0000149770 | MDP0000304038 | MDP0000123699 | |
| MDP0000192433 | MDP0000134572 | MDP0000214747 | MDP0000866655 | MDP0000600199 | MDP0000216728 | MDP0000205641 | |
| MDP0000265636 | MDP0000152120 | MDP0000131201 | MDP0000871736 | MDP0000245305 | MDP0000771577 | MDP0000840031 | |
| MDP0000298189 | MDP0000284916 | MDP0000495763 | MDP0000850449 | MDP0000233740 | MDP0000346630 | MDP0000268910 | |
| MDP0000293203 | MDP0000265524 | MDP0000227876 | MDP0000128173 | MDP0000191848 | MDP0000223383 | MDP0000217467 | |
| MDP0000273980 | MDP0000257891 | MDP0000583574 | MDP0000269711 | MDP0000215300 | MDP0000720785 | MDP0000201205 | |
| MDP0000201897 | MDP0000237134 | MDP0000174081 | MDP0000436155 | MDP0000264403 | MDP0000648408 | MDP0000766771 | |
| MDP0000133156 | MDP0000790904 | MDP0000452677 | MDP0000937996 | MDP0000139612 | MDP0000312965 | MDP0000246502 | |
| MDP0000176265 | MDP0000443824 | MDP0000184034 | MDP0000291152 | MDP0000240321 | MDP0000596604 | MDP0000191304 | |
| MDP0000356392 | MDP0000299146 | MDP0000889675 | MDP0000651174 | MDP0000501048 | MDP0000477241 | MDP0000266472 | |
| MDP0000144890 | MDP0000745895 | MDP0000321182 | MDP0000264506 | MDP0000124819 | MDP0000180370 | MDP0000210030 | |
| MDP0000226644 | MDP0000447081 | MDP0000211593 | MDP0000286692 | MDP0000932002 | MDP0000157227 | MDP0000861936 | |
| MDP0000914171 | MDP0000807972 | MDP0000579628 | MDP0000192468 | MDP0000325473 | MDP0000210081 | MDP0000174273 | |
| MDP0000451827 | MDP0000130537 | MDP0000207048 | MDP0000258192 | MDP0000791829 | MDP0000227393 | MDP0000276468 | |
| MDP0000805790 | MDP0000759984 | MDP0000175030 | MDP0000166278 | MDP0000766213 | MDP0000126178 | MDP0000482042 | |
| MDP0000538720 | MDP0000156188 | MDP0000563240 | MDP0000237733 | MDP0000295195 | MDP0000568497 | MDP0000150458 | |
| MDP0000140342 | MDP0000298849 | MDP0000296989 | MDP0000638263 | MDP0000208667 | MDP0000305746 | MDP0000501238 | |
| MDP0000394035 | MDP0000278577 | MDP0000673494 | MDP0000127757 | MDP0000322300 | MDP0000250487 | MDP0000261330 | |
| MDP0000276431 | MDP0000206274 | MDP0000174818 | MDP0000125452 | MDP0000262183 | MDP0000505386 | MDP0000121577 | |
| MDP0000434333 | MDP0000806127 | MDP0000228711 | MDP0000266942 | MDP0000904515 | MDP0000932838 | MDP0000821066 | |
| MDP0000291748 | MDP0000250226 | MDP0000876439 | MDP0000262699 | MDP0000263222 | MDP0000556214 | MDP0000402540 | |
| MDP0000229126 | MDP0000167758 | MDP0000782670 | MDP0000750294 | MDP0000206886 | MDP0000801340 | MDP0000411240 | |
| MDP0000792264 | MDP0000849696 | MDP0000138764 | MDP0000804605 | MDP0000315594 | MDP0000189850 | MDP0000588065 | |
| MDP0000199827 | MDP0000643415 | MDP0000188113 | MDP0000270104 | MDP0000314057 | MDP0000412607 | MDP0000816245 | |
| MDP0000327226 | MDP0000211739 | MDP0000855663 | MDP0000232789 | MDP0000924775 | MDP0000163618 | MDP0000127799 | |
| MDP0000338628 | MDP0000214084 | MDP0000254385 | MDP0000006982 | MDP0000779795 | MDP0000383060 | MDP0000901457 | |
| MDP0000306444 | MDP0000621375 | MDP0000172898 | MDP0000343887 | MDP0000320547 | MDP0000199686 | MDP0000861752 | |
| MDP0000432746 | MDP0000164657 | MDP0000131980 | MDP0000830926 | MDP0000529726 | MDP0000248687 | MDP0000621864 | |
| MDP0000352616 | MDP0000318338 | MDP0000420968 | MDP0000210893 | MDP0000276596 | MDP0000935322 | MDP0000247548 | |
| MDP0000579882 | MDP0000718454 | MDP0000696952 | MDP0000318732 | MDP0000133612 | MDP0000213245 | MDP0000231999 | |
| MDP0000193877 | MDP0000320982 | MDP0000170030 | MDP0000166574 | MDP0000175827 | MDP0000302009 | MDP0000165528 | |
| MDP0000499190 | MDP0000479140 | MDP0000259584 | MDP0000256645 | MDP0000271923 | MDP0000121203 | MDP0000201853 | |
| MDP0000302115 | MDP0000280819 | MDP0000758661 | MDP0000264160 | MDP0000288573 | MDP0000254705 | MDP0000309625 | |
| MDP0000171695 | MDP0000315158 | MDP0000230967 | MDP0000248776 | MDP0000183815 | MDP0000168762 | MDP0000304620 | |
| MDP0000316067 | MDP0000299992 | MDP0000289300 | MDP0000568581 | MDP0000163339 | MDP0000129331 | MDP0000195409 | |
| MDP0000146799 | MDP0000463166 | MDP0000307409 | MDP0000600288 | MDP0000315873 | MDP0000351321 | MDP0000342813 | |
| MDP0000732602 | MDP0000209731 | MDP0000767407 | MDP0000891077 | MDP0000708550 | MDP0000122849 | MDP0000321375 | |
| MDP0000280862 | MDP0000161703 | MDP0000316100 | MDP0000307728 | MDP0000450714 | MDP0000282305 | MDP0000187678 | |
| MDP0000193257 | MDP0000926233 | MDP0000809914 | MDP0000861495 | MDP0000265233 | MDP0000280440 | MDP0000245127 | |
| MDP0000661407 | MDP0000868659 | MDP0000485799 | MDP0000278269 | MDP0000452507 | MDP0000290819 | MDP0000190684 | |
| MDP0000243565 | MDP0000689939 | MDP0000242913 | MDP0000289226 | MDP0000232523 | MDP0000940179 | MDP0000310093 | |
| MDP0000738623 | MDP0000352240 | MDP0000358690 | MDP0000169888 | MDP0000683819 | MDP0000282143 | MDP0000238240 | |
| MDP0000159536 | MDP0000911973 | MDP0000529390 | MDP0000634433 | MDP0000255282 | MDP0000318068 | MDP0000759227 | |
| MDP0000688928 | MDP0000234595 | MDP0000267323 | MDP0000515017 | MDP0000131979 | MDP0000211685 | MDP0000231680 | |
| MDP0000887896 | MDP0000596868 | MDP0000242402 | MDP0000454710 | MDP0000123286 | MDP0000276120 | MDP0000847090 | |
| MDP0000169727 | MDP0000610308 | MDP0000273345 | MDP0000831154 | MDP0000345462 | MDP0000259977 | MDP0000540243 | |
| MDP0000364139 | MDP0000224010 | MDP0000295258 | MDP0000824430 | MDP0000158436 | MDP0000151832 | MDP0000194889 | |
| MDP0000142446 | MDP0000510503 | MDP0000602047 | MDP0000197200 | MDP0000532930 | MDP0000120224 | MDP0000132789 | |
| MDP0000464475 | MDP0000466196 | MDP0000152359 | MDP0000176991 | MDP0000312734 | MDP0000299953 | MDP0000196399 | |
| MDP0000294799 | MDP0000494715 | MDP0000478736 | MDP0000775934 | MDP0000531030 | MDP0000637150 | MDP0000794184 | |
| MDP0000178024 | MDP0000225194 | MDP0000928608 | MDP0000304816 | MDP0000187155 | MDP0000697206 | MDP0000174949 | |
| MDP0000236483 | MDP0000139736 | MDP0000278458 | MDP0000577829 | MDP0000173106 | MDP0000198539 | MDP0000784309 | |
| MDP0000402780 | MDP0000540171 | MDP0000823142 | MDP0000123004 | MDP0000903427 | MDP0000612660 | MDP0000200447 | |
| MDP0000145365 | MDP0000950298 | MDP0000234462 | MDP0000508389 | MDP0000451269 | MDP0000271925 | MDP0000136856 | |
| MDP0000805095 | MDP0000750449 | MDP0000292266 | MDP0000541905 | MDP0000214450 | MDP0000865961 | MDP0000578050 | |
| MDP0000166697 | MDP0000316241 | MDP0000235928 | MDP0000653439 | MDP0000320380 | MDP0000227323 | MDP0000167199 | |
| MDP0000542055 | MDP0000403071 | MDP0000183238 | MDP0000612129 | MDP0000672138 | MDP0000278072 | MDP0000262098 | |
| MDP0000197840 | MDP0000168904 | MDP0000613481 | MDP0000123802 | MDP0000127633 | MDP0000263736 | MDP0000164264 | |
| MDP0000215405 | MDP0000298623 | MDP0000929646 | MDP0000464636 | MDP0000600895 | MDP0000588230 | MDP0000920171 | |
| MDP0000733791 | MDP0000207303 | MDP0000218929 | MDP0000647176 | MDP0000172065 | MDP0000184960 | MDP0000426020 | |
| MDP0000189522 | MDP0000712699 | MDP0000130760 | MDP0000319582 | MDP0000313757 | MDP0000155446 | MDP0000323027 | |
| MDP0000833352 | MDP0000209790 | MDP0000145872 | MDP0000251018 | MDP0000319853 | MDP0000319815 | MDP0000939744 | |
| MDP0000517479 | MDP0000557365 | MDP0000120560 | MDP0000174326 | MDP0000169375 | MDP0000203221 | MDP0000906067 | |
| MDP0000177321 | MDP0000393709 | MDP0000225340 | MDP0000358977 | MDP0000261839 | MDP0000218018 | MDP0000120973 | |
| MDP0000562741 | MDP0000277463 | MDP0000262145 | MDP0000741380 | MDP0000742771 | MDP0000144837 | MDP0000917798 | |
| MDP0000260268 | MDP0000360208 | MDP0000172936 | MDP0000248694 | MDP0000925194 | MDP0000196174 | MDP0000308048 | |
| MDP0000286699 | MDP0000351118 | MDP0000512591 | MDP0000912917 | MDP0000300507 | MDP0000296668 | MDP0000119797 | |
| MDP0000157187 | MDP0000405592 | MDP0000221844 | MDP0000132702 | MDP0000434534 | MDP0000873874 | MDP0000128090 | |
| MDP0000223775 | MDP0000306672 | MDP0000309059 | MDP0000123391 | MDP0000252087 | MDP0000796508 | | |
| MDP0000309287 | MDP0000170290 | MDP0000366609 | MDP0000276798 | MDP0000917824 | MDP0000859800 | MDP0000294062 | |
| MDP0000510604 | MDP0000922476 | MDP0000841558 | MDP0000337136 | MDP0000184882 | MDP0000310619 | MDP0000436861 | |
| MDP0000501298 | MDP0000218824 | MDP0000284264 | MDP0000546892 | MDP0000633192 | MDP0000157816 | MDP0000670817 | |
| MDP0000939182 | MDP0000490694 | MDP0000163852 | MDP0000234651 | MDP0000542046 | MDP0000306556 | MDP0000045645 | |
| MDP0000441013 | MDP0000809715 | MDP0000142582 | MDP0000218940 | MDP0000144791 | MDP0000231030 | MDP0000783759 | |

TABLE 4-continued

Accession numbers (Velasco et al., 2010; Retrieved from the Internet: Rosaceae.org) of biomarker genes for superficial scald risk assessment during at-harvest. Higher or lower expression levels can result from cold stress resulting from storage imposition.

| | | | | | | |
|---|---|---|---|---|---|---|
| MDP0000389984 | MDP0000487437 | MDP0000170129 | MDP0000264606 | MDP0000203250 | MDP0000157932 | MDP0000375384 |
| MDP0000603853 | MDP0000349718 | MDP0000177244 | MDP0000675292 | MDP0000233708 | MDP0000240300 | MDP0000309183 |
| MDP0000336871 | MDP0000122022 | MDP0000348258 | MDP0000289855 | MDP0000606526 | MDP0000384845 | MDP0000197022 |
| MDP0000226432 | MDP0000886460 | MDP0000165352 | MDP0000616804 | MDP0000224773 | MDP0000266087 | MDP0000184553 |
| MDP0000200164 | MDP0000570178 | MDP0000130564 | MDP0000785092 | MDP0000589639 | MDP0000166780 | MDP0000166969 |
| MDP0000952085 | MDP0000312246 | MDP0000854686 | MDP0000270526 | MDP0000305932 | MDP0000802663 | MDP0000362019 |
| MDP0000137855 | MDP0000182956 | MDP0000293785 | MDP0000340511 | MDP0000209327 | MDP0000269911 | MDP0000208611 |
| MDP0000281967 | MDP0000216558 | MDP0000871412 | MDP0000374252 | MDP0000355705 | MDP0000296476 | MDP0000157854 |
| MDP0000127691 | MDP0000449389 | MDP0000865739 | MDP0000175733 | MDP0000063793 | MDP0000202911 | MDP0000130143 |
| MDP0000307308 | MDP0000314253 | MDP0000422549 | MDP0000944746 | MDP0000234477 | MDP0000203391 | MDP0000947876 |
| MDP0000786463 | MDP0000421226 | MDP0000853832 | MDP0000128423 | MDP0000232578 | MDP0000299496 | MDP0000271058 |
| MDP0000336256 | MDP0000143330 | MDP0000162194 | MDP0000933677 | MDP0000477856 | MDP0000138691 | MDP0000803090 |
| MDP0000305029 | MDP0000704254 | MDP0000369382 | MDP0000311632 | MDP0000206057 | MDP0000309995 | MDP0000233888 |
| MDP0000141097 | MDP0000198493 | MDP0000915501 | MDP0000315476 | MDP0000129681 | MDP0000525928 | MDP0000037251 |
| MDP0000196563 | MDP0000172885 | MDP0000127973 | MDP0000245162 | MDP0000890434 | MDP0000358829 | MDP0000341472 |
| MDP0000247681 | MDP0000303332 | MDP0000672731 | MDP0000195162 | MDP0000198166 | MDP0000358828 | MDP0000232846 |
| MDP0000136455 | MDP0000547461 | MDP0000921067 | MDP0000283994 | MDP0000198165 | MDP0000358827 | MDP0000212688 |
| MDP0000836170 | MDP0000157404 | MDP0000905321 | MDP0000269859 | MDP0000539433 | MDP0000218227 | MDP0000294789 |
| MDP0000253428 | MDP0000131100 | MDP0000892526 | MDP0000245245 | MDP0000309329 | MDP0000845428 | MDP0000178782 |
| MDP0000357423 | MDP0000144441 | MDP0000350201 | MDP0000123987 | MDP0000649828 | MDP0000171066 | MDP0000175282 |
| MDP0000476508 | MDP0000282829 | MDP0000244238 | MDP0000130016 | MDP0000353843 | MDP0000521965 | MDP0000473817 |
| MDP0000155077 | MDP0000827385 | MDP0000128581 | MDP0000263540 | MDP0000135731 | MDP0000703817 | MDP0000293103 |
| MDP0000347520 | MDP0000911025 | MDP0000759303 | MDP0000308446 | MDP0000307013 | MDP0000182253 | MDP0000347881 |
| MDP0000284819 | MDP0000151150 | MDP0000129926 | MDP0000536665 | MDP0000179767 | MDP0000147900 | MDP0000145027 |
| MDP0000153313 | MDP0000138241 | MDP0000338689 | MDP0000320119 | MDP0000927456 | MDP0000299015 | MDP0000192235 |
| MDP0000168725 | MDP0000217322 | MDP0000214291 | MDP0000270602 | MDP0000366710 | MDP0000248312 | MDP0000180024 |
| MDP0000225215 | MDP0000273029 | MDP0000156417 | MDP0000309477 | MDP0000169670 | MDP0000125171 | MDP0000204452 |
| MDP0000601282 | MDP0000122897 | MDP0000284030 | MDP0000909525 | MDP0000466284 | MDP0000319160 | MDP0000715969 |
| MDP0000712194 | MDP0000430717 | MDP0000901915 | MDP0000319434 | MDP0000284060 | MDP0000253891 | MDP0000345094 |
| MDP0000263628 | MDP0000288155 | MDP0000848695 | MDP0000184238 | MDP0000321380 | MDP0000607421 | MDP0000311110 |
| MDP0000463867 | MDP0000280105 | MDP0000237754 | MDP0000320056 | MDP0000262020 | MDP0000338804 | MDP0000666817 |
| MDP0000323375 | MDP0000940296 | MDP0000179659 | MDP0000412665 | MDP0000181372 | MDP0000312397 | MDP0000290889 |
| MDP0000158864 | MDP0000532093 | MDP0000242263 | MDP0000220347 | MDP0000750839 | MDP0000157962 | MDP0000811844 |
| MDP0000304763 | MDP0000163728 | MDP0000349199 | MDP0000314259 | MDP0000759782 | MDP0000127498 | MDP0000265213 |
| MDP0000202739 | MDP0000464599 | MDP0000317931 | MDP0000531930 | MDP0000281707 | MDP0000252478 | MDP0000201389 |
| MDP0000202282 | MDP0000186558 | MDP0000317621 | MDP0000280705 | MDP0000163771 | MDP0000274156 | MDP0000368785 |
| MDP0000174216 | MDP0000335354 | MDP0000427753 | MDP0000119925 | MDP0000265387 | MDP0000294667 | MDP0000191197 |
| MDP0000619638 | MDP0000237586 | MDP0000288670 | MDP0000319790 | MDP0000887754 | MDP0000318193 | MDP0000307516 |
| MDP0000503774 | MDP0000469664 | MDP0000138538 | MDP0000884147 | MDP0000815791 | MDP0000226601 | MDP0000202801 |
| MDP0000650358 | MDP0000126222 | MDP0000308563 | MDP0000390645 | MDP0000695737 | MDP0000394412 | MDP0000210087 |
| MDP0000540543 | MDP0000249284 | MDP0000132849 | MDP0000815097 | MDP0000128876 | MDP0000512808 | MDP0000229726 |
| MDP0000770369 | MDP0000192796 | MDP0000203347 | MDP0000672208 | MDP0000501447 | MDP0000206198 | MDP0000582861 |
| MDP0000282275 | MDP0000455726 | MDP0000228424 | MDP0000618272 | MDP0000250153 | MDP0000309575 | MDP0000392250 |
| MDP0000249539 | MDP0000275365 | MDP0000258078 | MDP0000349401 | MDP0000214532 | MDP0000813922 | MDP0000859897 |
| MDP0000257001 | MDP0000351483 | MDP0000543082 | MDP0000597996 | MDP0000161414 | MDP0000204437 | MDP0000123015 |
| MDP0000210684 | MDP0000176300 | MDP0000352413 | MDP0000741407 | MDP0000210970 | MDP0000171067 | MDP0000681724 |
| MDP0000473932 | MDP0000814937 | MDP0000300945 | MDP0000166861 | MDP0000443502 | MDP0000430870 | MDP0000844941 |
| MDP0000265810 | MDP0000153500 | MDP0000321445 | MDP0000167564 | MDP0000437672 | MDP0000225547 | |
| MDP0000137990 | MDP0000215281 | MDP0000836081 | MDP0000658885 | MDP0000287293 | MDP0000317819 | |
| MDP0000307857 | MDP0000203726 | MDP0000590966 | MDP0000706809 | MDP0000243937 | MDP0000205256 | |
| MDP0000679688 | MDP0000346532 | MDP0000740877 | MDP0000877316 | MDP0000408508 | MDP0000361511 | |
| MDP0000790026 | MDP0000415189 | MDP0000244886 | MDP0000410116 | MDP0000288633 | MDP0000206985 | |
| MDP0000283898 | MDP0000225170 | MDP0000285682 | MDP0000287729 | MDP0000118810 | MDP0000581272 | |
| MDP0000292276 | MDP0000308201 | MDP0000818140 | MDP0000497915 | MDP0000830519 | MDP0000178513 | |

TABLE 5

Accession numbers (Velasco et al., 2010; Retrieved from the Internet: Rosaceae.org) of biomarker genes for superficial scald risk assessment during cold storage. Biomarker expression levels increase as risk of developing superficial scald increases.

| | | | | | | |
|---|---|---|---|---|---|---|
| MDP0000595271 | MDP0000231076 | MDP0000199110 | MDP0000153000 | MDP0000568825 | MDP0000593593 | MDP0000289804 |
| MDP0000868045 | MDP0000416548 | MDP0000532986 | MDP0000258908 | MDP0000197984 | MDP0000194046 | MDP0000148178 |
| MDP0000188613 | MDP0000899821 | MDP0000719836 | MDP0000299801 | MDP0000178304 | MDP0000404409 | MDP0000210595 |
| MDP0000266097 | MDP0000755113 | MDP0000261679 | MDP0000307124 | MDP0000380032 | MDP0000170792 | MDP0000267350 |
| MDP0000243843 | MDP0000242622 | MDP0000507003 | MDP0000908881 | MDP0000298232 | MDP0000726332 | MDP0000254208 |
| MDP0000209662 | MDP0000250936 | MDP0000737001 | MDP0000487738 | MDP0000144205 | MDP0000131645 | MDP0000326412 |
| MDP0000288533 | MDP0000508761 | MDP0000166704 | MDP0000487946 | MDP0000864442 | MDP0000195510 | MDP0000150480 |
| MDP0000511650 | MDP0000825508 | MDP0000142251 | MDP0000151829 | MDP0000867150 | MDP0000281064 | MDP0000137225 |
| MDP0000279839 | MDP0000231666 | MDP0000192074 | MDP0000119634 | MDP0000599845 | MDP0000257010 | MDP0000296432 |
| MDP0000162146 | MDP0000267909 | MDP0000251656 | MDP0000419926 | MDP0000803862 | MDP0000886270 | MDP0000150841 |

TABLE 5-continued

Accession numbers (Velasco et al., 2010; Retrieved from the Internet: Rosaceae.org) of biomarker genes for superficial scald risk assessment during cold storage. Biomarker expression levels increase as risk of developing superficial scald increases.

| | | | | | | | |
|---|---|---|---|---|---|---|---|
| MDP0000745371 | MDP0000342540 | MDP0000825373 | MDP0000194902 | MDP0000216945 | MDP0000711379 | MDP0000313224 |
| MDP0000217451 | MDP0000327191 | MDP0000509613 | MDP0000218404 | MDP0000235548 | MDP0000278477 | MDP0000829416 |
| MDP0000228499 | MDP0000471879 | MDP0000771404 | MDP0000526802 | MDP0000213526 | MDP0000913661 | MDP0000123888 |
| MDP0000759646 | MDP0000127244 | MDP0000307340 | MDP0000242083 | MDP0000199076 | MDP0000666771 | MDP0000633461 |
| MDP0000323702 | MDP0000792088 | MDP0000564334 | MDP0000187493 | MDP0000452083 | MDP0000261468 | MDP0000183814 |
| MDP0000182342 | MDP0000582214 | MDP0000198406 | MDP0000425918 | MDP0000172542 | MDP0000211356 | MDP0000570881 |
| MDP0000219062 | MDP0000668140 | MDP0000390049 | MDP0000431280 | MDP0000285612 | MDP0000921402 | MDP0000226995 |
| MDP0000216638 | MDP0000271312 | MDP0000313778 | MDP0000265094 | MDP0000420611 | MDP0000437033 | MDP0000251966 |
| MDP0000913598 | MDP0000161016 | MDP0000251516 | MDP0000572564 | MDP0000300811 | MDP0000200811 | MDP0000716496 |
| MDP0000906115 | MDP0000739955 | MDP0000186193 | MDP0000881966 | MDP0000233842 | MDP0000253215 | MDP0000256573 |
| MDP0000523579 | MDP0000715270 | MDP0000200799 | MDP0000291687 | MDP0000459010 | MDP0000127739 | MDP0000219838 |
| MDP0000782085 | MDP0000319910 | MDP0000252171 | MDP0000210560 | MDP0000663105 | MDP0000628093 | MDP0000173635 |
| MDP0000140483 | MDP0000137919 | MDP0000205035 | MDP0000148289 | MDP0000120413 | MDP0000812018 | MDP0000163017 |
| MDP0000450991 | MDP0000188101 | MDP0000135974 | MDP0000285672 | MDP0000205216 | MDP0000168714 | MDP0000323136 |
| MDP0000287302 | MDP0000786311 | MDP0000284571 | MDP0000175733 | MDP0000223003 | MDP0000149907 | MDP0000576205 |
| MDP0000298230 | MDP0000420223 | MDP0000434420 | MDP0000192671 | MDP0000158470 | MDP0000638442 | MDP0000258979 |
| MDP0000292031 | MDP0000697764 | MDP0000566567 | MDP0000319522 | MDP0000760179 | MDP0000515106 | MDP0000311720 |
| MDP0000295562 | MDP0000151884 | MDP0000545379 | MDP0000278157 | MDP0000756254 | MDP0000325497 | MDP0000222790 |
| MDP0000899351 | MDP0000298062 | MDP0000211549 | MDP0000191837 | MDP0000679369 | MDP0000707567 | MDP0000297105 |
| MDP0000191661 | MDP0000858175 | MDP0000202051 | MDP0000193898 | MDP0000369596 | MDP0000767257 | MDP0000506825 |
| MDP0000759591 | MDP0000839921 | MDP0000699004 | MDP0000120546 | MDP0000532630 | MDP0000568474 | MDP0000159103 |
| MDP0000586674 | MDP0000152670 | MDP0000246484 | MDP0000294847 | MDP0000608985 | MDP0000255415 | MDP0000160390 |
| MDP0000175691 | MDP0000569069 | MDP0000223057 | MDP0000156554 | MDP0000696814 | MDP0000212925 | MDP0000313485 |
| MDP0000230387 | MDP0000804928 | MDP0000162215 | MDP0000570395 | MDP0000374719 | MDP0000490696 | MDP0000279462 |
| MDP0000264639 | MDP0000125618 | MDP0000186011 | MDP0000201196 | MDP0000263161 | MDP0000578396 | MDP0000839209 |
| MDP0000649783 | MDP0000713068 | MDP0000139458 | MDP0000554480 | MDP0000263768 | MDP0000698220 | MDP0000148399 |
| MDP0000548790 | MDP0000142250 | MDP0000629887 | MDP0000209821 | MDP0000836661 | MDP0000286238 | MDP0000305699 |
| MDP0000645274 | MDP0000264441 | MDP0000875406 | MDP0000735747 | MDP0000237989 | MDP0000147814 | MDP0000864660 |
| MDP0000157209 | MDP0000129648 | MDP0000265644 | MDP0000862169 | MDP0000207066 | MDP0000294725 | MDP0000884047 |
| MDP0000278858 | MDP0000249405 | MDP0000305630 | MDP0000674589 | MDP0000316162 | MDP0000137211 | MDP0000275507 |
| MDP0000307943 | MDP0000148746 | MDP0000253802 | MDP0000279440 | MDP0000173593 | MDP0000163095 | MDP0000798346 |
| MDP0000126517 | MDP0000129626 | MDP0000232042 | MDP0000322404 | MDP0000407300 | MDP0000336146 | MDP0000142278 |
| MDP0000418277 | MDP0000288378 | MDP0000576110 | MDP0000680345 | MDP0000010587 | MDP0000181915 | MDP0000126274 |
| MDP0000298577 | MDP0000431556 | MDP0000122993 | MDP0000829170 | MDP0000899508 | MDP0000718806 | MDP0000222189 |
| MDP0000297821 | MDP0000127134 | MDP0000217423 | MDP0000314043 | MDP0000227115 | MDP0000885737 | MDP0000478232 |
| MDP0000197160 | MDP0000805606 | MDP0000276506 | MDP0000951901 | MDP0000417791 | MDP0000310641 | MDP0000582841 |
| MDP0000274090 | MDP0000300045 | MDP0000160434 | MDP0000431120 | MDP0000184528 | MDP0000589981 | MDP0000673917 |
| MDP0000140386 | MDP0000126570 | MDP0000310866 | MDP0000770211 | MDP0000133801 | MDP0000153532 | MDP0000718381 |
| MDP0000659260 | MDP0000192078 | MDP0000137826 | MDP0000206991 | MDP0000543167 | MDP0000176441 | MDP0000302538 |
| MDP0000150279 | MDP0000575170 | MDP0000350845 | MDP0000287264 | MDP0000205588 | MDP0000167199 | MDP0000119590 |
| MDP0000123893 | MDP0000585849 | MDP0000305384 | MDP0000338147 | MDP0000281804 | MDP0000119754 | MDP0000257423 |
| MDP0000123894 | MDP0000153831 | MDP0000202780 | MDP0000242255 | MDP0000136653 | MDP0000307516 | MDP0000118790 |
| MDP0000309383 | MDP0000161424 | MDP0000316694 | MDP0000163217 | MDP0000390252 | MDP0000884108 | MDP0000174365 |
| MDP0000154589 | MDP0000248504 | MDP0000863049 | MDP0000180877 | MDP0000164511 | MDP0000181206 | MDP0000547418 |
| MDP0000233761 | MDP0000394116 | MDP0000140755 | MDP0000304795 | MDP0000199010 | MDP0000563553 | MDP0000194040 |
| MDP0000171771 | MDP0000454229 | MDP0000415910 | MDP0000337931 | MDP0000866259 | MDP0000210996 | MDP0000251295 |
| MDP0000245234 | MDP0000124626 | MDP0000947607 | MDP0000323033 | MDP0000484484 | MDP0000880784 | MDP0000922391 |
| MDP0000740656 | MDP0000247130 | MDP0000260159 | MDP0000215049 | MDP0000641583 | MDP0000461727 | MDP0000180642 |
| MDP0000455516 | MDP0000320477 | MDP0000231346 | MDP0000215190 | MDP0000453192 | MDP0000160547 | MDP0000270644 |
| MDP0000271781 | MDP0000633953 | MDP0000293001 | MDP0000128089 | MDP0000119512 | MDP0000310001 | MDP0000272396 |
| MDP0000479863 | MDP0000251955 | MDP0000273029 | MDP0000229280 | MDP0000755938 | MDP0000841490 | MDP0000297304 |
| MDP0000488789 | MDP0000163690 | MDP0000230627 | MDP0000241967 | MDP0000222539 | MDP0000309587 | MDP0000805778 |
| MDP0000196402 | MDP0000175240 | MDP0000253952 | MDP0000202439 | MDP0000229843 | MDP0000129379 | MDP0000240930 |
| MDP0000398765 | MDP0000131182 | MDP0000264920 | MDP0000214697 | MDP0000333250 | MDP0000246999 | MDP0000263706 |
| MDP0000193050 | MDP0000173687 | MDP0000255777 | MDP0000162375 | MDP0000850015 | MDP0000610787 | MDP0000192492 |
| MDP0000279713 | MDP0000512061 | MDP0000269554 | MDP0000188229 | MDP0000255915 | MDP0000265042 | MDP0000719386 |
| MDP0000236634 | MDP0000617396 | MDP0000695252 | MDP0000221319 | MDP0000143011 | MDP0000129167 | MDP0000308284 |
| MDP0000223496 | MDP0000794656 | MDP0000301420 | MDP0000212713 | MDP0000127028 | MDP0000176769 | MDP0000162481 |
| MDP0000663049 | MDP0000843477 | MDP0000169686 | MDP0000179238 | MDP0000909653 | MDP0000124428 | MDP0000841118 |
| MDP0000663236 | MDP0000313248 | MDP0000180684 | MDP0000928674 | MDP0000692392 | MDP0000317974 | MDP0000185324 |
| MDP0000178522 | MDP0000286385 | MDP0000185304 | MDP0000584567 | MDP0000256726 | MDP0000202352 | MDP0000302858 |
| MDP0000275424 | MDP0000171719 | MDP0000299702 | MDP0000210562 | MDP0000210067 | MDP0000767331 | MDP0000268763 |
| MDP0000167207 | MDP0000709303 | MDP0000282415 | MDP0000127563 | MDP0000156421 | MDP0000205389 | MDP0000004754 |
| MDP0000241046 | MDP0000134135 | MDP0000468038 | MDP0000291544 | MDP0000304817 | MDP0000166723 | MDP0000160413 |
| MDP0000295604 | MDP0000680183 | MDP0000174149 | MDP0000863151 | MDP0000285243 | MDP0000121656 | MDP0000162600 |
| MDP0000131308 | MDP0000747526 | MDP0000261432 | MDP0000208546 | MDP0000121669 | MDP0000146135 | MDP0000164159 |
| MDP0000431281 | MDP0000243676 | MDP0000216602 | MDP0000543088 | MDP0000279550 | MDP0000165503 | MDP0000342721 |
| MDP0000532631 | MDP0000731356 | MDP0000639167 | MDP0000660892 | MDP0000732635 | MDP0000146390 | MDP0000321664 |
| MDP0000328533 | MDP0000012541 | MDP0000687873 | MDP0000882895 | MDP0000160662 | MDP0000133428 | MDP0000192847 |
| MDP0000865079 | MDP0000138296 | MDP0000289339 | MDP0000219521 | MDP0000226405 | MDP0000375867 | MDP0000159140 |
| MDP0000242052 | MDP0000269900 | MDP0000802413 | MDP0000276576 | MDP0000252597 | MDP0000720497 | MDP0000144324 |
| MDP0000314081 | MDP0000199234 | MDP0000723934 | MDP0000672731 | MDP0000253189 | MDP0000155746 | MDP0000196869 |
| MDP0000133671 | MDP0000162721 | MDP0000298547 | MDP0000231093 | MDP0000157089 | MDP0000933945 | MDP0000668914 |
| MDP0000585014 | MDP0000126098 | MDP0000900186 | MDP0000297797 | MDP0000201903 | MDP0000270083 | MDP0000225047 |
| MDP0000917197 | MDP0000123910 | MDP0000736035 | MDP0000257119 | MDP0000228838 | MDP0000176923 | MDP0000618087 |

TABLE 5-continued

Accession numbers (Velasco et al., 2010; Retrieved from the Internet: Rosaceae.org) of biomarker genes for superficial scald risk assessment during cold storage. Biomarker expression levels increase as risk of developing superficial scald increases.

| | | | | | | |
|---|---|---|---|---|---|---|
| MDP0000126873 | MDP0000157408 | MDP0000363760 | MDP0000157879 | MDP0000318500 | MDP0000304378 | MDP0000184157 |
| MDP0000292176 | MDP0000119600 | MDP0000129506 | MDP0000421759 | MDP0000167088 | MDP0000831840 | MDP0000189570 |
| MDP0000230316 | MDP0000204626 | MDP0000873295 | MDP0000320322 | MDP0000311389 | MDP0000599427 | MDP0000722934 |
| MDP0000218952 | MDP0000601893 | MDP0000009080 | MDP0000279360 | MDP0000776146 | MDP0000144640 | MDP0000279785 |
| MDP0000192816 | MDP0000196627 | MDP0000806350 | MDP0000321558 | MDP0000163006 | MDP0000182333 | MDP0000241928 |
| MDP0000300351 | MDP0000679687 | MDP0000648218 | MDP0000131377 | MDP0000775613 | MDP0000164161 | MDP0000440918 |
| MDP0000812560 | MDP0000184480 | MDP0000175141 | MDP0000531811 | MDP0000228304 | MDP0000190430 | MDP0000274901 |
| MDP0000012534 | MDP0000195070 | MDP0000184238 | MDP0000609114 | MDP0000891965 | MDP0000175839 | MDP0000298769 |
| MDP0000268320 | MDP0000757070 | MDP0000135041 | MDP0000205725 | MDP0000131763 | MDP0000138284 | MDP0000215026 |
| MDP0000276264 | MDP0000832469 | MDP0000262811 | MDP0000202900 | MDP0000242266 | MDP0000318293 | MDP0000328419 |
| MDP0000711374 | MDP0000788707 | MDP0000163669 | | | | MDP0000134278 |
| MDP0000131004 | MDP0000130822 | MDP0000897807 | | | | |
| MDP0000227886 | MDP0000122413 | MDP0000269136 | | | | |
| MDP0000882268 | MDP0000130200 | MDP0000734649 | | | | |
| MDP0000199661 | MDP0000318900 | MDP0000677352 | | | | |
| MDP0000155809 | MDP0000296600 | MDP0000241462 | | | | |
| MDP0000689033 | MDP0000720974 | MDP0000238976 | | | | |
| MDP0000213383 | MDP0000306888 | MDP0000125850 | | | | |

Firm flesh browning disorder can be controlled using appropriate storage conditions. We were able to use these methods to discover putative biomarkers, since different treatments following harvest, induce contrasting disorder development. Controlled atmosphere combined with lower temperature (0.5° C.) storage causes increased injury over that observed at warmer storage temperature (3.0° C.). In addition, treatment of apples with 1-MCP (SmartFresh) following harvest also enhances firm flesh browning injury. Candidate biomarker genes were selected by pairwise comparison using the differential gene expression program edgeR (R, Bioconductor) with a p-value cut off of 0.05. Genes were selected from cortex/flesh tissue collected from New York state grown 'Empire' apples, provoked by storage treatments that affect firm flesh browning injury incidence. From a total of 63541 gene models, 2581 had an expression change of at least 4-fold, and had an average expression RPKM value of at least 1 per sample, and were selected as potential predictive or diagnostic biomarkers for firm flesh browning (Table 6).

TABLE 6

Accession numbers (Velasco et al., 2010; Retrieved from the Internet: Rosaceae.org) of biomarker genes for firm flesh browning risk assessment during cold storage. Higher or lower expression levels can result from cold stress resulting from storage imposition.

| | | | | | | |
|---|---|---|---|---|---|---|
| MDP0000034165 | MDP0000312902 | MDP0000133552 | MDP0000218946 | MDP0000310711 | MDP0000716315 | MDP0000234244 |
| MDP0000060869 | MDP0000313281 | MDP0000134105 | MDP0000219155 | MDP0000311039 | MDP0000720656 | MDP0000234570 |
| MDP0000074782 | MDP0000313454 | MDP0000134162 | MDP0000220129 | MDP0000311884 | MDP0000720974 | MDP0000234689 |
| MDP0000085889 | MDP0000314088 | MDP0000134341 | MDP0000220168 | MDP0000312044 | MDP0000722139 | MDP0000235112 |
| MDP0000085893 | MDP0000314777 | MDP0000134389 | MDP0000220633 | MDP0000312397 | MDP0000722229 | MDP0000235661 |
| MDP0000086296 | MDP0000317237 | MDP0000134603 | MDP0000221075 | MDP0000312434 | MDP0000727570 | MDP0000235822 |
| MDP0000088659 | MDP0000317475 | MDP0000135374 | MDP0000221400 | MDP0000313382 | MDP0000729533 | MDP0000237637 |
| MDP0000092478 | MDP0000317502 | MDP0000135529 | MDP0000221435 | MDP0000313664 | MDP0000731537 | MDP0000238100 |
| MDP0000119926 | MDP0000318069 | MDP0000135540 | MDP0000221742 | MDP0000313949 | MDP0000731637 | MDP0000239011 |
| MDP0000120188 | MDP0000318184 | MDP0000135831 | MDP0000221867 | MDP0000314286 | MDP0000732666 | MDP0000239029 |
| MDP0000120975 | MDP0000318347 | MDP0000135974 | MDP0000222184 | MDP0000314435 | MDP0000732713 | MDP0000240138 |
| MDP0000121374 | MDP0000318613 | MDP0000136892 | MDP0000222403 | MDP0000314478 | MDP0000736385 | MDP0000241650 |
| MDP0000121657 | MDP0000319048 | MDP0000137225 | MDP0000222430 | MDP0000314505 | MDP0000736490 | MDP0000241840 |
| MDP0000121897 | MDP0000320017 | MDP0000137705 | MDP0000223153 | MDP0000315227 | MDP0000742957 | MDP0000242052 |
| MDP0000122086 | MDP0000320496 | MDP0000137792 | MDP0000223422 | MDP0000315498 | MDP0000744636 | MDP0000242083 |
| MDP0000122235 | MDP0000320534 | MDP0000138035 | MDP0000223749 | MDP0000315959 | MDP0000745371 | MDP0000243721 |
| MDP0000122297 | MDP0000320763 | MDP0000138500 | MDP0000223871 | MDP0000315998 | MDP0000746166 | MDP0000244067 |
| MDP0000122540 | MDP0000321910 | MDP0000138538 | MDP0000223878 | MDP0000316002 | MDP0000746652 | MDP0000244851 |
| MDP0000124008 | MDP0000322034 | MDP0000138727 | MDP0000224040 | MDP0000316095 | MDP0000747845 | MDP0000245067 |
| MDP0000124585 | MDP0000322229 | MDP0000138729 | MDP0000224773 | MDP0000316207 | MDP0000748035 | MDP0000245173 |
| MDP0000125807 | MDP0000322543 | MDP0000138789 | MDP0000225212 | MDP0000316310 | MDP0000749755 | MDP0000245245 |
| MDP0000126274 | MDP0000322563 | MDP0000139058 | MDP0000225313 | MDP0000316379 | MDP0000750374 | MDP0000245702 |
| MDP0000126479 | MDP0000323033 | MDP0000139525 | MDP0000225502 | MDP0000316397 | MDP0000753547 | MDP0000245760 |
| MDP0000126481 | MDP0000324254 | MDP0000139721 | MDP0000225524 | MDP0000316490 | MDP0000754524 | MDP0000245817 |
| MDP0000126601 | MDP0000324681 | MDP0000140046 | MDP0000225569 | MDP0000316497 | MDP0000755474 | MDP0000246198 |
| MDP0000127732 | MDP0000324831 | MDP0000140259 | MDP0000226247 | MDP0000317227 | MDP0000755567 | MDP0000247211 |
| MDP0000128678 | MDP0000325376 | MDP0000141463 | MDP0000226279 | MDP0000317247 | MDP0000756536 | MDP0000248168 |
| MDP0000128887 | MDP0000325652 | MDP0000141686 | MDP0000227119 | MDP0000317975 | MDP0000757613 | MDP0000249105 |
| MDP0000129164 | MDP0000326734 | MDP0000142080 | MDP0000227640 | MDP0000318256 | MDP0000758050 | MDP0000249183 |
| MDP0000129874 | MDP0000330372 | MDP0000142814 | MDP0000227657 | MDP0000318702 | MDP0000761113 | MDP0000249561 |
| MDP0000130244 | MDP0000331536 | MDP0000143458 | MDP0000228070 | MDP0000318866 | MDP0000762600 | MDP0000250254 |
| MDP0000130449 | MDP0000337873 | MDP0000143462 | MDP0000228247 | MDP0000318901 | MDP0000766223 | MDP0000250737 |
| MDP0000130822 | MDP0000343219 | MDP0000143463 | MDP0000228302 | MDP0000319037 | MDP0000766240 | MDP0000250951 |

TABLE 6-continued

Accession numbers (Velasco et al., 2010; Retrieved from the Internet: Rosaceae.org) of biomarker genes for firm flesh browning risk assessment during cold storage. Higher or lower expression levels can result from cold stress resulting from storage imposition.

| | | | | | | | |
|---|---|---|---|---|---|---|---|
| MDP0000131763 | MDP0000345457 | MDP0000143641 | MDP0000228370 | MDP0000319081 | MDP0000769764 | MDP0000251418 | |
| MDP0000132130 | MDP0000347092 | MDP0000143660 | MDP0000228456 | MDP0000319220 | MDP0000771574 | MDP0000251943 | |
| MDP0000132621 | MDP0000349267 | MDP0000144125 | MDP0000228682 | MDP0000319299 | MDP0000771647 | MDP0000253102 | |
| MDP0000132919 | MDP0000355705 | MDP0000144481 | MDP0000228839 | MDP0000319525 | MDP0000772938 | MDP0000253735 | |
| MDP0000133105 | MDP0000362571 | MDP0000145375 | MDP0000228855 | MDP0000320124 | MDP0000773753 | MDP0000254009 | |
| MDP0000133306 | MDP0000363287 | MDP0000145885 | MDP0000229280 | MDP0000320167 | MDP0000774713 | MDP0000255255 | |
| MDP0000133507 | MDP0000364685 | MDP0000146158 | MDP0000229796 | MDP0000320213 | MDP0000776040 | MDP0000256494 | |
| MDP0000133792 | MDP0000365521 | MDP0000146168 | MDP0000230223 | MDP0000320322 | MDP0000776042 | MDP0000257010 | |
| MDP0000133933 | MDP0000365970 | MDP0000146360 | MDP0000230627 | MDP0000320555 | MDP0000777336 | MDP0000257349 | |
| MDP0000134325 | MDP0000367733 | MDP0000146703 | MDP0000230863 | MDP0000321078 | MDP0000780674 | MDP0000257866 | |
| MDP0000136194 | MDP0000367954 | MDP0000147795 | MDP0000231468 | MDP0000321156 | MDP0000781875 | MDP0000258775 | |
| MDP0000136671 | MDP0000376209 | MDP0000147872 | MDP0000231923 | MDP0000321410 | MDP0000782085 | MDP0000259832 | |
| MDP0000136708 | MDP0000376261 | MDP0000147902 | MDP0000231962 | MDP0000321690 | MDP0000785886 | MDP0000259869 | |
| MDP0000137053 | MDP0000379414 | MDP0000147913 | MDP0000231999 | MDP0000321770 | MDP0000786650 | MDP0000260553 | |
| MDP0000137211 | MDP0000385086 | MDP0000148067 | MDP0000232225 | MDP0000322053 | MDP0000787216 | MDP0000261517 | |
| MDP0000137305 | MDP0000388415 | MDP0000148081 | MDP0000232344 | MDP0000322220 | MDP0000788345 | MDP0000261585 | |
| MDP0000137383 | MDP0000390049 | MDP0000148121 | MDP0000232477 | MDP0000323076 | MDP0000789304 | MDP0000262078 | |
| MDP0000137468 | MDP0000391295 | MDP0000148283 | MDP0000232855 | MDP0000323136 | MDP0000789873 | MDP0000262449 | |
| MDP0000138581 | MDP0000392201 | MDP0000148399 | MDP0000232990 | MDP0000323702 | MDP0000792088 | MDP0000262682 | |
| MDP0000138927 | MDP0000392485 | MDP0000148493 | MDP0000233154 | MDP0000324894 | MDP0000793733 | MDP0000263016 | |
| MDP0000139052 | MDP0000393617 | MDP0000148685 | MDP0000233370 | MDP0000325984 | MDP0000794439 | MDP0000263035 | |
| MDP0000139075 | MDP0000394116 | MDP0000148780 | MDP0000233440 | MDP0000326334 | MDP0000795437 | MDP0000263180 | |
| MDP0000139458 | MDP0000398063 | MDP0000148815 | MDP0000233508 | MDP0000326412 | MDP0000800300 | MDP0000263415 | |
| MDP0000140074 | MDP0000399807 | MDP0000148967 | MDP0000233546 | MDP0000328563 | MDP0000803096 | MDP0000264639 | |
| MDP0000140483 | MDP0000405003 | MDP0000149839 | MDP0000233923 | MDP0000330325 | MDP0000803411 | MDP0000264686 | |
| MDP0000140678 | MDP0000406592 | MDP0000149857 | MDP0000234782 | MDP0000334047 | MDP0000803920 | MDP0000266249 | |
| MDP0000140803 | MDP0000409061 | MDP0000149950 | MDP0000235028 | MDP0000334395 | MDP0000804605 | MDP0000266692 | |
| MDP0000142389 | MDP0000409732 | MDP0000150049 | MDP0000235118 | MDP0000334726 | MDP0000804895 | MDP0000268731 | |
| MDP0000143220 | MDP0000411091 | MDP0000150374 | MDP0000235322 | MDP0000337611 | MDP0000804928 | MDP0000269052 | |
| MDP0000144836 | MDP0000412849 | MDP0000150382 | MDP0000236866 | MDP0000338804 | MDP0000808124 | MDP0000269215 | |
| MDP0000145104 | MDP0000413399 | MDP0000150637 | MDP0000237173 | MDP0000342145 | MDP0000811831 | MDP0000270052 | |
| MDP0000145267 | MDP0000414977 | MDP0000150710 | MDP0000237180 | MDP0000343244 | MDP0000812208 | MDP0000270057 | |
| MDP0000145559 | MDP0000418277 | MDP0000150868 | MDP0000237619 | MDP0000343311 | MDP0000813838 | MDP0000270440 | |
| MDP0000145813 | MDP0000420611 | MDP0000151330 | MDP0000238096 | MDP0000343606 | MDP0000817733 | MDP0000270449 | |
| MDP0000145827 | MDP0000423597 | MDP0000152377 | MDP0000238773 | MDP0000344348 | MDP0000818877 | MDP0000270534 | |
| MDP0000146449 | MDP0000427970 | MDP0000152433 | MDP0000238780 | MDP0000347336 | MDP0000819360 | MDP0000271403 | |
| MDP0000146709 | MDP0000436345 | MDP0000152612 | MDP0000238942 | MDP0000348468 | MDP0000821066 | MDP0000271527 | |
| MDP0000146914 | MDP0000436890 | MDP0000152670 | MDP0000238996 | MDP0000349972 | MDP0000821241 | MDP0000271850 | |
| MDP0000147150 | MDP0000440922 | MDP0000153237 | MDP0000239442 | MDP0000350579 | MDP0000822659 | MDP0000272179 | |
| MDP0000147635 | MDP0000445218 | MDP0000153265 | MDP0000239687 | MDP0000356203 | MDP0000822752 | MDP0000272619 | |
| MDP0000147638 | MDP0000447081 | MDP0000153381 | MDP0000239820 | MDP0000356350 | MDP0000823488 | MDP0000273276 | |
| MDP0000148169 | MDP0000450991 | MDP0000153759 | MDP0000240094 | MDP0000360018 | MDP0000825508 | MDP0000273370 | |
| MDP0000148746 | MDP0000451434 | MDP0000153798 | MDP0000240378 | MDP0000360295 | MDP0000825698 | MDP0000274120 | |
| MDP0000150068 | MDP0000452083 | MDP0000154393 | MDP0000240458 | MDP0000361351 | MDP0000826832 | MDP0000275058 | |
| MDP0000150990 | MDP0000453114 | MDP0000154734 | MDP0000240463 | MDP0000361550 | MDP0000827219 | MDP0000275110 | |
| MDP0000151825 | MDP0000453295 | MDP0000155073 | MDP0000241545 | MDP0000361899 | MDP0000827463 | MDP0000275386 | |
| MDP0000152278 | MDP0000455174 | MDP0000155206 | MDP0000241587 | MDP0000361922 | MDP0000827881 | MDP0000275850 | |
| MDP0000152821 | MDP0000457243 | MDP0000155869 | MDP0000241662 | MDP0000362033 | MDP0000830926 | MDP0000276013 | |
| MDP0000155194 | MDP0000459304 | MDP0000156213 | MDP0000241694 | MDP0000362294 | MDP0000831656 | MDP0000277046 | |
| MDP0000156208 | MDP0000460051 | MDP0000156301 | MDP0000241913 | MDP0000362615 | MDP0000832104 | MDP0000277802 | |
| MDP0000156830 | MDP0000460658 | MDP0000156379 | MDP0000242154 | MDP0000363386 | MDP0000832599 | MDP0000279125 | |
| MDP0000157932 | MDP0000461150 | MDP0000156554 | MDP0000242476 | MDP0000364779 | MDP0000834632 | MDP0000279459 | |
| MDP0000158046 | MDP0000462139 | MDP0000156921 | MDP0000242498 | MDP0000365732 | MDP0000835304 | MDP0000280264 | |
| MDP0000158047 | MDP0000463271 | MDP0000157113 | MDP0000242884 | MDP0000366710 | MDP0000836051 | MDP0000280711 | |
| MDP0000158129 | MDP0000465035 | MDP0000157124 | MDP0000242979 | MDP0000368719 | MDP0000837613 | MDP0000280712 | |
| MDP0000158544 | MDP0000471879 | MDP0000157238 | MDP0000243120 | MDP0000371737 | MDP0000839696 | MDP0000281041 | |
| MDP0000158753 | MDP0000472176 | MDP0000157356 | MDP0000243138 | MDP0000372629 | MDP0000839736 | MDP0000281698 | |
| MDP0000159000 | MDP0000473750 | MDP0000157412 | MDP0000243826 | MDP0000375867 | MDP0000840536 | MDP0000282696 | |
| MDP0000159240 | MDP0000481448 | MDP0000157748 | MDP0000244084 | MDP0000376347 | MDP0000841170 | MDP0000282889 | |
| MDP0000160072 | MDP0000482268 | MDP0000158045 | MDP0000244211 | MDP0000376469 | MDP0000843913 | MDP0000284060 | |
| MDP0000160662 | MDP0000484559 | MDP0000158089 | MDP0000244504 | MDP0000378200 | MDP0000844682 | MDP0000285300 | |
| MDP0000161415 | MDP0000484742 | MDP0000158114 | MDP0000244591 | MDP0000379060 | MDP0000848372 | MDP0000286125 | |
| MDP0000161424 | MDP0000488361 | MDP0000158194 | MDP0000244700 | MDP0000379961 | MDP0000848905 | MDP0000286764 | |
| MDP0000162064 | MDP0000498540 | MDP0000158387 | MDP0000244928 | MDP0000382467 | MDP0000854242 | MDP0000287857 | |
| MDP0000162679 | MDP0000501048 | MDP0000158437 | MDP0000245016 | MDP0000383616 | MDP0000854432 | MDP0000288468 | |
| MDP0000163006 | MDP0000503246 | MDP0000158799 | MDP0000245123 | MDP0000383777 | MDP0000854581 | MDP0000289320 | |
| MDP0000163728 | MDP0000506346 | MDP0000159472 | MDP0000245234 | MDP0000385168 | MDP0000857061 | MDP0000290315 | |
| MDP0000164386 | MDP0000506359 | MDP0000159766 | MDP0000245436 | MDP0000386613 | MDP0000858039 | MDP0000290615 | |
| MDP0000166059 | MDP0000507003 | MDP0000159814 | MDP0000245720 | MDP0000388769 | MDP0000860226 | MDP0000291422 | |
| MDP0000166590 | MDP0000507853 | MDP0000159873 | MDP0000245931 | MDP0000389735 | MDP0000861708 | MDP0000292157 | |
| MDP0000166704 | MDP0000513880 | MDP0000160029 | MDP0000246046 | MDP0000391210 | MDP0000864575 | MDP0000292767 | |
| MDP0000166723 | MDP0000517479 | MDP0000160094 | MDP0000247502 | MDP0000394728 | MDP0000864748 | MDP0000292984 | |
| MDP0000168498 | MDP0000520923 | MDP0000160435 | MDP0000247659 | MDP0000394944 | MDP0000865032 | MDP0000293347 | |
| MDP0000168964 | MDP0000521662 | MDP0000160447 | MDP0000248299 | MDP0000397579 | MDP0000865079 | MDP0000293642 | |
| MDP0000169611 | MDP0000521934 | MDP0000160481 | MDP0000248312 | MDP0000398010 | MDP0000866082 | MDP0000294359 | |

TABLE 6-continued

Accession numbers (Velasco et al., 2010; Retrieved from the Internet: Rosaceae.org) of biomarker genes for firm flesh browning risk assessment during cold storage. Higher or lower expression levels can result from cold stress resulting from storage imposition.

| | | | | | | | |
|---|---|---|---|---|---|---|---|
| MDP0000170286 | MDP0000530457 | MDP0000160547 | MDP0000248575 | MDP0000398765 | MDP0000869097 | MDP0000294423 | |
| MDP0000171430 | MDP0000532986 | MDP0000160880 | MDP0000248636 | MDP0000407273 | MDP0000870778 | MDP0000295375 | |
| MDP0000171707 | MDP0000533178 | MDP0000161125 | MDP0000248822 | MDP0000407755 | MDP0000872787 | MDP0000295392 | |
| MDP0000171771 | MDP0000533638 | MDP0000161160 | MDP0000248928 | MDP0000408705 | MDP0000872868 | MDP0000296241 | |
| MDP0000172092 | MDP0000534716 | MDP0000161311 | MDP0000249098 | MDP0000412025 | MDP0000873045 | MDP0000296859 | |
| MDP0000172922 | MDP0000534726 | MDP0000161677 | MDP0000249400 | MDP0000412490 | MDP0000873874 | MDP0000297735 | |
| MDP0000173050 | MDP0000536534 | MDP0000161920 | MDP0000249980 | MDP0000413774 | MDP0000874800 | MDP0000297861 | |
| MDP0000173174 | MDP0000544455 | MDP0000162025 | MDP0000250070 | MDP0000414607 | MDP0000876280 | MDP0000299256 | |
| MDP0000173424 | MDP0000545122 | MDP0000162146 | MDP0000250110 | MDP0000414786 | MDP0000877539 | MDP0000299702 | |
| MDP0000174676 | MDP0000548790 | MDP0000162220 | MDP0000250234 | MDP0000415407 | MDP0000878181 | MDP0000300452 | |
| MDP0000175504 | MDP0000549780 | MDP0000162233 | MDP0000250487 | MDP0000416021 | MDP0000878790 | MDP0000301169 | |
| MDP0000175691 | MDP0000552895 | MDP0000162375 | MDP0000250728 | MDP0000418187 | MDP0000881409 | MDP0000301472 | |
| MDP0000176097 | MDP0000555906 | MDP0000162579 | MDP0000250917 | MDP0000418900 | MDP0000883465 | MDP0000301576 | |
| MDP0000176753 | MDP0000560112 | MDP0000162721 | MDP0000250967 | MDP0000420320 | MDP0000884053 | MDP0000302366 | |
| MDP0000177099 | MDP0000561026 | MDP0000162872 | MDP0000251098 | MDP0000422023 | MDP0000884702 | MDP0000302731 | |
| MDP0000177378 | MDP0000568045 | MDP0000163222 | MDP0000251180 | MDP0000422537 | MDP0000885511 | MDP0000302970 | |
| MDP0000177906 | MDP0000573751 | MDP0000163330 | MDP0000251295 | MDP0000422862 | MDP0000886138 | MDP0000305045 | |
| MDP0000178684 | MDP0000575967 | MDP0000163451 | MDP0000251310 | MDP0000423544 | MDP0000887009 | MDP0000305440 | |
| MDP0000179769 | MDP0000576922 | MDP0000163575 | MDP0000251438 | MDP0000427251 | MDP0000891538 | MDP0000305563 | |
| MDP0000180472 | MDP0000577829 | MDP0000163924 | MDP0000251505 | MDP0000428573 | MDP0000894895 | MDP0000305848 | |
| MDP0000182098 | MDP0000581014 | MDP0000163943 | MDP0000251787 | MDP0000429824 | MDP0000895341 | MDP0000306121 | |
| MDP0000182342 | MDP0000585239 | MDP0000164054 | MDP0000251966 | MDP0000431417 | MDP0000896140 | MDP0000307308 | |
| MDP0000184324 | MDP0000585462 | MDP0000164095 | MDP0000252022 | MDP0000431696 | MDP0000896307 | MDP0000307703 | |
| MDP0000184518 | MDP0000588230 | MDP0000164159 | MDP0000252113 | MDP0000432471 | MDP0000896932 | MDP0000308999 | |
| MDP0000185022 | MDP0000590116 | MDP0000164201 | MDP0000252171 | MDP0000432497 | MDP0000897855 | MDP0000309014 | |
| MDP0000185640 | MDP0000601325 | MDP0000164243 | MDP0000252209 | MDP0000432499 | MDP0000897962 | MDP0000309351 | |
| MDP0000186011 | MDP0000601420 | MDP0000164610 | MDP0000252217 | MDP0000437033 | MDP0000902960 | MDP0000309383 | |
| MDP0000186135 | MDP0000607654 | MDP0000164847 | MDP0000252658 | MDP0000438046 | MDP0000905593 | MDP0000309484 | |
| MDP0000186167 | MDP0000608081 | MDP0000164977 | MDP0000252726 | MDP0000438931 | MDP0000905600 | MDP0000311067 | |
| MDP0000186560 | MDP0000609114 | MDP0000165060 | MDP0000252887 | MDP0000440622 | MDP0000908727 | MDP0000311618 | |
| MDP0000186762 | MDP0000609876 | MDP0000165187 | MDP0000253112 | MDP0000445041 | MDP0000909590 | MDP0000311808 | |
| MDP0000187155 | MDP0000610961 | MDP0000165209 | MDP0000253721 | MDP0000448168 | MDP0000909991 | MDP0000312364 | |
| MDP0000188716 | MDP0000611200 | MDP0000165715 | MDP0000254260 | MDP0000448457 | MDP0000912146 | MDP0000312567 | |
| MDP0000189095 | MDP0000619261 | MDP0000165830 | MDP0000254307 | MDP0000448667 | MDP0000912495 | MDP0000312569 | |
| MDP0000189388 | MDP0000624125 | MDP0000165846 | MDP0000254392 | MDP0000450994 | MDP0000915041 | MDP0000312866 | |
| MDP0000190809 | MDP0000629767 | MDP0000166139 | MDP0000254790 | MDP0000452572 | MDP0000915931 | MDP0000312983 | |
| MDP0000192511 | MDP0000632679 | MDP0000166168 | MDP0000254933 | MDP0000453188 | MDP0000916469 | MDP0000313394 | |
| MDP0000192765 | MDP0000635152 | MDP0000166644 | MDP0000255005 | MDP0000453190 | MDP0000916486 | MDP0000314081 | |
| MDP0000193399 | MDP0000636042 | MDP0000166657 | MDP0000255284 | MDP0000453207 | MDP0000917005 | MDP0000314219 | |
| MDP0000193724 | MDP0000636632 | MDP0000166743 | MDP0000255392 | MDP0000453695 | MDP0000917824 | MDP0000314364 | |
| MDP0000194799 | MDP0000638487 | MDP0000166935 | MDP0000256017 | MDP0000453800 | MDP0000920394 | MDP0000314632 | |
| MDP0000195573 | MDP0000646858 | MDP0000166969 | MDP0000256328 | MDP0000455180 | MDP0000920400 | MDP0000314694 | |
| MDP0000195614 | MDP0000652545 | MDP0000167107 | MDP0000256347 | MDP0000455634 | MDP0000922723 | MDP0000314942 | |
| MDP0000195916 | MDP0000656720 | MDP0000167358 | MDP0000256573 | MDP0000455844 | MDP0000923711 | MDP0000317819 | |
| MDP0000196008 | MDP0000658332 | MDP0000168416 | MDP0000256650 | MDP0000456401 | MDP0000926304 | MDP0000318625 | |
| MDP0000196174 | MDP0000663723 | MDP0000168437 | MDP0000256805 | MDP0000458062 | MDP0000927642 | MDP0000319966 | |
| MDP0000198108 | MDP0000664773 | MDP0000168790 | MDP0000257119 | MDP0000458498 | MDP0000932913 | MDP0000320056 | |
| MDP0000198757 | MDP0000665685 | MDP0000168972 | MDP0000257884 | MDP0000459010 | MDP0000933747 | MDP0000320119 | |
| MDP0000199110 | MDP0000673112 | MDP0000169032 | MDP0000258118 | MDP0000460020 | MDP0000936748 | MDP0000320161 | |
| MDP0000199149 | MDP0000681724 | MDP0000169101 | MDP0000258192 | MDP0000461780 | MDP0000937986 | MDP0000320707 | |
| MDP0000199152 | MDP0000682327 | MDP0000169201 | MDP0000259063 | MDP0000463117 | MDP0000939841 | MDP0000320910 | |
| MDP0000199273 | MDP0000683341 | MDP0000169202 | MDP0000259547 | MDP0000464599 | MDP0000940086 | MDP0000321380 | |
| MDP0000200306 | MDP0000686185 | MDP0000169311 | MDP0000259591 | MDP0000465955 | MDP0000940411 | MDP0000322107 | |
| MDP0000200646 | MDP0000686885 | MDP0000169615 | MDP0000259706 | MDP0000465844 | MDP0000940828 | MDP0000322401 | |
| MDP0000200799 | MDP0000689946 | MDP0000169857 | MDP0000259770 | MDP0000466557 | MDP0000942125 | MDP0000322606 | |
| MDP0000201745 | MDP0000697030 | MDP0000169984 | MDP0000259862 | MDP0000470441 | MDP0000943292 | MDP0000322755 | |
| MDP0000202716 | MDP0000697237 | MDP0000170360 | MDP0000260407 | MDP0000474576 | MDP0000943304 | MDP0000324718 | |
| MDP0000203090 | MDP0000699845 | MDP0000170414 | MDP0000261375 | MDP0000476035 | MDP0000944724 | MDP0000325786 | |
| MDP0000203109 | MDP0000704996 | MDP0000170739 | MDP0000261492 | MDP0000476444 | MDP0000949385 | MDP0000326735 | |
| MDP0000203591 | MDP0000708135 | MDP0000171402 | MDP0000261679 | MDP0000476508 | MDP0000951203 | MDP0000327829 | |
| MDP0000203716 | MDP0000710437 | MDP0000171638 | MDP0000261719 | MDP0000477966 | MDP0000951395 | MDP0000332896 | |
| MDP0000204569 | MDP0000715270 | MDP0000171834 | MDP0000262301 | MDP0000478758 | MDP0000033458 | MDP0000336518 | |
| MDP0000205602 | MDP0000718381 | MDP0000171877 | MDP0000262687 | MDP0000479094 | MDP0000043189 | MDP0000341605 | |
| MDP0000205674 | MDP0000719836 | MDP0000172233 | MDP0000262762 | MDP0000479478 | MDP0000053005 | MDP0000344085 | |
| MDP0000205760 | MDP0000720785 | MDP0000172320 | MDP0000263529 | MDP0000481097 | MDP0000058337 | MDP0000344130 | |
| MDP0000205823 | MDP0000725469 | MDP0000172464 | MDP0000263585 | MDP0000481989 | MDP0000062263 | MDP0000347586 | |
| MDP0000206216 | MDP0000725984 | MDP0000172842 | MDP0000263628 | MDP0000486046 | MDP0000113336 | MDP0000348010 | |
| MDP0000206715 | MDP0000729348 | MDP0000173036 | MDP0000263959 | MDP0000486743 | MDP0000119071 | MDP0000349942 | |
| MDP0000207774 | MDP0000730751 | MDP0000173145 | MDP0000264232 | MDP0000489011 | MDP0000119284 | MDP0000356821 | |
| MDP0000208332 | MDP0000733506 | MDP0000173476 | MDP0000264441 | MDP0000489357 | MDP0000121379 | MDP0000356904 | |
| MDP0000209081 | MDP0000734649 | MDP0000173510 | MDP0000264592 | MDP0000490749 | MDP0000121411 | MDP0000360394 | |
| MDP0000209189 | MDP0000735118 | MDP0000173549 | MDP0000264804 | MDP0000490800 | MDP0000121412 | MDP0000360808 | |
| MDP0000209313 | MDP0000737001 | MDP0000173611 | MDP0000265219 | MDP0000492898 | MDP0000121822 | MDP0000360930 | |
| MDP0000209438 | MDP0000738777 | MDP0000173732 | MDP0000265806 | MDP0000494411 | MDP0000122978 | MDP0000362862 | |
| MDP0000211206 | MDP0000739591 | MDP0000174018 | MDP0000265913 | MDP0000495733 | MDP0000123747 | MDP0000364615 | |

TABLE 6-continued

Accession numbers (Velasco et al., 2010; Retrieved from the Internet: Rosaceae.org) of biomarker genes for firm flesh browning risk assessment during cold storage. Higher or lower expression levels can result from cold stress resulting from storage imposition.

| | | | | | | |
|---|---|---|---|---|---|---|
| MDP0000211459 | MDP0000742278 | MDP0000174168 | MDP0000266003 | MDP0000495793 | MDP0000123893 | MDP0000366291 |
| MDP0000211540 | MDP0000745680 | MDP0000174196 | MDP0000266406 | MDP0000496087 | MDP0000123894 | MDP0000368496 |
| MDP0000211875 | MDP0000745895 | MDP0000174599 | MDP0000266638 | MDP0000500159 | MDP0000123987 | MDP0000376256 |
| MDP0000211915 | MDP0000750556 | MDP0000174615 | MDP0000266665 | MDP0000500661 | MDP0000124002 | MDP0000381531 |
| MDP0000212363 | MDP0000751780 | MDP0000174749 | MDP0000267115 | MDP0000500806 | MDP0000124063 | MDP0000382336 |
| MDP0000213057 | MDP0000753318 | MDP0000174791 | MDP0000267218 | MDP0000501957 | MDP0000124296 | MDP0000386460 |
| MDP0000213088 | MDP0000753366 | MDP0000174801 | MDP0000267538 | MDP0000503341 | MDP0000125193 | MDP0000389186 |
| MDP0000213770 | MDP0000754160 | MDP0000175026 | MDP0000267609 | MDP0000504527 | MDP0000125504 | MDP0000391241 |
| MDP0000214409 | MDP0000758881 | MDP0000175067 | MDP0000267674 | MDP0000506825 | MDP0000126204 | MDP0000393950 |
| MDP0000214697 | MDP0000759591 | MDP0000175282 | MDP0000268081 | MDP0000507001 | MDP0000128045 | MDP0000396119 |
| MDP0000214843 | MDP0000760376 | MDP0000175501 | MDP0000268229 | MDP0000508761 | MDP0000128562 | MDP0000397221 |
| MDP0000216173 | MDP0000763557 | MDP0000177037 | MDP0000268304 | MDP0000509613 | MDP0000128733 | MDP0000400084 |
| MDP0000217005 | MDP0000763960 | MDP0000177377 | MDP0000269284 | MDP0000510248 | MDP0000129412 | MDP0000406864 |
| MDP0000217690 | MDP0000766213 | MDP0000178196 | MDP0000269711 | MDP0000510770 | MDP0000129717 | MDP0000410447 |
| MDP0000218099 | MDP0000769652 | MDP0000178268 | MDP0000270117 | MDP0000511083 | MDP0000130173 | MDP0000412939 |
| MDP0000218691 | MDP0000770103 | MDP0000178483 | MDP0000271058 | MDP0000511650 | MDP0000131105 | MDP0000423449 |
| MDP0000218759 | MDP0000771573 | MDP0000178508 | MDP0000271894 | MDP0000512062 | MDP0000131161 | MDP0000425030 |
| MDP0000219021 | MDP0000772017 | MDP0000178561 | MDP0000272351 | MDP0000515080 | MDP0000131207 | MDP0000426070 |
| MDP0000219062 | MDP0000774924 | MDP0000178612 | MDP0000273157 | MDP0000515141 | MDP0000131371 | MDP0000426372 |
| MDP0000219463 | MDP0000780353 | MDP0000178670 | MDP0000273201 | MDP0000515144 | MDP0000131486 | MDP0000435717 |
| MDP0000219737 | MDP0000782882 | MDP0000178782 | MDP0000273759 | MDP0000521965 | MDP0000131814 | MDP0000437886 |
| MDP0000221660 | MDP0000784168 | MDP0000179051 | MDP0000273828 | MDP0000526206 | MDP0000131990 | MDP0000437997 |
| MDP0000221844 | MDP0000784309 | MDP0000179178 | MDP0000273870 | MDP0000527950 | MDP0000132162 | MDP0000439439 |
| MDP0000222300 | MDP0000784608 | MDP0000179744 | MDP0000274017 | MDP0000528658 | MDP0000132235 | MDP0000442260 |
| MDP0000222391 | MDP0000784851 | MDP0000179808 | MDP0000274746 | MDP0000530792 | MDP0000132477 | MDP0000451244 |
| MDP0000222593 | MDP0000787281 | MDP0000180245 | MDP0000274905 | MDP0000530871 | MDP0000132549 | MDP0000456521 |
| MDP0000223726 | MDP0000790904 | MDP0000180387 | MDP0000275509 | MDP0000538536 | MDP0000132608 | MDP0000461203 |
| MDP0000224857 | MDP0000794936 | MDP0000180494 | MDP0000275800 | MDP0000539101 | MDP0000132990 | MDP0000466497 |
| MDP0000225088 | MDP0000804078 | MDP0000180684 | MDP0000275915 | MDP0000540782 | MDP0000133918 | MDP0000474746 |
| MDP0000225651 | MDP0000804427 | MDP0000181160 | MDP0000276057 | MDP0000545379 | MDP0000134135 | MDP0000475839 |
| MDP0000226135 | MDP0000804707 | MDP0000181436 | MDP0000276730 | MDP0000547021 | MDP0000135858 | MDP0000477923 |
| MDP0000226848 | MDP0000805606 | MDP0000181572 | MDP0000276807 | MDP0000547788 | MDP0000135898 | MDP0000478473 |
| MDP0000228176 | MDP0000807958 | MDP0000182154 | MDP0000276816 | MDP0000548943 | MDP0000136104 | MDP0000481866 |
| MDP0000228470 | MDP0000809773 | MDP0000182437 | MDP0000277067 | MDP0000549234 | MDP0000137185 | MDP0000487911 |
| MDP0000229140 | MDP0000813339 | MDP0000182546 | MDP0000277127 | MDP0000550529 | MDP0000137441 | MDP0000488621 |
| MDP0000229285 | MDP0000813554 | MDP0000183140 | MDP0000277173 | MDP0000551974 | MDP0000137802 | MDP0000491658 |
| MDP0000229364 | MDP0000813710 | MDP0000183540 | MDP0000277370 | MDP0000552558 | MDP0000138123 | MDP0000492744 |
| MDP0000229468 | MDP0000814399 | MDP0000183660 | MDP0000277557 | MDP0000552625 | MDP0000138851 | MDP0000495763 |
| MDP0000229768 | MDP0000814899 | MDP0000183751 | MDP0000278149 | MDP0000552871 | MDP0000139605 | MDP0000496027 |
| MDP0000230611 | MDP0000815242 | MDP0000183814 | MDP0000278157 | MDP0000553959 | MDP0000139977 | MDP0000499668 |
| MDP0000230800 | MDP0000817852 | MDP0000183910 | MDP0000278259 | MDP0000555220 | MDP0000140386 | MDP0000503880 |
| MDP0000231619 | MDP0000818944 | MDP0000183959 | MDP0000278523 | MDP0000555329 | MDP0000140655 | MDP0000508911 |
| MDP0000231680 | MDP0000821951 | MDP0000184195 | MDP0000278580 | MDP0000560731 | MDP0000142512 | MDP0000509438 |
| MDP0000231748 | MDP0000823528 | MDP0000184300 | MDP0000279018 | MDP0000561022 | MDP0000142765 | MDP0000511847 |
| MDP0000231960 | MDP0000827820 | MDP0000184530 | MDP0000279028 | MDP0000561838 | MDP0000144968 | MDP0000513751 |
| MDP0000233141 | MDP0000828513 | MDP0000184562 | MDP0000279220 | MDP0000561941 | MDP0000145765 | MDP0000518482 |
| MDP0000233177 | MDP0000830772 | MDP0000184892 | MDP0000279292 | MDP0000562587 | MDP0000148221 | MDP0000529756 |
| MDP0000233401 | MDP0000830795 | MDP0000185145 | MDP0000279326 | MDP0000563899 | MDP0000149604 | MDP0000533607 |
| MDP0000233658 | MDP0000831518 | MDP0000185368 | MDP0000279973 | MDP0000563920 | MDP0000150165 | MDP0000534197 |
| MDP0000233761 | MDP0000831519 | MDP0000186964 | MDP0000280093 | MDP0000566057 | MDP0000150973 | MDP0000535127 |
| MDP0000234499 | MDP0000833352 | MDP0000187103 | MDP0000280319 | MDP0000566223 | MDP0000151095 | MDP0000535568 |
| MDP0000234690 | MDP0000834641 | MDP0000187256 | MDP0000280500 | MDP0000566567 | MDP0000151293 | MDP0000539269 |
| MDP0000236614 | MDP0000835211 | MDP0000187493 | MDP0000280820 | MDP0000566690 | MDP0000151537 | MDP0000539956 |
| MDP0000237125 | MDP0000835932 | MDP0000187706 | MDP0000281162 | MDP0000567268 | MDP0000153229 | MDP0000547461 |
| MDP0000237989 | MDP0000836165 | MDP0000188077 | MDP0000281334 | MDP0000568825 | MDP0000153524 | MDP0000547986 |
| MDP0000239643 | MDP0000838523 | MDP0000188613 | MDP0000281525 | MDP0000568913 | MDP0000154068 | MDP0000550659 |
| MDP0000239958 | MDP0000840722 | MDP0000188976 | MDP0000281627 | MDP0000569069 | MDP0000155446 | MDP0000553484 |
| MDP0000241736 | MDP0000841918 | MDP0000190006 | MDP0000282583 | MDP0000569128 | MDP0000155575 | MDP0000557169 |
| MDP0000242413 | MDP0000842877 | MDP0000190489 | MDP0000282711 | MDP0000570186 | MDP0000155799 | MDP0000560623 |
| MDP0000242552 | MDP0000847090 | MDP0000190504 | MDP0000282814 | MDP0000573540 | MDP0000158766 | MDP0000566625 |
| MDP0000243237 | MDP0000857446 | MDP0000191304 | MDP0000283036 | MDP0000574105 | MDP0000159246 | MDP0000569149 |
| MDP0000244251 | MDP0000862169 | MDP0000191389 | MDP0000283166 | MDP0000574158 | MDP0000160249 | MDP0000570102 |
| MDP0000244749 | MDP0000864747 | MDP0000191455 | MDP0000283288 | MDP0000574554 | MDP0000160434 | MDP0000574987 |
| MDP0000247270 | MDP0000865961 | MDP0000191557 | MDP0000283772 | MDP0000574556 | MDP0000161869 | MDP0000578396 |
| MDP0000247348 | MDP0000866270 | MDP0000191620 | MDP0000283898 | MDP0000574982 | MDP0000162279 | MDP0000596439 |
| MDP0000247912 | MDP0000873667 | MDP0000191837 | MDP0000283944 | MDP0000576205 | MDP0000162923 | MDP0000597773 |
| MDP0000247926 | MDP0000875654 | MDP0000191848 | MDP0000284245 | MDP0000576682 | MDP0000163089 | MDP0000598367 |
| MDP0000248628 | MDP0000877937 | MDP0000191926 | MDP0000284554 | MDP0000577872 | MDP0000163684 | MDP0000599042 |
| MDP0000249384 | MDP0000878773 | MDP0000191939 | MDP0000284842 | MDP0000578211 | MDP0000163930 | MDP0000605874 |
| MDP0000249405 | MDP0000885639 | MDP0000192132 | MDP0000285521 | MDP0000581549 | MDP0000163931 | MDP0000606453 |
| MDP0000250895 | MDP0000889159 | MDP0000192468 | MDP0000285682 | MDP0000583574 | MDP0000164922 | MDP0000612469 |
| MDP0000250936 | MDP0000889223 | MDP0000192470 | MDP0000285894 | MDP0000585315 | MDP0000165381 | MDP0000615948 |
| MDP0000251256 | MDP0000899351 | MDP0000192562 | MDP0000286646 | MDP0000586656 | MDP0000167288 | MDP0000616079 |
| MDP0000251531 | MDP0000900067 | MDP0000192940 | MDP0000286908 | MDP0000587459 | MDP0000168293 | MDP0000616163 |
| MDP0000251570 | MDP0000900422 | MDP0000193050 | MDP0000287029 | MDP0000590966 | MDP0000168543 | MDP0000617956 |

TABLE 6-continued

Accession numbers (Velasco et al., 2010; Retrieved from the Internet: Rosaceae.org) of biomarker genes for firm flesh browning risk assessment during cold storage. Higher or lower expression levels can result from cold stress resulting from storage imposition.

| | | | | | | | |
|---|---|---|---|---|---|---|---|
| MDP0000252508 | MDP0000901967 | MDP0000193127 | MDP0000287199 | MDP0000590974 | MDP0000168826 | MDP0000620250 | |
| MDP0000252824 | MDP0000902360 | MDP0000193196 | MDP0000287751 | MDP0000591068 | MDP0000169287 | MDP0000622590 | |
| MDP0000252969 | MDP0000902760 | MDP0000193220 | MDP0000287830 | MDP0000591411 | MDP0000169344 | MDP0000630247 | |
| MDP0000253075 | MDP0000903805 | MDP0000193347 | MDP0000287919 | MDP0000592961 | MDP0000170216 | MDP0000642505 | |
| MDP0000253105 | MDP0000904379 | MDP0000193401 | MDP0000288107 | MDP0000593517 | MDP0000170687 | MDP0000648621 | |
| MDP0000253428 | MDP0000904458 | MDP0000193479 | MDP0000288163 | MDP0000593536 | MDP0000171200 | MDP0000651353 | |
| MDP0000253802 | MDP0000906147 | MDP0000194305 | MDP0000288439 | MDP0000599531 | MDP0000171708 | MDP0000652130 | |
| MDP0000253952 | MDP0000908305 | MDP0000194663 | MDP0000288573 | MDP0000604396 | MDP0000172849 | MDP0000656663 | |
| MDP0000255411 | MDP0000911067 | MDP0000195003 | MDP0000288682 | MDP0000604702 | MDP0000173365 | MDP0000658830 | |
| MDP0000255770 | MDP0000913661 | MDP0000195254 | MDP0000289195 | MDP0000606526 | MDP0000173780 | MDP0000659260 | |
| MDP0000256965 | MDP0000917143 | MDP0000195385 | MDP0000289836 | MDP0000607777 | MDP0000175141 | MDP0000661922 | |
| MDP0000258610 | MDP0000920189 | MDP0000195787 | MDP0000289917 | MDP0000608645 | MDP0000175481 | MDP0000662596 | |
| MDP0000259536 | MDP0000921319 | MDP0000195993 | MDP0000290295 | MDP0000608923 | MDP0000176383 | MDP0000672088 | |
| MDP0000259550 | MDP0000923308 | MDP0000196026 | MDP0000290562 | MDP0000610136 | MDP0000178206 | MDP0000679622 | |
| MDP0000259837 | MDP0000925648 | MDP0000196588 | MDP0000291146 | MDP0000610753 | MDP0000179216 | MDP0000679923 | |
| MDP0000259955 | MDP0000927351 | MDP0000196639 | MDP0000291345 | MDP0000610922 | MDP0000179654 | MDP0000681768 | |
| MDP0000260110 | MDP0000928608 | MDP0000196665 | MDP0000291544 | MDP0000611628 | MDP0000179847 | MDP0000685403 | |
| MDP0000260408 | MDP0000929213 | MDP0000196894 | MDP0000292131 | MDP0000612208 | MDP0000179967 | MDP0000687619 | |
| MDP0000262678 | MDP0000930401 | MDP0000197119 | MDP0000292294 | MDP0000612660 | MDP0000180763 | MDP0000703468 | |
| MDP0000262789 | MDP0000931048 | MDP0000197224 | MDP0000292846 | MDP0000614645 | MDP0000180915 | MDP0000706020 | |
| MDP0000263222 | MDP0000931940 | MDP0000197242 | MDP0000292881 | MDP0000619638 | MDP0000181148 | MDP0000709729 | |
| MDP0000263664 | MDP0000932804 | MDP0000197292 | MDP0000292908 | MDP0000620797 | MDP0000181521 | MDP0000709799 | |
| MDP0000264060 | MDP0000938611 | MDP0000197297 | MDP0000293001 | MDP0000623588 | MDP0000182455 | MDP0000710146 | |
| MDP0000264666 | MDP0000939633 | MDP0000197509 | MDP0000293002 | MDP0000623979 | MDP0000184668 | MDP0000710467 | |
| MDP0000265046 | MDP0000940313 | MDP0000198191 | MDP0000293126 | MDP0000623980 | MDP0000184929 | MDP0000715898 | |
| MDP0000265644 | MDP0000941000 | MDP0000198466 | MDP0000293165 | MDP0000624279 | MDP0000185293 | MDP0000720799 | |
| MDP0000266144 | MDP0000945788 | MDP0000198624 | MDP0000293264 | MDP0000628330 | MDP0000185616 | MDP0000728753 | |
| MDP0000266257 | MDP0000948298 | MDP0000198741 | MDP0000293468 | MDP0000629768 | MDP0000186069 | MDP0000728755 | |
| MDP0000266398 | MDP0000949494 | MDP0000198903 | MDP0000293661 | MDP0000630832 | MDP0000186368 | MDP0000733399 | |
| MDP0000266399 | MDP0000949986 | MDP0000198953 | MDP0000293854 | MDP0000631284 | MDP0000186912 | MDP0000735095 | |
| MDP0000267894 | MDP0000950554 | MDP0000198955 | MDP0000294163 | MDP0000637744 | MDP0000186963 | MDP0000739959 | |
| MDP0000267909 | MDP0000012541 | MDP0000200231 | MDP0000294360 | MDP0000638263 | MDP0000190423 | MDP0000740656 | |
| MDP0000268320 | MDP0000016671 | MDP0000200442 | MDP0000294531 | MDP0000638870 | MDP0000191423 | MDP0000744273 | |
| MDP0000268505 | MDP0000024364 | MDP0000200564 | MDP0000294634 | MDP0000639777 | MDP0000192362 | MDP0000747105 | |
| MDP0000270731 | MDP0000030527 | MDP0000201098 | MDP0000294776 | MDP0000639894 | MDP0000192492 | MDP0000749824 | |
| MDP0000271244 | MDP0000046978 | MDP0000201220 | MDP0000294847 | MDP0000641583 | MDP0000193109 | MDP0000751143 | |
| MDP0000271479 | MDP0000054634 | MDP0000201389 | MDP0000294867 | MDP0000642253 | MDP0000193128 | MDP0000752656 | |
| MDP0000271897 | MDP0000062066 | MDP0000201523 | MDP0000295258 | MDP0000642826 | MDP0000193734 | MDP0000759646 | |
| MDP0000272492 | MDP0000084546 | MDP0000202156 | MDP0000295542 | MDP0000643331 | MDP0000194134 | MDP0000761026 | |
| MDP0000272499 | MDP0000092033 | MDP0000202184 | MDP0000295748 | MDP0000644142 | MDP0000194319 | MDP0000762227 | |
| MDP0000273588 | MDP0000096208 | MDP0000202280 | MDP0000295812 | MDP0000644930 | MDP0000194597 | MDP0000771056 | |
| MDP0000274409 | MDP0000096923 | MDP0000202473 | MDP0000295826 | MDP0000644979 | MDP0000195878 | MDP0000773021 | |
| MDP0000276078 | MDP0000104111 | MDP0000202883 | MDP0000295938 | MDP0000645105 | MDP0000195885 | MDP0000773084 | |
| MDP0000276278 | MDP0000116244 | MDP0000203813 | MDP0000296025 | MDP0000647346 | MDP0000197456 | MDP0000773525 | |
| MDP0000276541 | MDP0000118766 | MDP0000203897 | MDP0000296280 | MDP0000648218 | MDP0000197558 | MDP0000776321 | |
| MDP0000277088 | MDP0000118943 | MDP0000203983 | MDP0000296317 | MDP0000649783 | MDP0000197775 | MDP0000778113 | |
| MDP0000277215 | MDP0000119148 | MDP0000204547 | MDP0000296695 | MDP0000650225 | MDP0000198420 | MDP0000781178 | |
| MDP0000277666 | MDP0000119414 | MDP0000204730 | MDP0000297071 | MDP0000650491 | MDP0000199076 | MDP0000783034 | |
| MDP0000278046 | MDP0000119737 | MDP0000204731 | MDP0000297138 | MDP0000651801 | MDP0000200319 | MDP0000783444 | |
| MDP0000279249 | MDP0000119860 | MDP0000205226 | MDP0000297460 | MDP0000652760 | MDP0000200355 | MDP0000783511 | |
| MDP0000279576 | MDP0000120125 | MDP0000206212 | MDP0000297614 | MDP0000654243 | MDP0000200419 | MDP0000784035 | |
| MDP0000279839 | MDP0000120761 | MDP0000206473 | MDP0000298230 | MDP0000655939 | MDP0000200569 | MDP0000785138 | |
| MDP0000280001 | MDP0000120819 | MDP0000206596 | MDP0000298659 | MDP0000656101 | MDP0000200737 | MDP0000786380 | |
| MDP0000280908 | MDP0000120921 | MDP0000206691 | MDP0000298903 | MDP0000656197 | MDP0000200896 | MDP0000787725 | |
| MDP0000281626 | MDP0000120959 | MDP0000206714 | MDP0000299064 | MDP0000657053 | MDP0000201429 | MDP0000791995 | |
| MDP0000281632 | MDP0000121380 | MDP0000206775 | MDP0000299114 | MDP0000657439 | MDP0000203275 | MDP0000795356 | |
| MDP0000283400 | MDP0000121493 | MDP0000206912 | MDP0000299310 | MDP0000657456 | MDP0000203822 | MDP0000795754 | |
| MDP0000286574 | MDP0000121522 | MDP0000206973 | MDP0000299311 | MDP0000657517 | MDP0000205654 | MDP0000800945 | |
| MDP0000287234 | MDP0000122066 | MDP0000207149 | MDP0000299402 | MDP0000657852 | MDP0000207919 | MDP0000801117 | |
| MDP0000287302 | MDP0000122127 | MDP0000207215 | MDP0000299872 | MDP0000658305 | MDP0000208326 | MDP0000803116 | |
| MDP0000287581 | MDP0000122458 | MDP0000207220 | MDP0000299915 | MDP0000659818 | MDP0000208497 | MDP0000803674 | |
| MDP0000287647 | MDP0000122792 | MDP0000207500 | MDP0000299980 | MDP0000659907 | MDP0000208804 | MDP0000807889 | |
| MDP0000287729 | MDP0000123287 | MDP0000207601 | MDP0000300045 | MDP0000662428 | MDP0000208907 | MDP0000810488 | |
| MDP0000288293 | MDP0000123432 | MDP0000207745 | MDP0000300046 | MDP0000662880 | MDP0000209660 | MDP0000810883 | |
| MDP0000288684 | MDP0000123467 | MDP0000208088 | MDP0000300161 | MDP0000663105 | MDP0000210336 | MDP0000811127 | |
| MDP0000289412 | MDP0000123659 | MDP0000208090 | MDP0000300351 | MDP0000666539 | MDP0000210641 | MDP0000811918 | |
| MDP0000290182 | MDP0000123680 | MDP0000208137 | MDP0000301119 | MDP0000666771 | MDP0000210846 | MDP0000813278 | |
| MDP0000290620 | MDP0000124013 | MDP0000208204 | MDP0000301515 | MDP0000670935 | MDP0000211494 | MDP0000813922 | |
| MDP0000290970 | MDP0000124053 | MDP0000208899 | MDP0000301677 | MDP0000670959 | MDP0000211660 | MDP0000814874 | |
| MDP0000292132 | MDP0000124233 | MDP0000201994 | MDP0000301994 | MDP0000672731 | MDP0000211661 | MDP0000815097 | |
| MDP0000292492 | MDP0000124375 | MDP0000209368 | MDP0000302021 | MDP0000673070 | MDP0000211968 | MDP0000819881 | |
| MDP0000293045 | MDP0000124832 | MDP0000209464 | MDP0000302198 | MDP0000674589 | MDP0000212002 | MDP0000824147 | |
| MDP0000293103 | MDP0000124866 | MDP0000209633 | MDP0000302538 | MDP0000674666 | MDP0000212007 | MDP0000834656 | |
| MDP0000293143 | MDP0000124881 | MDP0000209662 | MDP0000302716 | MDP0000674719 | MDP0000214625 | MDP0000835140 | |
| MDP0000293236 | MDP0000125082 | MDP0000209689 | MDP0000302838 | MDP0000675548 | MDP0000216225 | MDP0000841708 | |

TABLE 6-continued

Accession numbers (Velasco et al., 2010; Retrieved from the Internet: Rosaceae.org) of biomarker genes for firm flesh browning risk assessment during cold storage. Higher or lower expression levels can result from cold stress resulting from storage imposition.

| | | | | | | |
|---|---|---|---|---|---|---|
| MDP0000293842 | MDP0000125709 | MDP0000209713 | MDP0000302905 | MDP0000676693 | MDP0000216376 | MDP0000848515 |
| MDP0000293974 | MDP0000126455 | MDP0000209897 | MDP0000303101 | MDP0000679280 | MDP0000216945 | MDP0000853531 |
| MDP0000294379 | MDP0000126718 | MDP0000210022 | MDP0000303198 | MDP0000680042 | MDP0000217142 | MDP0000858452 |
| MDP0000295039 | MDP0000126850 | MDP0000210238 | MDP0000303384 | MDP0000681106 | MDP0000217310 | MDP0000859733 |
| MDP0000295223 | MDP0000127834 | MDP0000210254 | MDP0000303430 | MDP0000682471 | MDP0000217362 | MDP0000863049 |
| MDP0000295540 | MDP0000127930 | MDP0000210260 | MDP0000303496 | MDP0000684216 | MDP0000217499 | MDP0000863404 |
| MDP0000295543 | MDP0000128265 | MDP0000211252 | MDP0000303872 | MDP0000685420 | MDP0000217803 | MDP0000864442 |
| MDP0000295562 | MDP0000128267 | MDP0000211643 | MDP0000304254 | MDP0000685425 | MDP0000217850 | MDP0000866840 |
| MDP0000295794 | MDP0000128423 | MDP0000211758 | MDP0000304881 | MDP0000685724 | MDP0000218078 | MDP0000868044 |
| MDP0000298232 | MDP0000128463 | MDP0000211874 | MDP0000305029 | MDP0000686466 | MDP0000219430 | MDP0000868659 |
| MDP0000298527 | MDP0000128531 | MDP0000211955 | MDP0000305338 | MDP0000688188 | MDP0000219802 | MDP0000873893 |
| MDP0000299181 | MDP0000128560 | MDP0000212045 | MDP0000305695 | MDP0000688643 | MDP0000219838 | MDP0000874667 |
| MDP0000300808 | MDP0000128786 | MDP0000212077 | MDP0000305886 | MDP0000689162 | MDP0000220167 | MDP0000883367 |
| MDP0000301666 | MDP0000128790 | MDP0000212327 | MDP0000305934 | MDP0000689889 | MDP0000220328 | MDP0000891353 |
| MDP0000302024 | MDP0000128937 | MDP0000212372 | MDP0000306224 | MDP0000691413 | MDP0000221160 | MDP0000892526 |
| MDP0000302440 | MDP0000129051 | MDP0000212760 | MDP0000306907 | MDP0000692523 | MDP0000222089 | MDP0000895380 |
| MDP0000302671 | MDP0000129445 | MDP0000212975 | MDP0000306990 | MDP0000694318 | MDP0000222724 | MDP0000899413 |
| MDP0000303449 | MDP0000129648 | MDP0000213508 | MDP0000307150 | MDP0000694562 | MDP0000223057 | MDP0000901379 |
| MDP0000304620 | MDP0000129681 | MDP0000213863 | MDP0000307340 | MDP0000696497 | MDP0000223568 | MDP0000903481 |
| MDP0000304719 | MDP0000130630 | MDP0000213948 | MDP0000307432 | MDP0000696624 | MDP0000223905 | MDP0000905321 |
| MDP0000305094 | MDP0000130716 | MDP0000214579 | MDP0000307685 | MDP0000697378 | MDP0000224209 | MDP0000905924 |
| MDP0000306738 | MDP0000130769 | MDP0000214797 | MDP0000307853 | MDP0000697676 | MDP0000224389 | MDP0000906703 |
| MDP0000306888 | MDP0000131142 | MDP0000215239 | MDP0000308181 | MDP0000698024 | MDP0000224417 | MDP0000910032 |
| MDP0000307717 | MDP0000131267 | MDP0000215270 | MDP0000308285 | MDP0000698038 | MDP0000224930 | MDP0000911731 |
| MDP0000308205 | MDP0000131368 | MDP0000215276 | MDP0000308395 | MDP0000700189 | MDP0000225340 | MDP0000921067 |
| MDP0000309160 | MDP0000131377 | MDP0000215777 | MDP0000308491 | MDP0000702868 | MDP0000226276 | MDP0000921871 |
| MDP0000309314 | MDP0000131386 | MDP0000216638 | MDP0000308907 | MDP0000703059 | MDP0000227692 | MDP0000928898 |
| MDP0000309732 | MDP0000131731 | MDP0000216907 | MDP0000308938 | MDP0000705359 | MDP0000227742 | MDP0000937996 |
| MDP0000309741 | MDP0000132207 | MDP0000216952 | MDP0000309169 | MDP0000706828 | MDP0000228529 | MDP0000942516 |
| MDP0000310093 | MDP0000132209 | MDP0000217406 | MDP0000309382 | MDP0000708299 | MDP0000228670 | MDP0000942873 |
| MDP0000310940 | MDP0000132381 | MDP0000217451 | MDP0000309530 | MDP0000708692 | MDP0000229338 | MDP0000944409 |
| MDP0000311556 | MDP0000132436 | MDP0000217745 | MDP0000309676 | MDP0000709073 | MDP0000231369 | MDP0000947607 |
| MDP0000312449 | MDP0000132623 | MDP0000218252 | MDP0000309805 | MDP0000709523 | MDP0000231477 | MDP0000949486 |
| MDP0000312701 | MDP0000132726 | MDP0000218451 | MDP0000310374 | MDP0000711379 | MDP0000232264 | MDP0000950422 |
| MDP0000312765 | MDP0000132855 | MDP0000218748 | MDP0000310430 | MDP0000711832 | MDP0000232789 | |
| MDP0000312878 | MDP0000132952 | MDP0000218810 | MDP0000310641 | MDP0000711891 | MDP0000233356 | |

The methods of the present invention may be practiced using any set of genes selected from the candidate genes disclosed herein, as long as the expression profiles of the genes within a given set discriminate between browning disorder progression outcomes.

The identification of such sets of genes may be performed by any suitable selection method, including, but not limited to, cluster analysis, supported vector machines, neural networks or other algorithms. A set of genes identified by such selection methods is generally capable of predicting the classification of an unknown sample based on the expression levels of genes used for the discrimination. "Leave one out" cross-validation may be used to test the performance of various models and to help identify weights (genes) that are uninformative (e.g., redundant) or detrimental to the predictive ability of the gene model.

As will be appreciated by those of ordinary skill in the art, sets of genes whose expression profiles correlate with browning disorder progression, and which can discriminate between browning disorder progression outcomes, may be used to identify/study unknown Rosaceous tissue samples. Accordingly, the present invention provides methods for characterizing Rosaceous tissue in Rosaceous fruit crops suspected of having the risk of developing multiple browning disorders.

The diagnostic/prognostic methods of the present invention generally involve the determination of expression levels of a set of genes in a Rosaceous tissue sample. Determination of gene expression levels in the practice of the inventive methods may be performed by any suitable method. For example, determination of gene expression levels may be performed by detecting the expression of mRNA expressed from the genes of interest and/or by detecting the expression of a polypeptide encoded by the genes. Here, we have exemplified the determination of gene expression by the RNAseq method.

Our method can be readily adapted to currently available, existing platforms for measuring biomarkers. The expected end users of our products include apple producers, storage operators, shippers, retailers, agricultural laboratories, and agrichemical service providers. The same or similar equipment is already regularly employed world-wide by agricultural/agrichemical service providers to measure biomarkers and for other chemical analysis (plant nutrient levels, plant growth regulators, chemical residue analysis). Other existing easy to use, field-based platforms, many of which are already employed in apple production and apple packing plants can be adapted for biomarker measurement in diverse settings including hand-held electronic devices, dip-stick tests, and bench-top, hand-held, and packing-line mounted non-destructive sorting sensors. Examples of agricultural applications using gene expression biomarkers include an easy-to-use, mail-in platform that measures biomarkers that determine optimum apple and pear fruit harvest date.

As used herein, the term "gene" refers to a polynucleotide that encodes a discrete macromolecular product, be it RNA or a protein, and may include regulatory sequences preceding (5' non-coding sequences) and following (3' non-encoding sequences) the coding sequence. As more than one polynucleotide may encode a discrete product, the term also includes alleles and polymorphisms of a gene that encode the same product, or a functionally associated (including gain, loss, or modulation of function) analog thereof.

The term "gene expression" refers to the process by which RNA and proteins are made from the instructions encoded in genes. Gene expression include transcription and/or translation of nucleic acid material.

The terms "gene expression pattern" and "gene expression profile" are used herein interchangeably. They refer to the expression of an individual gene or of a set of genes. A gene expression pattern may include information regarding the presence of target transcripts in a sample, and the relative or absolute abundance levels of target transcripts.

The term "differentially expressed gene" refers to a gene whose level of expression is different in a subject (or a population of subjects) afflicted with a disorder relative to its level of expression in a healthy or control subject (or a population of healthy or control subjects). The term also includes a gene whose level of expression is different at different stages of, as described here, browning disorder. As will be appreciated by those skilled in the art, a gene may be differentially expressed at the nucleic acid level and/or protein level, may undergo alternative splicing resulting in a different polypeptide product, or the protein could be a target of posttranslational modification and degradation. Differential expression includes quantitative, as well as qualitative, differences in the temporal or cellular expression pattern in a gene or its expression products. As described in greater details below, a differentially expressed gene, alone or in combination with other differentially expressed genes, is useful in a variety of different applications in diagnostic, therapeutic, prognosis and related areas. The expression patterns of the differentially expressed genes disclosed herein can be described as a fingerprint or a signature of browning disorder progression. They can be used as a point of reference to compare and characterize unknown samples and samples for which further information is sought.

The term "RNA transcript" refers to the product resulting from transcription of a DNA sequence. When the RNA transcript is the original, unmodified product of a RNA polymerase catalyzed transcription, it is referred to as the primary transcript. An RNA transcript that has been processed (e.g., spliced, etc.) will differ in sequence from the primary transcript. A processed RNA transcript that is translated into protein is often called a messenger RNA (mRNA). The term "messenger RNA or mRNA" refers to a form of RNA that serves as a template to direct protein biosynthesis. Typically, but not always, the amount of any particular type of mRNA (i.e., having the same sequence, and originating from the same gene) reflects the extent to which a gene has been expressed.

The term "complementary DNA or cDNA" refers to a DNA molecule that is complementary to mRNA. cDNA can be made by DNA polymerase (e.g., reverse transcriptase) or by directed chemical synthesis.

The term "complementary" refers to nucleic acid sequences that base-pair according to the standard Watson-Crick complementary rules, or that are capable of hybridizing to a particular nucleic acid segment under relatively stringent conditions. Nucleic acid polymers are optionally complementary across only portions of their entire sequences.

The term "hybridizing" refers to the binding of two single stranded nucleic acids via complementary base pairing. The terms "specific hybridization" and "specific binding" are used herein interchangeably. They refer to a process in which a nucleic acid molecule preferentially binds, duplexes, or hybridizes to a particular nucleic acid sequence under stringent conditions (e.g., in the presence of competitor nucleic acids with a lower degree of complementarity to the hybridizing strand). In certain embodiments of the present invention, these terms more specifically refer to a process in which a nucleic acid fragment (or segment) from a test sample preferentially binds to a particular genetic probe and to a lesser extent or not at all, to other genetic probes, for example, when these genetic probes are immobilized on an array.

The term "gene expression array" refers to an array comprising a plurality of genetic probes immobilized on a substrate surface that can be used for quantitation of mRNA expression levels. The term "genetic probe", as used herein, refers to a nucleic acid molecule of known sequence, which has its origin in a defined region of the genome and can be a short DNA sequence (i.e., an oligonucleotide), a PCR product, or mRNA isolate. Genetic probes are gene-specific DNA sequences to which nucleic acid fragments from a test sample are hybridized. Genetic probes specifically bind to nucleic acid of complementary or substantially complementary sequence through one or more types of chemical bonds, usually through hydrogen bond formation. Here, we have used RNAseq profiling.

As used herein, the term "a reagent that specifically detects expression levels" refers to one or more reagents used to detect the expression of one or more genes (e.g., genes selected from the groups of 82 (Table 1), 494 (Table 2) and 2330 (Table 3) genes provided herein. Examples of suitable reagents include, but are not limited to, nucleic acid probes capable of specifically hybridizing to the gene of interest, PCR primers capable of specifically amplifying the gene of interest, and antibodies capable of specifically binding to proteins expressed by the gene of interest. The term "amplify" is used in the broad sense to mean creating an amplification product. "Amplification", as used herein, generally refers to the process of producing multiple copies of a desired sequence, particularly those of a sample. A "copy" does not necessarily mean perfect sequence complementarity or identity to the template sequence.

The term "browning disorder profile" refers to a presentation of expression levels of a set of genes in Rosaceous fruit tissue (e.g., tissue at time of harvest, tissue after cold storage imposition). In preferred embodiments, profiles are generated from pooled samples comprising tissue samples from a plurality of fruits at the same stage.

As used herein, the term "modulation of browning disorder progression" refers to the ability of a treatment or management strategy to increase or decrease the likelihood that browning disorder will occur. Generally, useful strategies are those that decrease the likelihood of multiple browning disorder progression.

EXAMPLES

Having now generally described this invention, the same will be better understood by reference to certain specific examples, which are included herein only to further illustrate the invention and are not intended to limit the scope of the invention as defined by the claims.

Example 1

Biomarker Discovery: Early Term Physiological Disorder Risk Assessment

For initial candidate selection, 'Honeycrisp' apples were obtained from 15 orchards distributed among the Lake Chelan/Brewster, Columbia Basin, and Yakima Valley growing regions in Washington State and the Hood River growing region of Oregon between Sep. 2 and Oct. 21, 2011. No pre-harvest treatments were applied, with the exception of Retain™, an ethylene biosynthesis inhibitor, (Valent BioScience Corporation, Libertyville, Ill., USA) to Orchard M. To determine the effects of harvest-timing on postharvest soft scald and soggy breakdown, fruit from one site was harvested at three different times, to represent an early, mid-, and late harvest (Orchard A). On the day of harvest, quality was assessed. Fruit were stored at 1° C. with no atmospheric modification and after 12 weeks, the final incidence of soft scald and soggy breakdown was assessed. For the selection process, the intent was to account for orchard to orchard variation of soft scald/soggy breakdown incidence given the impacts of pre-harvest environment and cultural controls as well as harvest maturity.

Example 2

Biomarker Discovery: Late Term Physiological Disorder Risk Assessment

'Granny Smith' apples were harvested 140 days after full bloom (approximately 1 month prior to commercial harvest) at a research orchard near Orondo, Wash. After transport to the laboratory, analysis of fruit maturity and application of DPA and 1-MCP were performed. Apples were stored in air at 1° C. for up to 6 months. Six replications of 3 fruit per treatment were removed from storage at 1, 2, and 4 weeks and 2, 3, 4, and 6 months. Upon removal from storage, scald development was rated on a 0-4 scale and peel sampled and stored from each treatment for subsequent analysis. In a parallel experiment, additional apples were treated with 2000 mg $L^{-1}$ DPA after 1-4 weeks, and 2 months after storage inception to determine the length of the transitional period during which scald can be suppressed. Scald development on these fruit was evaluated after 2, 3, 4, and 6 months storage.

Example 3

Gene Expression Evaluation: RNA Extraction and RNAseq Profiling

Harvested apple tissue was immediately snap frozen in liquid nitrogen and stored at −80° C. until required. Tissue was ground into a fine powder in liquid $N_2$ and total RNA was extracted from 500 mg of tissue in 0.8 mL of extraction buffer (4M guanidine isothiocyanate, 25 mM EDTA, 2.5% polyvinylpyrollidone (MW 40,000), 2% sarkosyl, 1% β-mercaptoethanol, 0.2M sodium acetate, pH 5.0) at 70° C. for 10 min. Following incubation, chloroform (0.8 mL) was added, tubes vortexed and then spun in a benchtop centrifuge at top speed for 15 minutes. The resulting upper aqueous phase was collected, and a half volume of ethanol added and mixed by inversion. Total RNA was then purified through columns as per the manufacturer's instructions (Qiagen, RNAeasy), and eluted in nuclease free water. The resulting total RNA was checked for integrity via gel electrophoresis then quantified and diluted appropriately.

Libraries for RNAseq were made using 2 µg of total RNA following the method of Zhong et al. (2011. *Cold Spring Harbor Protocols* 8:940-949) and Gapper et al. (2013. *AoB Plants* 5:plt021) with slight modification. In short, mRNA was isolated from total RNA, mRNA was fragmented and used as a template to produce cDNA by reverse transcription using Superscript III (Invitrogen). Following first strand cDNA synthesis, the second strand was synthesized with a dNTP mix incorporating dUTP instead of dTTP by DNA polymerase (Enzymatics). The ends of the double stranded cDNAs were then repaired (Enzymatics), dA tailed by the Klenow enzyme (Enzymatics) and universal adapters ligated to the double stranded cDNA fragments. Following ligation of adapters, the second strand was digested by Uracil DNA Glycosylase (UDG), to enable strand specific enrichment of the library. The UDG digested cDNA was then used as a template to enrich the libraries by PCR with Illumina Tru-seq primers using the high fidelity enzyme Phusion (New England Biolabs) with the following conditions: 95° C. 2 min; 15 cycles of 98° C. 11 s, 65° C. 30 s, 72° C. 25 s; 72° C. 2 min; 4° C. soak.

Libraries were quantified, and 20 ng of each pooled for sequencing. Up to 48 libraries were multiplexed per sequencing reaction using an Illumina HiSeq 2500 next generation sequencer at the Weill Medicine School Sequencing Facility (Cornell University, New York City, N.Y.). Three biological replicates were sequenced for each sample. Short (40 bp) single-end, strand-specific RNASeq reads were filtered by aligning to adapter, ribosomal RNA and tRNA sequences using Bowtie (allowing two mismatches). The resulting high quality reads were aligned to the apple genome (Velasco et al. 2010. *Nat. Genet.* 42(10):833-839) using Tophat (allowing 1 segment mismatch) (Benjamini and Hochberg. 1995. *J. Royal Stat. Soc. Series B (Method.)* 57(1):289-300). Following alignments, raw counts were normalized to reads per kilobase of exon model per million mapped reads (RPKM).

Example 4

In Vitro Transcription and Chilling Stress

Soft scald and soggy breakdown. Only genes with expression levels over 2 RPKM for any replication were considered for candidate selection. Only genes whose expression was variable across the whole data set were considered for subsequent correlation analysis. Peel and cortex expression levels (RPKM) at harvest and following 2 weeks cold storage were compared with soft scald and soggy breakdown incidence (coded as 0=no incidence, 1=0-10%; 2=10-25%; 3=over 25%) taken at 12 weeks using Pearson's correlation analysis. Gene expression with a correlation coefficient above $R^2=10.5001$ or $R^2=10.7001$ for at-harvest and 2 week comparisons (respectively) were considered candidate biomarkers for risk assessment monitoring.

Figure 2:
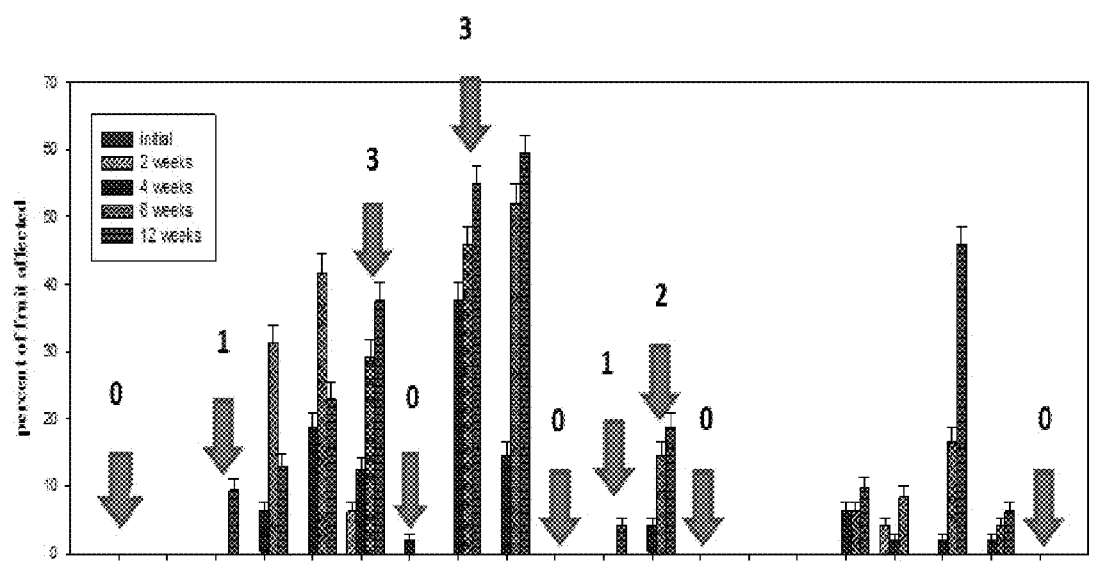
FIG. 2 depicts usage of the combination of harvest maturity and orchard incidence variability to discover risk assessment biomarkers for soft scald and soggy breakdown (shown in FIGS. 1C and 1D) and other early-term physiological storage disorders of apple and other Rosaceous fruit crops. Soft scald was categorized for statistical analysis on a scale of 0-3 (0=no incidence, 1=0-10%; 2=10-25% and 3=over 25%).
Figure 4:
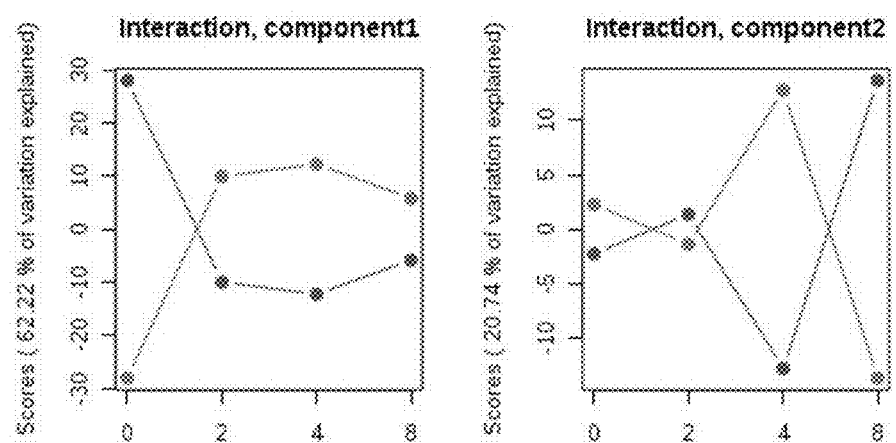
FIG. 4 depicts a summary of overall changes of gene expression in 'Honeycrisp' apple from high (green) and low (red) risk orchards. The left graph indicates that the largest impact on the transcriptome occurred between harvest and 2 weeks when cold storage was imposed.

Soft scald and soggy breakdown began to develop beginning at 4 weeks in some high risk orchards eventually developing to maximum incidence and severity by 12 weeks, as expected from earlier work using this cultivar (FIG. 2). The RNAseq protocol provided one of many sensitive, accurate, and precise platform for candidate expression evaluation in both apple peel and flesh. Of the 63,541 genes screened in this experiment, 82 candidates were found useful for assessing risk at-harvest (Table 1) and 494 for 2 week risk assessment of peel and/or cortex tissue (Table 2). Biomarker gene expression primarily increased although some decreased with increasing risk. Accordingly, a summary of overall gene expression levels indicated that more models were linked with eventual injury at 2 weeks, or following cold storage imposition, rather than at-harvest (FIG. 4) indicating that the cold stress that provokes the injury followed by candidate expression evaluation will provide the most accurate risk assessment. Given the dramatic change in gene expression provoked by cold storage imposition, measuring candidate expression levels both before and at one or more points following cold storage may yield even more accurate information by documenting upward or downward trends. Similarly, monitoring multiple risk assessment biomarkers can better ensure that changes are based on more biochemical systems associated with risk.

Superficial scald. Only genes with peel expression levels over 2 RPKM for any time point were considered for modeling and candidate selection yielding 35,644 gene models for subsequent screening. Gene models alongside superficial scald incidence were clustered across all 3 treatments over the 6 month storage period using k-means correlation clustering algorithm (Matlab) yielding 86 clusters. Gene models with increasing expression in control fruit, but not antioxidant or 1-MCP-treated fruit 2 months or more prior to superficial scald incidence, were considered candidates. K-means correlations clustering was used to group genes similarly expressed over the entire experiment in all treatments. Clusters comprised of superficial scald risk storage monitoring biomarker candidates were those that correlated $R^2 = 0.700$ with conjugated trienol (CTOL) levels or injury incidence.

Figures 3A, 3B:
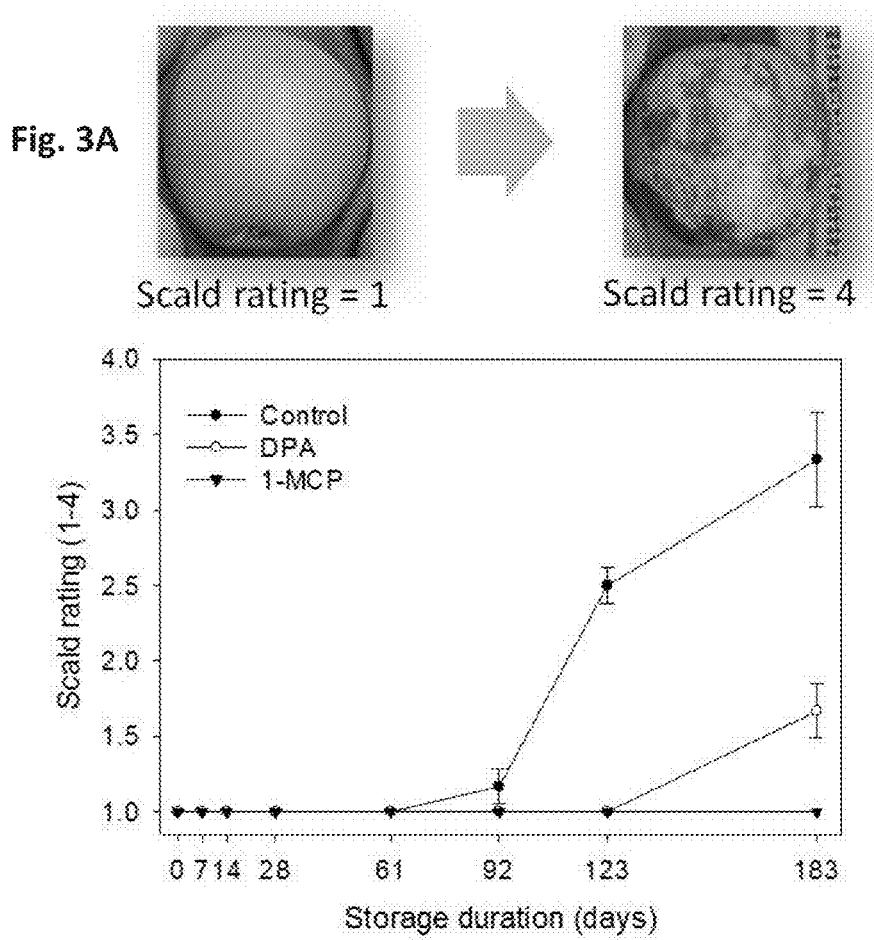
FIG. 3A shows superficial scald development of 'Granny Smith' apples.
FIG. 3B depicts the usage of this combination to discover risk assessment biomarkers for this and other late-term physiological storage disorders of apple and other Rosaceous fruit crops. Control apples (no crop protectants applied) developed the highest incidence of superficial scald (FIG. 3B). This "pharmaceutical" contrast was used to discover risk assessment biomarkers for this and other late-term postharvest physiological disorders of Rosaceous fruit crops. Abbreviations (DPA, diphenylamine; 1-MCP, 1-methylcyclo-propene).

The first symptoms of superficial scald began to develop on control fruit between 2 and 3 months and continued to increase in severity until 6 months as is typical for this cultivar when stored in air without any control steps taken (FIG. 3B). Both crop protectants either eliminated or markedly reduced symptom development while providing two physiologically different means of control to select the most accurate risk assessment candidates from. Because superficial scald can be adequately controlled using appropriate storage conditions, indicating whether storage conditions are actually working or monitoring risk during storage is the most useful tool for this disorder. Increases in superficial scald risk-associated gene expression began at 1 month for a few candidates (FIG. 5) 690 candidates for early indication of scald risk (Table 3). Monitoring multiple risk assessment biomarkers can better ensure that changes are based on more biochemical systems associated with risk.

Example 5

Risk Assessment

Multiple candidates are part of previously unidentified metabolic responses to stress and, monitoring these candidates appear to be effective for assessing risk across disorders and cultivars following, or during, cold stress events. Changes in expression levels before and following cold storage imposition as well as fold difference between high risk and low risk orchards for developing soft scald/soggy breakdown (early-term disorders) are included as examples of broadly effective risk assessment biomarkers (Table 7). For soft scald/soggy breakdown risk assessment, the fold difference from the highest incidence orchard to lowest incidence orchard is indicated as well as the % change in expression following cold storage imposition. For superficial scald, a late-term disorder, the time from first detection of risk using a specific biomarker until symptom appearance and the % change in expression during that period are indicated. Expression of many of these genes change dramatically indicating repeated measurement around the point of cold storage imposition may be used to improve confidence. Monitoring the same genes during storage of cultivars at risk for developing superficial scald or other late-term apple and pear physiological disorders leads to expression changes that ultimately culminate in symptom development 1 month or more later. Increased expression of up to 98% transpired up to 6 weeks prior to disorder development. Biomarker genes are from multiple stress-related biochemical processes not related to stress in fruit prior to this discovery. Monitoring biomarkers from multiple processes can be used for a more confident evaluation. For instance, candidates putatively involved in phenolic metabolism and indole acetic acid (IAA) metabolism could be monitored in tandem.

TABLE 7

Apple protein Accession Numbers (Velasco et al., 2010; Retrieved from the Internet: Rosaceae.org) of biomarker genes for early and late term apple peel and flesh disorders.

| | Early-term disorders | | Late-term disorders | |
|---|---|---|---|---|
| Gene accession number | Fold difference[1] | % change[2] | Time before symptoms (weeks)[3] | % change[4] |
| MDP0000591260 | 7.8*, nd | 75.0 | 8 | 52.8 |
| MDP0000272351 | 6.4, 11 | 89.0 | 8 | 41.9 |
| MDP0000145813 | 11.5, 13.8 | 43.9 | 8 | 82.0 |
| MDP0000551974 | 16.9, 56.6 | 86.4 | 8 | 46.2 |
| MDP0000424447 | 21.9, 54.4 | 85.6 | 8 | 36.6 |
| MDP0000215525 | 20.2, 29.0 | 46.3 | 8 | 83.9 |
| MDP0000715898 | 12.7, 15.5 | 81.9 | 6 | 60.1 |
| MDP0000306121 | 18.2, 30.0 | 46.6 | 8 | 84.3 |
| MDP0000290801 | 19.1, 41.0 | 56.2 | 8 | 83.4 |
| MDP0000307237 | 17.9, 27.4 | 40.4 | 6 | 81.1 |
| MDP0000769764 | 20.1, 224 | 59.6 | 8 | 77.7 |
| MDP0000545122 | 13.6, 27.0 | 88.2 | 6 | 44.7 |
| MDP0000733506 | 22.0, 31.3 | 82.4 | 8 | 48.0 |
| MDP0000617956 | 47.6, nd | 82.3 | 8 | 46.9 |
| MDP0000755567 | 11.6, 25.2 | 96.6 | 6 | 17.9 |
| MDP0000334047 | 11.0, 8.09 | 64.4 | 6 | 36.7 |
| MDP0000688645 | 34.2, 16.4 | 98.1 | 8 | 43.9 |
| MDP0000576682 | 4.8, nd | −10.6 | 6 | 66.2 |
| MDP0000191939 | 4.0, 3.1 | −6.3 | 8 | 46.7 |
| MDP0000195213 | 15.3, 19.4 | 63.3 | 8 | 41.8 |
| MDP0000211643 | 19.5, 8.2 | 82.2 | 8 | 20.3 |
| MDP0000292164 | 9.0, 16.4 | 64.7 | 6 | 50.2 |
| MDP0000130244 | 51.0, 20.5 | 96.8 | 6 | 75.2 |
| MDP0000190809 | 4.9, 10.0 | 62.8 | 6 | −22.1 |
| MDP0000748916 | 10.0, 4.2 | 48.8 | 6 | 21.6 |
| MDP0000199009 | 8.4, 5.3 | 62.8 | 6 | 21.5 |
| MDP0000143611 | 1.8, 2.8 | 17.9 | 8 | 46.7 |
| MDP0000166302 | 1.6, 2.1 | 18.9 | 8 | 24.5 |
| MDP0000278475 | 3.3, 4.3 | 34.8 | 8 | 21.8 |
| MDP0000640906 | 4.1, 8.1 | 85.9 | 6 | 28.0 |

[1]Fold difference of biomarker levels at 2 weeks between GH (highest risk) and GLE1 (lowest risk).
[2]Percent gene expression change in GH harvest to 2 weeks.
[3]The time (in weeks) between elevated biomarker levels in high risk fruit and symptom development at 3 months.
[4]Percent change in gene expression in high risk fruit from 2 to 8 weeks.

Figure 6:
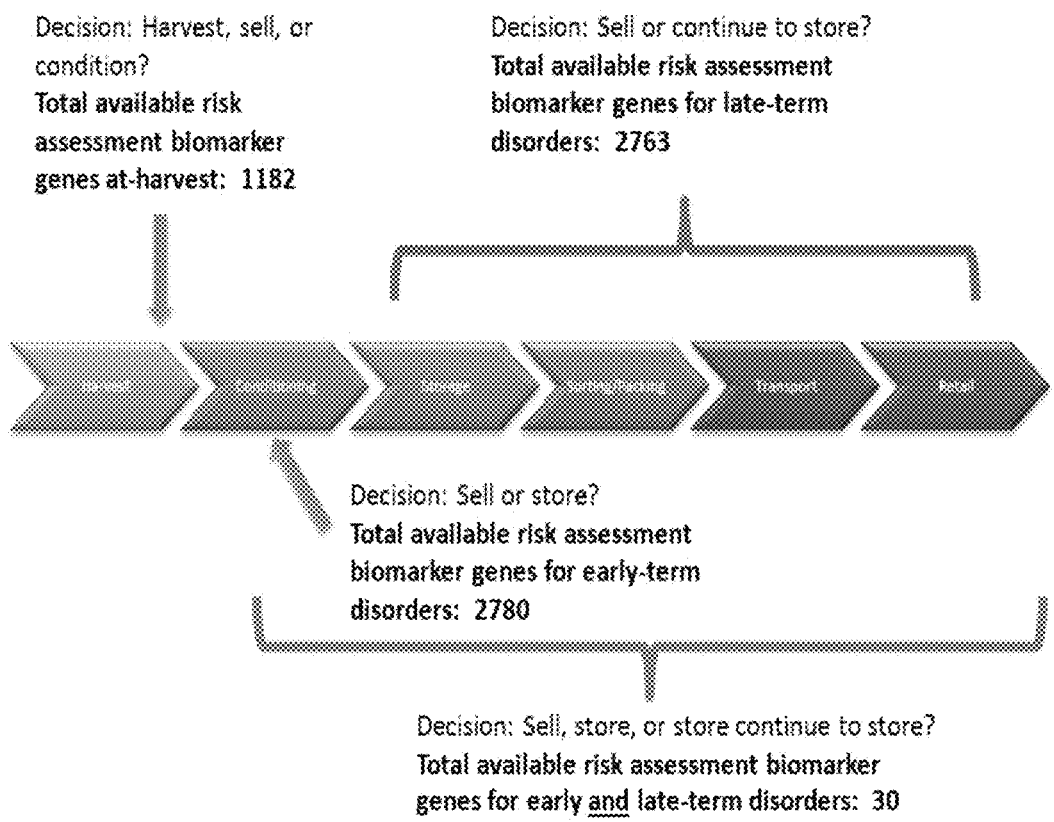
FIG. 6 depicts a testing scheme for a disorder risk management system. If risk assessment biomarker levels are higher (or lower, see Table), decisions on how long a particular lot, alone or compared to other lots, should proceed through the supply chain can be made at key decision points based on the assessed risk for developing various browning disorders.

As apple and pear fruit transition through the supply chain, they undergo many stress events. Our invention allows for an easy means for interrogating fruit undergoing these transitions to assess risk for developing these disorders. FIG. 6 provides a scheme for some of the ways which our biomarker-based risk assessment scheme can be used to direct storage and marketing decisions that can mitigate or avoid disorder development.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A method comprising:
   a) isolating mRNA from peel tissue or cortex tissue of at least one apple or at least one pear;
   b) performing reverse transcription PCR on said isolated mRNA; and
   c) assaying the level of expression of a set of biomarkers, wherein the set of biomarkers consists of: MDP0000848515, MDP0000238780, MDP0000260007, MDP0000153149, MDP0000585315, MDP0000273646, MDP0000216786, MDP0000180580, MDP0000737425, MDP0000298967, MDP0000808492, MDP0000273866, MDP0000353053, MDP0000910032, MDP0000145050, MDP0000263844, MDP0000158999, MDP0000547254, MDP0000196325, MDP0000224653, MDP0000321382, MDP0000270602, MDP0000233661, MDP0000665342, MDP0000246831, MDP0000823528, MDP0000408705, MDP0000518327, MDP0000291249, MDP0000154589, MDP0000202817, MDP0000590954, MDP0000312397, MDP0000213383, MDP0000529726, MDP0000312071, MDP0000639894, MDP0000307665, MDP0000183676, MDP0000754521, MDP0000797616, MDP0000818877, MDP0000782908, MDP0000266443, MDP0000562305, MDP0000228366, MDP0000361351, MDP0000737001, MDP0000412192, MDP0000223032, MDP0000149492, MDP0000264361, MDP0000125882, MDP0000498460, MDP0000163006, MDP0000225132, MDP0000329063, MDP0000170865, MDP0000665685, MDP0000196079, MDP0000200783, MDP0000182956, MDP0000862371, MDP0000321792, MDP0000441757, MDP0000313657, MDP0000599531, MDP0000297583, MDP0000272980, MDP0000317502, MDP0000268175, MDP0000722139, MDP0000637194, MDP0000125700, MDP0000287262, MDP0000745534, MDP0000164966, MDP0000389794, MDP0000318068, MDP0000322237, MDP0000225326, and MDP0000125411.

* * * * *